US006379927B1

(12) United States Patent
Antelman et al.

(10) Patent No.: US 6,379,927 B1
(45) Date of Patent: Apr. 30, 2002

(54) RETINOBLASTOMA FUSION PROTEINS

(75) Inventors: Douglas Antelman, Encinitas, CA (US); Richard J. Gregory, Westford, MA (US); Kenneth N. Wills, Encinitas, CA (US)

(73) Assignee: Canji, Inc., San Diego, CA (US)

( * ) Notice: Subject to any disclaimer, the term of this patent is extended or adjusted under 35 U.S.C. 154(b) by 0 days.

(21) Appl. No.: 09/315,113

(22) Filed: May 19, 1999

Related U.S. Application Data

(60) Division of application No. 08/801,092, filed on Feb. 14, 1997, now Pat. No. 6,074,850, which is a continuation-in-part of application No. 08/751,517, filed on Nov. 15, 1996, now abandoned.

(51) Int. Cl.$^7$ .......................... C12P 21/04; C12P 21/08; C07K 1/00; A61K 39/00
(52) U.S. Cl. .................... 435/69.7; 530/350; 530/387.1; 424/192.1
(58) Field of Search ............................... 530/350, 300, 530/387.3; 435/69.7; 424/192.1

(56) References Cited

U.S. PATENT DOCUMENTS

| 4,235,871 A | 11/1980 | Papahadjopoulos et al. ..... 424/450 |
| 4,501,728 A | 2/1985 | Geho et al. .................. 424/450 |
| 4,837,028 A | 6/1989 | Allen ........................ 424/1.21 |
| 5,019,369 A | 5/1991 | Presant et al. .............. 424/1.21 |

FOREIGN PATENT DOCUMENTS

| WO | WO 92/06180 | 4/1992 | ............ C12N/7/00 |
| WO | WO 93/14188 | 7/1993 | ............ C12N/5/00 |
| WO | WO 93/19768 | 10/1993 | .......... A61K/37/00 |
| WO | WO 93/20221 | 10/1993 | ........... C12N/15/86 |
| WO | WO 94/06922 | 3/1994 | ........... C12N/15/87 |
| WO | WO 94/06923 | 3/1994 | ........... C12N/15/87 |
| WO | WO 9507708 | 3/1995 | |

OTHER PUBLICATIONS

Fueyo, et al., "Expression of exogenous p16/CDKN2 products growth arrest in a glioma cell line that does not express RB protein," Proceedings of the American Association for Cancer Research, 37:A49 (1996).
Xu, et al., "Enhanced Tumor Suppressor Gene Therapy via eplication–deficient Adenivirus Vectors Expressing an N–Terminal Truncated Retinoblastoma Protein," Cancer Research, 56:2245–2249 (1996).
Krek et al., Cell, vol. 83, p. 1149–1158, Dec. 1995.*
Sellers et al., Proc. Natl. Acad. Sci. USA, vol. 92, pp. 11544–11548, Dec. 1995.*
Adnane et al., The Journal of Biological Chemistry, vol. 270(15), pp. 8827–8843, Apr. 1995.*
Adams, P.D. et al., "Transcriptional control by E2F," Cancer Biology 6:99–108 (1995).

Adnane, J. et al., "The Retinoblastoma Susceptibility Gene Product Represses Transcription When Directly Bound to the Promoter," J. Biol. Chem. 270(15):8837–8843 (1995).
Antelman, D. et al., "Inhibition of tumor cell proliferation in vitro and in vivo by exogenous p110$^{RB}$, the retinoblastoma tumor suppressor protein," Oncogene 10:697–704 (1995).
Arteaga, C.L. et al., "Tissue–targeted Antisense c–fos Retroviral Vector Inhibits Established Breast Cancer Xenografts in Nude Mice," Cancer Research 56:1098–1103 (1996).
Babajko, S. et al., "Interplay of the Liver–Enriched Trans-acting Factors, DBP and HNF1, in the Transactivation of Human IGFBP–1 Promoter," Biochem. & Biophys. Research Commun. 196(1):480–486 (1993).
Banas, B. et al., "Analysis of the promoter of the human prostatic acid phosphatase gene," Biochim. Biophy. Acta 1217:188–194 (1994).
Beijersbergen, R.L. et al., "E2F–4, a new member of the E2F gene family, has oncogenic activity and associates with p107 in vivo," Genes & Devel. 8:2680–2690 (1994).
Bingle, C.D. et al., "Interaction of CCAAT/enhancer–binding protein α and β with the rat caeruloplasmin gene promoter," Biochem. J. 294:473–479 (1993).
Bookstein, R. et al., "Suppression of Tumorigenicity of Human Prostate Carcinoma Cells by Replacing a Mutated RB Gene," Science 247:712–715 (1990).
Buck, V. et al., "Molecular and functional characterisation of E2F–5, a new member of the E2F family," Oncogene 11:31–38 (1995).
Chang, M.W. et al., "Cytostatic Gene Therapy for Vascular Proliferative Disorders with a Constitutively Active Form of the Retinoblastoma Gene Product," Science 267:518–522 (1995).
Clowes, A.W. et al., "Kinetics of Cellular Proliferation after Arterial Injury," Lab. Invest. 49(3) 327–333 (1983).
Cox, G.A. et al., "Overexpression of dystrophin in transgenic mdx mice eliminates dystrophic symptoms without toxicity," Nature 364:725–729 (1993).
Curiel, D.T. et al., "Adenovirus enhancement of transferrin–polylysine–mediated gene delivery," Proc. Natl. Acad. Sci. U.S.A. 88:8850–8854 (1991).
Dalesandro, J. et al., "Gene Therapy for Donor Hearts: Ex vivo Liposome–Mediated Transfection," J. Thoracic and Cardiovascular Surgery 111(2):416–422 (1996).
Dobrowolski, S.F. et al., "An E2F dominant negative mutant blocks E1A induced cell cycle progression," Oncogene 9:2605–2612 (1994).

(List continued on next page.)

Primary Examiner—Deborah J. R. Clark
Assistant Examiner—Shin–Lin Chen
(74) Attorney, Agent, or Firm—Townsend and Townsend and Crew LLP

(57) ABSTRACT

Fusions of the transcription factor E2F and the retinoblastoma protein RB are provided, along with methods of treatment of hyperproliferative diseases.

11 Claims, 83 Drawing Sheets

OTHER PUBLICATIONS

Dowdy, S.F. et al., "Physical Interaction of the Retinoblastoma Protein with Human D Cyclins," *Cell* 73:499–511 (1993).

Dusetti, N.J. et al., "Structural Organization of the Gene Encoding the Rat Pancreatitis–associated Protein," *J. Biol. Chem.* 268(19):14470–14475 (1993).

Eisenberger, C.L. et al., "Differential Regulation of the Rat Phosphoenolpyruvate Carboxykinase Gene Expression in Several Tissues of Transgene Mice," *Mol. Cell Biol.* 12(3):1396–1403 (1992).

Fontaine, R.N. et al., "Structure of the Rat Pancreatic Cholesterol Esterase Gene," *Biochemistry* 30:7008–7014 (1991).

Forss–Petter, S. et al., "Transgenic Mice Expressing β–Galactosidase in Mature Neurons under Neuron–Specific Enolase Promoter Control," *Neuron* 5:187–197 (1990).

French, B.A. et al., "Percutaneous Transluminal In Vivo Gene Transfer by Recombinant Adenovirus in Normal Porcine Coronary Arteries, Atherosclerotic Arteries, and Two Models of Coronary Restenosis," *Circulation* 90(5):2402–2413 (1994).

Friedman, J.M. et al., "Cellular Promoters Incorporated into the Adenovirus Genome: Cell Specificity of Albumin and Immunoglobulin Expression," *Mol. Cell Biol.*, 6(11):3791–3797 (1986).

Ginsberg, D. et al., "E2F–4, a new member of the E2F transcription factor family, interacts with p107," *Genes & Devel.* 8:2665–2679 (1994).

Gorman, C.M. et al., "Recombinant Genomes Which Express Chloramphenicol Acetyltransferase in Mammalian Cells," *Mol. Cell Biol.* 2(9):1044–1051 (1982).

Hanson, R.D. et al., "The 5'–Flanking Region of the Human CGL–1/Granzyme B Gene Targets Expression of a REporter Gene to Activated T–lymphocytes in Transgenic Mice," *J. Biol. Chem.* 266(36):24433–24438 (1991).

Hatzoglou, M. et al., "Hepatic Gene Transfer in Animals Using REtroviruses Containing the Promoter from the Gene for Phosphoenolpyruvate Carboxykinase," *J. Biol. Chem.* 256(28):17285–17293 (1990).

Helftenbein, G. et al., "Expression of the Uteroglobin Promoter in Epithelial Cell Lines from Endometrium," *Annals New York Acad. Sci.* Bulletti C. et al., eds., New York Academy of Sciences, New York, 622:69–79 (1991).

Hemstrom, C. et al., "Gene Product of Region E4 of Adenovirus Type 5 Modulates Accumulation of Certain Viral Polypeptides," *J. Virol.* 62(9):3258–3264 (1988).

Hiebert, S.W., "Regions of the Retinoblastoma Gene product Required for Its Interaction with the E2F Transcription Factor Are Necessary for E2 Promoter Repression and pRb–Mediated Growth Suppression," *Mol. Cell Biol.* 13(6):3384–3391 (1993).

Houchins, J.P. et al., "Genomic structure of nkg5, a human NK and T cell–specific activation gene," *Immunogenetics* 37:102–107 (1993).

Houglum, K. et al., "LAP (NF–IL6) Transactivates the Collagen $\alpha_1$(I) Gene from a 5' Regulatory Region," *J. Clin. Invest.*, 94:808–814 (1994).

Huang, S. et al., "A cellular protein that competes with SV40 T antigen for binding to the retinoblastoma gene product," *Nature* 350:160–162 (1991).

Huber, B.E. et al., "Retroviral–mediated gene therapy for the treatment of hepatocellular carcinoma: An innovative approach for cancer therapy," *Proc. Nat. Acad. Sci. U.S.A.,* 88:8039–8043 (1991).

Ilantzis, C. et al., "Identification of a Human cancer Related Organ–Specific Neoantigen," *Microbiol. Immunol.* 37(2):119–128 (1993).

Ivey–Hoyle, M. et al., "Cloning and Characterization of E2F–2, a Novel Protein with the Biochemical Properties of Transcription Factor E2F," *Mol. Cell Biol.* 13(12):7802–7812 (1993).

Jahroudi, N. et al., "Endothelial–Cell–Specific Regulation of von Willebrand Factor Gene Expression," *Mol. Cell Biol.* 14(2):999–1008 (1994).

Kaspar, F. et al., "Characterization of Two Point Mutations in the Androgen REceptor Gene of Patients with Perineoscrotal Hypospadia," *J. Steroid Biochem. Molec. Biol.* 47(1–6):127–135 (1993).

Kaye, F.J. et al., "A single amino acid substitution results in a retinoblastoma protein defective in phosphorylation and oncoprotein binding," *Proc. Natl. Acad. Sci. U.S.A.* 87:6922–6926 (1990)).

Keller, S.A. et al., "Regulation of amylase gene expression in diabetic mice is mediated by a cis–acting upstream element close to the pancreas–specific enhancer," *Genes & Devel.* 4:1316–1321 (1990).

Koc, O.N. et al., "Transfer of Drug Resistance Genes Into Hematopoietic Progenitors to Improve Chemotherapy Tolerance," *Seminars in Oncology* 23(1):46–65 (1996).

Krek, W. et al., "Negative REgulation of the Growth–Promoting Transcription Factor E2F–1 by a Stably Bound Cyclin A–Dependent Protein Kinase," *Cell* 78:161–172 (1994).

Krek, W. et al., "Cyclin A–Kinase Regulation of E2F–1 DNA Binding Function Underlies Suppression of an S Phase Checkpoint," *Cell* 83:1149–1158 (1995).

Kruse, F. et al., "An endocrine–specific element is an integral component of an exocrine–specific pancreatic enhancer," *Genes & Devel.* 7:774–786 (1993).

Lake, R.A. et al., "A 3' transcriptional enhancer regulates tissue–specific expression of the human CD2 gene," *EMBO J.* 9(10):3129–3136 (1990).

Lee, W.H. et al., "The retinoblastoma susceptibility gene encodes a nuclear phosphoprotein associated with DNA binding activity," *Nature* 329:642–645 (1987).

Lee, Y.H. et al., "Multiple, Functional DBP Sites on the promoter of the Cholesterol 7α–Hydroxylase P450 Gene, CYP7," *J. Biol. Chem.* 269(20):14681–14689 (1994).

Li, S.P. et al., "cis–Acting Elements Responsible for Interleukin–6 Inducible C–reactive Protein Gene Expression," *J. Biol. Chem.* 265(7):4136–4142 (1990).

Lilja, H., "Structure, function, and regulation of the enzyme activity of prostate–specific antigen," *World J. Urol.* 11:188–191 (1993).

Lo, K. et al., "LyF–1, a Transcriptional Regulator That Interacts with a Novel Class of Promoters for Lymphocyte–Specific Genes," *Mol. Cell Biol.* 11(10):5229–5243 (1991).

Luskey, K.L., "Conservation of Promoter Sequence but Not Complex Intron Splicing Pattern in Human and Hamster genes for 3–Hydroxy–3–Methylglutaryl Coenzyme A Reductase," *Mol. Cell Biol.* 7(5):1881–1893 (1987).

Makarov, S.S. et al., "Suppression of experimental arthritis by gene transfer of interleukin 1 receptor antagonist cDNA," *Proc. Natl. Acad. Sci. U.S.A.* 93:402–406 (1996).

Maxwell, I.H. et al., "Expression of the Diphtheria Toxin A–Chain Coding Sequence under the Control of Promoters and Enhancers from Immunoglobulin Genes as a Means of Directing Toxicity to B–Lymphoid Cells," *Cancer Res.* 51:4299–4304 (1991).

Mendelzon, D. et al., "The binding site for the liver–specific transcription factor Tf–LF1 and the TATA box of the human transferrin gene promoter are the only elements necessary to direct liver specific transcription in vitro," *Nucl. Acids Res.* 18(19):5717–5721 (1990).

Nakano, Y. et al., "Transcriptional regulatory elements in the 5' upstream and first intron regions of the human smooth muscle (aortic type) α–actin–encoding gene," *Gene* 99:285–2898 (1991).

Nolet, S. et al., "Prostatic secretory protein $PSP_{94}$: gene organization and promoter sequence in Rhesus monkey and human," *Biochim. Biophys. Acta* 1089:247–249 (1991).

Nolta, J.A. et al., "Transduction of pluripotent human hematopoietic stem cells demonstrated by clonal analysis after engraftment in immune–deficient mice," *Proc. Natl. Acad. Sci. U.S.A.* 93:2414–2419 (1996).

Petropoulos, C.J. et al.,"Using Avian Retroviral Vectors for Gene Therapy," *J. Virol.* 66(6):3391–3397 (1992).

Plank, C. et al., "The Influence of Endosome–disruptive Peptides on Gene Transfer Using Synthetic Virus–like Gene Transfer Systems," *J. Biol. Chem.* 269(17):12918–12924 (1994).

Qin, X.Q. et al., "Identification of a growth suppression domain within the retinoblastoma gene product," *Genes & Devel.* 6:953–964 (1992).

Raper, S.E. et al., "Safety and Feasibility of Liver–Directed Ex Vivo Gene Therapy for Homozygous Familial Hypercholesterolemia," *Annals. of Surgery* 223(2):116–126 (1996).

Reddy, S. et al., "Structure of the Human Smooth Muscle α–Actin Gene," *J. Biol. Chem.* 265(3):1683–1687 (1990).

Rice, D.A. et al., "Analysis of the Promoter Region of the Gene Encoding Mouse Cholesterol Side–chain Cleavage Enzyme," *J. Biol. Chem.* 265(20):11713–11720 (1990).

Rosenthal, N., "Identification of Regulatory Elements of Cloned Genes with Functional Assays," *Meth. of Enzymology* 152:704–720 (1987).

Schwartz, M.L. et al., "Brain–specific Enhancement of the Mouse Neurofilament Heavy Gene Promoter in Vitro," *J. Biol. Chem.* 269(18):13444–13450 (1994).

Sellers, W.R. et al., "A potent transrepression domain in the retinoblastoma protein induces a cell cycle arrest when bound to E2F sites," *Proc. Natl. Acad. Sci. U.S.A.* 92:11544–11548 (1995).

Sharkey, R.M. et al., "Phase I Clinical Evaluation of a New Murin Monoclonal antibody (Mu–9) against Colon–Specific Antigen–p for Targeting Gastrointestinal Carcinomas," *Cancer Supp.* 73(3):864–877 (1994).

Smith, J.R. et al., "Identification of–Nucleotides Responsible for Enhancer Activity of Sterol Regulatory Element in Low Density Lipoprotein Receptor Gene," *J. Biol. Chem.* 265(4):2306–2310 (1990).

Svensson, E.C. et al., "Organization of the β–Galactoside α2, 6–Sialyltransferase Gene," *J. Biol. Chem.* 265(343):20863–20868 (1990).

Szoka, F. et al., "Comparative Properties and Methods of Preparation of Lipid Vesicles (Liposomes)," *Ann. Rev. Biophys. Bioeng.* 9:467–508 (1980).

Talamonti, M.S. et al., "Increase in Activity and Level of $pp60^{c-src}$ in Progressive Stages of Human Colorectal Cancer," *J. Clin. Invest.* 91:53–60 (1993).

Tamura, S. et al., "Sequence motif in control regions of the $H^+/K^+$ ATPase α and β subunit genes recognized by gastric specific nuclear protein(s)," *FEBS Lett.* 298(2,3):137–141 (1992).

Tanizawa, Y. et al., "Human Glucokinase Gene: Isolation, Structural Characterization, and Identification of a Microsatellite Repeat Polymorphism," *Mol. Endocrinol.* 6(7):1070–1081 (1992).

Thean, E.T. et al., "Serum human α–lactalbumin as a marker for breast cancer," *Br. J. Cancer* 61:773–775 (1990).

Thimmappaya, B. et al., "Adenovirus VAI RNA Is Required for Efficient Translation of Viral mRNAs at Late Times after Infection," *Cell* 31:543–551 (1982).

Vairo, G. et al., "Functional interaction between E2F–4 and p130: evidence for distinct mecahnisms underlying growth suppression by different retinoblastoma protein family members," *Genes & Devel.* 9:869–881 (1995).

Weintraub, S.J. et al., "Retinoblastoma protein switches the E2F site from positive to negative element," *Nature* 358:259–261 (1992).

Wen, S.F. et al.,"Retinoblastoma protein monoclonal antibodies with novel charateristics," *J. Immunol. Meth.* 169:231–240 (1994).

Willard, J.E. et al., "Genetic Modification of the Vessel Wall," *Circulation* 89(5):2190–2197 (1994).

Wills, K.N. et al., "Development and Characterization of Recombinant Adenoviruses Encoding Human p53 for Gene Therapy of Cancer," *Hum. Gene Therapy* 5:1079–1088 (1994).

Wills, K.N. et al., "Gene therapy for hepatocellular carcinoma: Chemosensitivity conferred by adenovirus–mediated transfer of the HSV–1 thymidine kinase gene," *Canc. Gene Therapy* 2(3):191–197 (1995).

Wu, C.L. et al., "In Vivo Association of E2F and DP Family Proteins," *Mol. Cell Biol.* 15(5):2536–2546 (1995).

Wu, G.Y. et al., "Receptor–mediated Gene Delivery and Expression in Vivo," *J. Biol. Chem.* 263(29):14621–14624 (1988).

Wu, K.J. et al., "Transactivation of Pancreas–Specific Gene Sequences in Somatic Cell Hybrids," *Mol. Cell Biol.* 11(9):4423–4430 (1991).

Xu, G. et al., "Multiple members of the E2F transcription factor family are the products of oncogenes," *Proc. Natl. Acad. Sci. U.S.A.* 92:1357–1361 (1995).

Shimizu, R.T. et al., "The Smooth Muscle α–Actin Gene Promoter Is Differentially Regulated in Smooth Muscle versus Non–smooth Muscle Cells," *J. Biol. Chem.* 270(13):7631–7643 (1995).

* cited by examiner

```
          10         20         30         40         50         60
MALAGAPAGG PCAPALEALL GAGALRLLDS SQIVIISAAQ DASAPPAPTG PAAPAAGPCD 70         80         90        100        110        120
PDLLLFATPQ APRPTPSAPR PALGRPPVKR RLDLETDHQY LAESSGPARG RGRHPGKGVK 130        140        150        160        170        180
SPGEKSRYET SLNLTTKRFL ELLSHSADGV VDLNWAAEVL KVQKRRIYDI TNVLEGIQLI 190        200        210        220        230        240
AKKSKNHIQW LGSHTTVGVG GRLEGLTQDL RQLQESEQQL DHLMNICTTQ LRLLSEDTDS 250        260        270        280        290        300
QRLAYVTCQD LRSIADPAEQ MVMVIKAPPE TQLQAVDSSE NFQISLKSKQ GPIDVFLCPE 310        320        330        340        350        360
ETVGGISPGK TPSQEVTSEE ENRATDSATI VSPPPSSPPS SLTTDPSQSL LSLEQEPLLS 370        380        390        400        410        420
RMGSLRAPVD EDRLSPLVAA DSLLEHVRED FSGLLPEEFI SLSPPHEALD YHFGLEEGEG 430        440        450        460        470        480
IRDLFDCDFG DLTPLDF*..  .........  .........  .........  .........
```

FIG. 1A.

```
         10         20         30         40         50         60
GGAATTCCGT GGCCGGGACT TTGCAGGCAG CGGGGGCCGG GGGCGGAGCG GGATCGAGCC 70         80         90        100        110        120
CTCGCCGAGG CCTGCCGCCA TGGGCCCGCG CCGCCGCCGC CGCCTGTCAC CCGGGCCGCG 130        140        150        160        170        180
CGGGCCGTGA GCGTCATGGC CTTGGCCGGG GCCCCTGCGG GCGGCCCATG CGCGGCGGCG 190        200        210        220        230        240
CTGGAGGCCC TGCTCGGGGC CGGCGGCGCTG CGGCTGCTCG ACTCCCTCGCA GATCGTCATC 250        260        270        280        290        300
ATCTCCGCCG CGCAGGACGC CAGCGCCCCG CCGGCTCCCA CCGGCCCCGC GGCGCCCGCC 310        320        330        340        350        360
GCCGCCCCT GCGACCCTGA CCTGCTGCTC TTCGCCACAC CGCAGGCGCC CCGGCCCACA 370        380        390        400        410        420
CCCAGTGCGC CGCGGCCCGC GCTCGGCCGC CCGGCCGGTGA AGCGGAGGCT GGACCTGAA 430        440        450        460        470        480
ACTGACCATC AGTACCTGGC CGAGAGCAGT GGGCCAGCTC GGGGCAGAGG CCGCCATCCA 490        500        510        520        530        540
GGAAAAGGTG TGAAATCCCC GGGGGAGAAG TCACGCTATG AGACCTCACT GAATCTGACC 550        560        570        580        590        600
ACCAAGCGCT TCCTGGAGCT GCTGAGCCAC TCGGCTGACG GTGTCGTCGA CCTGAACTGG 610        620        630        640        650        660
GCTGCCGAGG TGCTGAAGGT GCAGAAGCGG CGCATCTATG ACATCACCAA CGTCCTTGAG
```

FIG. 1B-1.

```
     670        680        690        700        710        720
GGCATCCAGC TCATTGCCAA GAAGTCCAAG AACCACATCC AGTGGCTGGG CAGCCACACC 730        740        750        760        770        780
ACAGTGGGCG TCGGCGGACG GCTTGAGGGG TTGACCCAGG ACCTCCGACA GCTGCAGGAG 790        800        810        820        830        840
AGCGAGCAGC AGCTGGACCA CCTGATGAAT ATCTGTACTA CGCAGCTGCG CCTGCTCTCC 850        860        870        880        890        900
GAGGACACTG ACAGCCAGCG CCTGGCCTAC GTGACGTGTC AGGACCTTCG TAGCATTGCA 910        920        930        940        950        960
GACCCTGCAG AGCAGATGGT TATGGTGATC AAAGCCCCTC CTGAGACCCA GCTCCAAGCC 970        980        990       1000       1010       1020
GTGGACTCTT CGGAGAACTT TCAGATCTCC CTTAAGAGCA AACAAGGCCC GATCGATGTT 1030       1040       1050       1060       1070       1080
TTCCTGTGCC CTGAGGAGAC CGTAGGTGGG ATCAGCCCTG GGAAGACCCC ATCCCAGGAG 1090       1100       1110       1120       1130       1140
GTCACTTCTG AGGAGGAGAA CAGGGCCACT GACTCTGCCA CCATAGTGTC ACCACCACCA 1150       1160       1170       1180       1190       1200
TCATCTCCCC CCTCATCCCT CACCACAGAT CCCAGCCAGT CTCTACTCAG CCTGGAGCAA 1210       1220       1230       1240       1250       1260
GAACCGCTGT TGTCCCGGAT GGGCAGCCTG CGGGCTCCCG TGGACGAGGA CCGGCCTGTC
```

FIG. 1B-2.

```
     1270       1280       1290       1300       1310       1320
CCGCTGGTGG CGGCCGACTC GCTCCTGGAG CATGTGCGGG AGGACTTCTC CGGCCTCCTC 1330       1340       1350       1360       1370       1380
CCTGAGGAGT TCATCAGCCT TTCCCCACCC CACGAGGCCC TCGACTACCA CTTCGGCCTC 1390       1400       1410       1420       1430       1440
GAGGAGGGCG AGGGCATCAG AGACCTCTTC GACTGTGACT TTGGGGACCT CACCCCCCTG 1450       1460       1470       1480       1490       1500
GATTTCTGAC AGGGCTTGGA GGGACCAGGG TTTCCAGAGT AGCTCACCTT GTCTCTGCAG 1510       1520       1530       1540       1550       1560
CCCTGGAGCC CCCTGTCCCT GGCCGTCCTC CCAGCCTGTT TGGAAACATT TAATTTATAC 1570       1580       1590       1600       1610       1620
CCCTCTCCTC TGTCTCCAGA AGCTTCTAGC TCTGGGGTCT GGCTACCGCT AGGAGGCTGA 1630       1640       1650       1660       1670       1680
GCAAGCCAGG AAGGGAAGGA GTCTGTGTGG TGTGTATGTG CATGCAGCCT ACACCCACAC 1690       1700       1710       1720       1730       1740
GTGTGTACCG GGGGTGAATG TGTGTGAGCA TGTGTGTGTG CATGTACCGG GGAATGAAGG 1750       1760       1770       1780       1790       1800
TGAACATACA CCTCTGTGTG TGCACTGCAG ACACGCCCCA GTGTGTCCAC ATGTGTGTGC 1810       1820       1830       1840       1850       1860
ATGAGTCCAT CTCTGCGCGT GGGGGGGCTC TAACTGCACT TTCGCCCTT TTGCTCGTGG 1870       1880       1890       1900       1910       1920
GGTCCCACAA GGCCCAGGGC AGTGCCTGCT CCCAGAATCT GGTGCTCTGA CCAGGCCAGG
```

FIG. 1B-3.

```
     1930       1940       1950       1960       1970       1980
TGGGGAGGCT TTGGCTGGCT GGGCGTGTAG GACGGTGAGA GCACTTCTGT CTTAAAGGTT 1990       2000       2010       2020       2030       2040
TTTCTGATT  GAAGCTTAA  TGGAGCGTTA TTTATTTATC GAGGCCTCTT TGGTGAGCCT 2050       2060       2070       2080       2090       2100
GGGGAATCAG CAAAAGGGGA GGAGGGGTGT GGGGTTGATA CCCCAACTCC CTCTACCCTT 2110       2120       2130       2140       2150       2160
GAGCAAGGGC AGGGGTCCCT GAGCTGTTCT TCTGCCCCAT ACTGAAGGAA CTGAGGCCTG 2170       2180       2190       2200       2210       2220
GGTGATTTAT TTATTGGGAA AGTGAGGGAG GGAGACAGAC TGACTGACAG CCATGGGTGG 2230       2240       2250       2260       2270       2280
TCAGATGGTG GGGTGGGCCC TCTCCAGGGG GCCAGTTCAG GGCCCAGCTG CCCCCAGGA 2290       2300       2310       2320       2330       2340
TGGATATGAG ATGGGAGAGG TGAGTGGGGG ACCTTCACTG ATGTGGGCAG GAGGGGTGGT 2350       2360       2370       2380       2390       2400
GAAGGCCTCC CCCAGCCCAG ACCCTGTGGT CCCTCCTGCA GTGTCTGAAG CGCCTGCCTC 2410       2420       2430       2440       2450       2460
CCCACTGCTC TGCCCCACCC TCCAATCTGC ACTTTGATTT GCTTCCTAAC AGCTCTGTTC 2470       2480       2490       2500       2520       2520
CCTCCTGCTT TGTTTTAAT  AAATATTTTG ATGACGTTAA AAAAAGGAAT TCGATAT
```

FIG. 1B-4.

```
   1  ttccgttttt  tctcagggga  cgttgaaatt  atttttgtaa  cgggagtcgg  gagaggacgg
  61  ggcgtgcccc  gcgtgcgcgc  gcgtcgtcct  ccccggcgct  cctccacagc  tcgctggctc
 121  ccgccgcgga  aaggcgtcat  gccgcccaaa  accccccgaa  aaacggccgc  caccgccgcc
 181  gctgccgccg  cggaacccgc  cggacacgcg  caggacagcg  cgccggagga  cctgcctctc  ggcgcgccc   ctcctgagga  ggacccagag
 241  caggacagcg  gccccggagga cctgcctctc  gtcaggcttg  agtttgaaga  aacagaagaa
 301  cctgatttta  ctgcattatg  tcagaaatta  aagataccag  atcatgtcag  agagagagct
 361  tggttaactt  gggagaaagt  ttcatctgtg  gatggagtat  tgggaggtta  tattcaaaag
 421  aaaaaggaac  tgtggggaat  ctgtatcttt  attgcagcag  ttgacctaga  tgagatgtcg
 481  ttcactttta  ctgagctaca  gaaaaacata  gaaatcagtg  tccataaatt  ctttaactta
 541  ctaaaagaaa  ttgataccag  taccaaagtt  gataatgcta  tgtcaagact  gttgaagaag
 601  tatgatgtat  tgtttgcact  cttcagcaaa  ttggaaagga  catgtgaact  tatatatttg
 661  acacaaccca  gcagttcgat  atctactgaa  ataaattctg  cattggtgct  aaaagttttct
 721  tggatcacat  ttttattagc  gtattacaaa  tggaagatga  tctggtgatt
 781  tcatttcagt  taatgctatg  tgtccttgac  tattttatta  aactctcacc  tcccatgttg
 841  ctcaaagaac  catataaaac  agctgttata  cccattaatg  gttcactcg   aacacccagg
 901  cgaggtcaga  acaggagtgc  acggatagca  aaacaactag  aaaatgatac  aagaattatt
 961  gaagttctct  gtaaagaaca  tgaatgtaat  atagatgagg  tgaaaaatgt  ttatttcaaa
1021  aattttatac  cttttatgaa  ttctcttgga  cttgtaacat  ctaatggact  tccagaggtt
1081  gaaaatcttt  ctaaacgata  cgaagaaatt  tatcttaaaa  ataaagatct  agatgcaaga
1141  ttattttttgg atcatgataa  aactcttcag  cctgatgaa   gaggtgaatg  tagacagttt
1201  agaacaccac  gaaaaagtaa  aactcttcag  cctgatgaa   gaggtgaatg  tagacagttt
1261  gttaggactg  ttatgaacac  tatccaacaa  ttaatgatga  tttaaattc   agcaagtgat
1321  caaccttcag  aaaatctgat  ttcctatttt  accaactgca  cagtgaatcc  aaaagaaagt
1381  atactgaaaa  gagtgaagga  tataggatac  atcttttaaag  agaaatttgc  taaagctgtg
1441  ggacagggtt  gtgtcgaaat  tggatcacag  cgatcacag   ttggagttcg  cttgtattac
```

FIG. 2A-1.

```
1501 cgagtaatgg aatccatgct taaaccagaa gaagaacgat tatccattca aaattttagc
1561 aaacttctga atgacaacat tttcatatg tctttattgg cgtgcgctct tgaggttgta
1621 atggccacat atagcagaag tacatctcag aatcttgatt ctggaacaga tttgtctttc
1681 ccatggattc tgaatgtgct taatttaaaa gcctttgatt tttacaaagt gatcgaaagt
1741 tttatcaaag cagaaggcaa cttgacaaga gaaatgataa aacatttaga acgatgtgaa
1801 catcgaatca tggaatccct tgcatggctc tcagattcac ctttatttga tcttattaaa
1861 caatcaaagg accgagaagg accaactgat caccttgaat ctgcttgtcc tcttaatctt
1921 cctctccaga ataatcacac tgcagcagat atgtatcttt ctcctgtaag atctccaaag
1981 aaaaaaggtt caactacgcg tgtaaattct actgcaaatg cagagacaca agcaacctca
2041 gccttccaga cccagaagcc attgaaatct acctctcttt cactgttta taaaaaagtg
2101 tatcggctag cctatctccg gctaaataca cttgtgaac gccttctgtc tgagcaccca
2161 gaattagaac atatcatctg gacccttttc cagcacaccc tgcagaatga gtatgaactc
2221 atgagagaca ggcatttgga ccaaattatg atgtgttcca tgtatggcat atgcaaagtg
2281 aagaatatag accttaaatt caaaatcatt gtaacagcat acaaggatct tcctcatgct
2341 gttcaggaga cattcaaacg tgttttgatc aaagaagagg agtatgattc tattatagta
2401 ttctatataact cggtcttcat gcagagactg tttgcagta tttgcagta tgcttccacc
2461 aggcccccta cctgtcacc aatacctcac attcctcgaa gccattacaa gtttcctagt
2521 tcacccttac ggattcctgg agggaacatc tatatttcac cctgaagag tccatataaa
2581 atttcagaag gtctgccaac accaacaaaa atgactccaa gatcaagaat cttagtatca
2641 attggtgaat cattcgggac ttctgagaag ttccagaaaa taaatcagat ggtatgtaac
2701 agcgaccgtg tgctcaaaag aagtgctgaa ggaagcaacc ctcctaaacc actgaaaaaa
2761 ctacgctttg atattgaagg atcagatgaa gcagatggaa gtaaacatct cccaggagag
2821 tccaaatttc agcagaaact ggcagaaatt tacctcaaac gaacacgaat gcaaaagcag
2881 aaaatgaatg atagcatgg tacctcaaac aatgaggatc tcaggaccct
2941 ggtggacact gtgtacacct ctgattcat tgtctctcac agatgtgact gtat
```

FIG. 2A-2.

"MPPKTPRKTAATAAAAAEPPAPPPPPEEDPEQDSGPEDLPL
VRLEFEETEEPDFTALCQKLKIPDHVRERAWLTWEKVSSVDGVLGGYIQKKELWGIC
IFIAAVDLDEMSFTFTELQKNIEISVHKFFNLLKEIDTSTKVDNAMSRLLKKYDVLFA
LFSKLERTCELIYLTQPSSSISTEINSALVLKVSWITFLLAKGEVLQMEDDLVISFQL
MLCVLDYFIKLSPPMLLKEPYKTAVIPINGSPRTPRRGQNRSARIAKQLENDTRIIEV
LCKEHECNIDEVKNVYFKNFIPFMNSLGLVTSNGLPEVENLSKRYEEIYLKNKDLDAR
LFLDHDKTLQTDSIDSFETQRTPRKSNLDEEVNVIPPHTPVRTVMNTIQQLMILNSA
SDQPSENLISYFNNCTVNPKESILKRVKDIGYIFKEKFAKAVGQGCVEIGSQRYKLGV
RLYYRVMESMLKSEERLSIQNFSKLLNDNIFHMSLLACALEVVMATYSRSTSQNLDS
GTDLSFPWILNVLNLKAFDFYKVIESFIKAEGNLTREMIKHLERCEHRIMESLAWLSD
SPLFDLIKQSKDREGPTDHLESACPLNLPLQNNHTAADMYLSPVRSPKKKGSTTRVNS
TANAETQATSAFQTQKPLKSTSLSLFYKKVYRLAYLRLNTLCERLLSEHPELEHIIWT
LFQHTLQNEYELMRDRHLDQIMMCSMYGICKVKNIDLKFKIIVTAYKDLPHAVQETFK
RVLIKEEEYDSIIVFYNSVFMQRLKTNILQYASTRPPTLSPIPHIPRSPYKFPSSPLR
IPGGNIYISPLKSPYKISEGLPTPTKMTPRSRILVSIGESFGTSEKFQKINQMVCNSD
RVLKRSAEGSNPPKPLKKLRFDIEGSDEADGSKHLPGESKFQQKLAEMTSTRTRMQKQ
KMNDSMDTSNKEEK"

FIG. 2B.

```
                                                      >HincII
                                       >AccI            |---|
                                       |---|            |---|
                         >BglII        >SalI            |---|
         *   |---|  *         *         |---|   *         *         *
             10           20           30           40           50           60
         *         *         *         *         *         *
GACGGATCGG GAGATCTCCC GATCCCCTAT GGTCGACTCT CAGTACAATC TGCTCTGATG >AlwNI
                                  |---|
         *         *         *         *         *         *
             70           80           90          100          110          120
         *         *         *         *         *         *
CCGCATAGTT AAGCCAGTAT CTGCTCCCTG CTTGTGTGTT GGAGGTCGCT GAGTAGTGCG >ApoI                                    >MfeI
    |---|                                    |---|
    |130|    *         *         *         *         *
         *         *         *    140       150  160           170          180
         *         *         *         *         *         *
CGAGCAAAAT TTAAGCTACA ACAAGGCAAG GCTTGACCGA CAATTGCATG AAGAATCTGC >HincII
                                              >AflIII         |---|
                           >NruI              |---|           |---|
                           |---|              >MluI           |---|
                           |210|    *         |230|    *
         *         *         *    220           *         *
             190          200          *         *
         *         *         *         *         *         *
TTAGGGTTAG GCGTTTTGCG CTGCTTCG CGA TGT ACG GGC CAG ATA TAC GCG TTG
                                 Arg Cys Thr Gly Gln Ile Tyr Ala Leu>
                     d_____d____ CMV PROMOTER _____d_____d_____>

```
                        >SpeI         >AseI
        240            250           260           270           280
         *              *             *             *             *
    ACA TTG ATT ATT GAC TAG TTA ATA GTA ATC AAT TAC GGG GTC ATT
    Thr Leu Ile Ile Asp *** Leu Leu Ile Val Ile Asn Tyr Gly Val Ile>
    |__d___d___d___d___d__|  |__d___d___d___d___d___d___d___d___d__|
                             |_CMV PROMOTER_____|

290            300           310           320           330
         *              *             *             *             *
    AGT TCA TAG CCC ATA TAT GGA GTT CCG CGT TAC ATA ACT TAC GGT AAA
    Ser Ser *** Pro Ile Tyr Gly Val Pro Arg Tyr Ile Thr Tyr Gly Lys>
    |__d___d__|  |__d___d___d___d___d___d___d___d___d___d___d___d__|
                 |_CMV PROMOTER_____|

>BglI                                            >AatII
              |                                                 |
        340            350           360           370           380
         *              *             *             *             *
    TGG CCC GCC TGG CTG ACC GCC CAA CGA CCC CCG CCC ATT GAC GTC AAT
    Trp Pro Ala Trp Leu Thr Ala Gln Arg Pro Pro Pro Ile Asp Val Asn>
    |__d___d___d___d___d___d___d___d___d___d___d___d___d___d___d___d__|
    |_CMV PROMOTER_____|

390            400           410           420
         *              *             *             *
    AAT GAC GTA TGT TCC CAT AGT AAC GCC AAT AGG GAC TTT CCA TTG ACG
    Asn Asp Val Cys Ser His Ser Asn Ala Asn Arg Asp Phe Pro Leu Thr>
    |__d___d___d___d___d___d___d___d___d___d___d___d___d___d___d___d__|
    |_CMV PROMOTER_____|
```

```
>AatII
   430            440            450            460            470
    |*             *              *              *              *
TCA ATG GGT GGA CTA TTT ACG GTA AAC TGC CCA CTT GGC AGT ACA TCA
Ser Met Gly Gly Leu Phe Thr Val Asn Cys Pro Leu Gly Ser Thr Ser>
  d    d    d    d   d_CMV PROMOTER   d    d    d    d    d    d

>NdeI                               >AatII
                      |--|
   480            490            500            510            520
    *              *              *             |*|             *
AGT GTA TCA TAT GCC AAG TAC GCC CCC TAT TGA CGT CAA TGA CGG TAA
Ser Val Ser Tyr Ala Lys Tyr Ala Pro Tyr *** Arg Gln *** Arg ***>
  d    d    d    d    d    d    d_CMV PROMOTER   d    d    d    d

>BglI
          |--|
   530            540            550            560            570
    *              *              *              *              *
ATG GCC CGC CTG GCA TTA TGC CCA GTA CAT GAC CTT ATG GGA CTT TCC
Met Ala Arg Leu Ala Leu Cys Pro Val His Asp Leu Met Gly Leu Ser>
                            >BsaAI           >NcoI
                            |--|             |--|
                            >SnaBI           >StyI   >MslI
                            |----|           |------|
   580            590            600            610
    *              *              *             |*|  |--*
TAC TTG GCA GTA CAT CTA CGT ATT AGT CAT CGC TAT TAC CAT GGT GAT
Tyr Leu Ala Val His Leu Arg Ile Ser His Arg Tyr Tyr His Gly Asp>
  d    d    d    d    d_CMV PROMOTER   d    d    d    d    d    d
```

FIG. 4-3.

```
     620         630         640         650         660
      *           *           *           *           *
GCG GTT TTG GCA GTA CAT CAA TGG GCG TGG ATA GCG GTT TGA CTC ACG
Ala Val Leu Ala Val His Gln Trp Ala Trp Ile Ala Val *** Leu Thr>
|___d___|___d___|___d___|___d___|___d___|___d_CMV PROMOTER___d___|
                                                           >BanI
                                      >AatII                ——— *
                                      ——— *
     670         680         690         700         710
      *           *           *           *           *
GGG ATT TCC AAG TCT CCA CCC CAT TGA CGT CAA TGG GAG TTT GTT TTG
Gly Ile Ser Lys Ser Pro Pro His *** Arg Gln Trp Glu Phe Val Leu>
|___d___|___d___|___d___|___d___|___d___|___d_CMV PROMOTER___d___|

720         730         740         750         760
      *           *           *           *           *
GCA CCA AAA TCA ACG GGA CTT TCC AAA ATG TCG TAA CAA CTC CGC CCC
Ala Pro Lys Ser Thr Gly Leu Ser Lys Met Ser *** Gln Leu Arg Pro>
|___d___|___d___|___d___|___d___|___d___|___d_CMV PROMOTER___d_-d___|

770         780         790         800         810
      *           *           *           *           *
ATT GAC GCA AAT GGG CGG TAG GCG TGT ACG GTG GGA GGT CTA TAT AAG
Ile Asp Ala Asn Gly Arg *** Ala Cys Thr Val Gly Gly Leu Tyr Lys>
|___d___|___d___|___d___|___d___|___d___|___d_CMV PROMOTER___d___|
```

FIG. 4-4.

```
>BanII
 ->Sacl
  ->BsiHKAI
   ->Ecl136II
   *|    820        830        840        850
    |     *          *          *          *
   CAG AGC TCT CTG GCT AAC TAG AGA ACC CAC TGC TTA CTG GCT TAT CGA
   Gln Ser Ser Leu Ala Asn *** Arg Thr His Cys Leu Leu Ala Tyr Arg>
    d___d___d___d___d_CMV PROMOTER_d___d___d___d___d >BsaI                      >KpnI
              ->SfcI                     ->Acc65I
               *         *         *      ->BanI
              870       880       890    *|  900       910
               *         *         *      |   *         *
                                         >HindIII
>AseI
 ->T7_PROMOTER
  *|  860
   |   *
  AAT T AATACGA CTCACTATAG GGAGACCCAA GCTTCGGCGG GGTACCACTC
  Asn Xxx>
    d_>

```
                1210       1220       1230       1240       1250       1260
                  *          *          *          *          *          *
          GTTGTTTGCC CCTCCCCCGT GCCTTCCTTG ACCCTGGAAG GTGCCACTCC CACTGTCCTT

>BanI
                                                |
                1270       1280       1290       1300       1310       1320
                  *          *          *          *          *          *
          TCCTAATAAA ATGAGGAAAT TGCATCGCAT TGTCTGAGTA GGTGTCATTC TATTCTGGGG

>BbsI
                                                                  |
                1330       1340       1350       1360       1370       1380
                  *          *          *          *          *          *
          GGTGGGGTGG GGCAGGACAG CAAGGGGGAG GATTGGGAAG ACAATAGCCG AAATGACCGA

>BssSI
                                |
                              >BspMI
                                |
                1390       1400       1410       1420       1430       1440
                  *          *          *          *          *          *
          CCAAGCGACG CCCAACCTGC CATCACGAGA TTTCGATTCC ACCGCCGCCT TCTATGAAAG

>NaeI
                                                |
                                              >BsrFI
                                                |
                                              >BpmI|
                                                |
                                              >NgoMI
                                                |
                1450       1460       1470       1480       1490       1500
                  *          *          *          *          *          *
          GTTGGGCTTC GGAATCGTTT TCCGGGACGC CGGCTGGATG ATCCTCCAGC GCGGGGATCT
```

FIG. 4-8.

```
                    >BpmI
                      |
          >SV40_early_poly_A
           |
     1510       1520     |1530      1540      1550      1560
      *    *    *    *    *|   *    *    *    *    *    *    *
CATGCTGGAG TTCTTCGCCC ACCCCAACTT GTTATTGCA GCTTATAATG GTTACAAATA >ApoI                            >BsmI
                    |                                |
     1570       1580|    1590      1600         1610|    1620
      *    *    *   |*    *    *    *    *    *    |*    *    *
AAGCAATAGC ATCACAAATT TCACAAATAA AGCATTTTT TCACTGCATT CTAGTTGTGG >HincII
                                        |
                         >Bst1107I     >AccI
                             |          |
                             |   >AccI  | >SalI
                             |    |     |  |
     1630       1640     1650|    |1660 |  |1670      1680
      *    *    *    *    * |*  * |*    *|*||*  *    *    *    ^
TTTGTCCAAA CTCATCAATG TATCTTATCA TGTCTGTATA CCGTCGACCT CTAGCTAGAG
                                                                ___

>BsrBI
                                                          |
     1690       1700      1710      1720           1730|     1740
      *    *    *    *    *    *    *    *    *    *  |*    *    ^
CTTGGGCGTAA TCATGGTCAT AGCTGTTTCC TGTGTGAAAT TGTTATCCGC TCACAATTCC
___C                                                               C___
    PUC19 BACKBONE H3 TO AATII

FIG. 4-9.
```

```
                1750           1760           1770           1780           1790           1800
                  *              *              *              *              *              *
        ACACAACATA CGAGCCGGAA GCATAAAGTG TAAAGCCTGG GGTGCCTAAT GAGTGAGCTA >
                  C                                                                           C
        |_____PUC19 BACKBONE H3 TO AATII_____|          |_____>BanI_____|

>AseI
         |--|
                1810           1820           1830           1840           1850           1860
                  *              *              *              *              *              *
        ACTCCACATTA ATTGCGTTGC GCTCACTGCC CGCTTTCCAG TCGGGAAACC TGTCGTGCCA >
                  C                                                                           C
        |_____PUC19 BACKBONE H3 TO AATII_____|

>PvuII
   |--|
  >MspA1I >AseI        >EaeI
   |---|  |--|         |--|
                1870           1880           1890           1900           1910           1920
                  *              *              *              *              *              *
        GCTGCATTAA TGAATCGGCC AACGGCGGGG GAGAGGCGGT TTGCGTATTG GGCGCTCTTC >
                  C                                                                           C
        |_____PUC19 BACKBONE H3 TO AATII_____|                         |___>HaeII___|

>EarI
   |--|
  >SapI                               >BsiEI        >BsrBI
   |---|                              |---|         |---|
                1930           1940           1950           1960           1970           1980
                  *              *              *              *              *              *
        CGCTTCCCTCG CTCACTGACT CGCTGCGCTC GGTCGTTCGG CTGCGGCGAG CGGTATCAGC >
                  C                                                                           C
        |_____PUC19 BACKBONE H3 TO AATII_____|
```

FIG. 4-10.

```
        1990       2000       2010       2020       2030         >AflIII
          *          *          *          *          *          | 2040
TCACTCAAAG GCGGTAATAC GGTTATCCAC AGAATCAGGG GATAACGCAG GAAAGAACAT
         c                                                      c
         pUC19 BACKBONE H3 TO AATII 2050       2060       2070       2080       2090       2100
          *          *          *          *          *          *
GTGAGCAAAA GGCCAGCAAA AGGCCAGGAA CCGTAAAAAG GCCGCGTTGC TGGCGTTTTT
         c                                                      c
         pUC19 BACKBONE H3 TO AATII 2110       2120       2130       2140     >DrdI 2150       2160
          *          *          *          *        |   *          *
CCATAGGCTC CGCCCCCCTG ACGAGCATCA CAAAAATCGA CGCTCAAGTC AGAGGTGGCG
         c                                                      c
         pUC19 BACKBONE H3 TO AATII 2170       2180       2190       2200    >BssSI 2210       2220
          *          *          *          *        |   *          *
AAACCCGACA GGACTATAAA GATACCAGGC GTTTCCCCCT GGAAGCTCCC TCGTGCGCTC
         c                                                      c
         >BsaWI
         |
         pUC19 BACKBONE H3 TO AATII 2230       2240       2250       2260       2270       2280
          *          *          *          *          *          *
TCCTGTTCCG ACCCTGCCGC TTACCGGATA CCTGTCCGCC TTTCTCCCTT CGGGAAGCGT
         c                                                      c
         pUC19 BACKBONE H3 TO AATII
```

FIG 4-11.

```
>HaeII      >SfcI
 | 2290       2300        2310        2320        2330        2340
 *    *     *    *     *    *     *    *     *    *     *    *     >
GGCGCTTTCT CAATGCTCAC GCTGTAGTTA TCTCAGTTCG GTGTAGGTCG TTCGCTCCAA
─────────────────────────────────────────────────────────────────
               pUC19 BACKBONE H3 TO AATII                       c

>MspAlI
       >BsiHKAI         |    >BsaWI
       >ApaLI           |  >BsiEI  |
       |    |           |   |   |  |
    2350    2360        2370    2380    2390    2400
     *    *     *    *     *    *     *    *     *    *     >
GCTGGGGCTGT GTGCACGAAC CCCCCGTTCA GCCCGACCGC TGCGCCTTAT CCGGTAACTA
─────────────────────────────────────────────────────────────────
               pUC19 BACKBONE H3 TO AATII                       c

>AlwNI
                                                   |
    2410        2420        2430        2440        2450        2460
     *    *     *    *     *    *     *    *     *    *     *    *     >
TCGTCTTGAG TCCAACCCGG TAAGACACGA CTTATCGCCA CTGGCAGCAG CCACTGGTAA
─────────────────────────────────────────────────────────────────

>SfcI
                     |
    2470        2480        2490        2500        2510        2520
     *    *     *    *     *    *     *    *     *    *     *    *     >
CAGGATTAGC AGAGCGAGGT ATGTAGGCGG TGCTACAGAG TTCTTGAAGT GGTGGCCTAA
─────────────────────────────────────────────────────────────────
               pUC19 BACKBONE H3 TO AATII                       c
```

FIG. 4-12.

```
              2530         2540         2550         2560         2570         2580
                *            *            *            *            *            *
         CTACGGCTAC ACTAGAAGGA CAGTATTTGG TATCTGCGCT CTGCTGAAGC CAGTTACCTT
         ─────────────────────────────────────────────────────────────────>
                              PUC19 BACKBONE H3 TO AATII
         >Eco57I
         ──|
           |2590         2600         2610         2620         2630         2640
            *             *            *            *           |*            *
         CGGAAAAAGA GTTGGTAGCT CTTGATCCGG CAAACAAACC ACCGCTGGTA GCGGTGGTTT
         ─────────────────────────────────────────────────────────────────>
                              PUC19 BACKBONE H3 TO AATII
                                                                >MspAlI
                                                                ──|

2650         2660         2670         2680         2690         2700
                *            *            *            *            *            *
         TTTGTTTGC AAGCAGCAGA TTACGCGCAG AAAAAAAGGA TCTCAAGAAG ATCCTTTGAT
         ─────────────────────────────────────────────────────────────────>
                              PUC19 BACKBONE H3 TO AATII 2710         2720         2730         2740         2750         2760
                *            *            *            *            *            *
         CTTTTCTACG GGGTCTGACG CTCAGTGGAA CGAAAACTCA CGTTAAGGGA TTTTGGTCAT
         ─────────────────────────────────────────────────────────────────>
                              PUC19 BACKBONE H3 TO AATII
                                                                     >BspHI
                                                                     ──|

2770         2780        |2800         2740         2810         2820
                *            *          *|*            *             *            *
         GAGATTATCA AAAAGGATCT TCACCTAGAT CCTTTTAAAT TAAAAATGAA GTTTTAAATC
         ─────────────────────────────────────────────────────────────────>
                              PUC19 BACKBONE H3 TO AATII
                                    >DraI              >DraI
                                    ──|                ──|
```

FIG. 4-13.

```
                                                                              >BanI
                                                                               |
       2830        2840        2850        2860        2870        2880
        *           *           *           *           *           *
AATCTAAAGT ATATATGAGT AAACTTGGTC TGACAGTTAC CAATGCTTAA TCAGTGAGGC
           ─────────────────────────────────────────         ──────────────
              pUC19 BACKBONE H3 TO AATII                        AMP-ORF
                       a                                         c
                                        >AhdI
                                         |
       2890        2900        2910        2920        2930        2940
        *           *           *           *           *           *
ACCTATCTCA GCGATCTGTC TATTTCGTTC ATCCATAGTT GCCTGACTCC CCGTCGTGTA
           ─────────────         ─────────────────────────────────────────
              AMP-ORF                    a
    a                                                                     ^
    c                                                                     ^
           pUC19 BACKBONE H3 TO AATII

>BsaI
                                               |
                                                        >BsrDI    >BpmI
                                                         |         |
       2950        2960        2970        2980        2990        3000
        *           *           *           *           *           *
GATAACTACG ATACGGGAGG GCTTACCATC TGGCCCCAGT GCTGCAATGA TACCGGAGA
           ─────────────────────────────────────────────────────
                                 AMP-ORF                        a
    a                                                                     ^
    c                                                                     ^
           pUC19 BACKBONE H3 TO AATII

>BsrFI                                                       >BGlI
   |                                                            |
       3010        3020        3030        3040        3050        3060
        *           *           *           *           *           *
CCCACGCTCA CCGGCTCCAG ATTATCAGC AATAAACCAG CCAGCCGGAA GGGCCGAGCG
           ─────────────────────────────────────────         ──────────────
                                 AMP-ORF                        a
    a                                                                     ^
    c                                                                     ^
           pUC19 BACKBONE H3 TO AATII
```

*FIG. 4-14.*

```
              3070           3080           3090           3100           3110           3120
               *              *              *              *              *              *
        CAGAAGTGGT CCTGCAACTT TATCCGCCTC CATCCAGTCT ATTAATTGTT GCCGGGAAGC
                                                        -----------
                                                          >AseI
        ---------- ---------- ---------- ----------a---------- ----------
        a
        c---------- ---------- ---------- ---------- ----------a---------- c
              PUC19 BACKBONE H3 TO AATII
                    AMP-ORF
                                           >PspI406I
                                  >FspI            >BsrDl  >SfcI
              3130           3140           3150           3160           3170           3180
               *              *              *              *              *              *
        TAGAGTAAGT AGTTCGCCAG TTAATAGTTT GCGCAACGTT GTTGCCATTG CTACAGGCAT
                                                   ------     -------
        ---------- ---------- ---------- ----------a---------- ----------
        a
        c---------- ---------- ---------- ---------- ----------a---------- c
              PUC19 BACKBONE H3 TO AATII
                    AMP-ORF
        >MslI                                          >BsaWI
              3190           3200           3210           3220           3230           3240
               *              *              *              *              *              *
        CGTGGTGTCA CGCTCGTCGT TTGGTATGGC TTCATTCAGC TCCGGTTCCC AACGATCAAG
        -----                                             ------
        ---------- ---------- ---------- ---------- ----------a---------- ----------
        a
        c---------- ---------- ---------- ---------- ----------a---------- c
              PUC19 BACKBONE H3 TO AATII
```

FIG. 4-15.

```
            3250        3260        3270        3280        3290        3300
              *           *           *           *           *           *
         GCGAGTTACA TGATCCCCCA TGTTGTGCAA AAAAGCGGTT AGCTCCTTCG GTCCTCCGAT         >PvuI
                a                                                                  -
                c                                                                  >BsiEI
              ——————————————————————————————————————————————————————————           -
                            AMP-ORF
              ——————————————————————————————————————————————————————————
                        PUC19 BACKBONE H3 TO AATII

>EaeI                   >MslI
            3310        3320        3330        3340        3350        3360
              *           *|          *           *           *|          *
         CGTTGTCAGA AGTAAGTTGG CCGCAGTGTT ATCACTCATG GTTATGGCAG CACTGCATAA
                a                                                 a
                c                                                 c
              ——————————————————————————————————————————————————————————
                            AMP-ORF
              ——————————————————————————————————————————————————————————
                        PUC19 BACKBONE H3 TO AATII

>ScaI
            3370        3380        3390        3400        3410        3420
              *           *           *           *           *|          *
         TTCTCTTACT GTCATGCCAT CCGTAAGATG CTTTTCTGTG ACTGGTGAGT ACTCAACCAA
                a                                                 a
                c                                                 c
              ——————————————————————————————————————————————————————————
                            AMP-ORF
              ——————————————————————————————————————————————————————————
                        PUC19 BACKBONE H3 TO AATII

>BsiEI
            3430        3440        3450        3460        3470        3480
              *           *           *|          *           *           *
         GTCATTCTGA GAATAGTGTA TGCGGCGACC GAGTTGCTCT TGCCCGGCGT CAATACGGGA
                a                                                 a
                c                                                 c
              ——————————————————————————————————————————————————————————
                            AMP-ORF
              ——————————————————————————————————————————————————————————
                        PUC19 BACKBONE H3 TO AATII
```

FIG. 4-16.

```
                              >XmnI
          >DraI    >BsiHKAI      >Psp1406I
           |          |           |
  3490     |  3500    |  3510     | 3520           3530              3540
     *     |     *    |    *      |    *       *    |    *       *     |    >
TAATACCGGG CCACATAGCA GAACTTTAAA AGTGCTCATC ATTGGAAAAC GTTCTTCGGG
              a                                   a                   >
              c          PUC19 BACKBONE H3 TO AATII                   >
                            AMP-ORF

>Eco57I
                                                                   |
                                                                   |  >ApaLI
                                                                   |   |
                                                                   |   |  >BssSI
                                                                   |   |   |
  3550        3560       3570       3580       3590        3600
     *     *     |    *       *    |    *       *    |    *   |   *
GCGAAAACTC TCAAGGATCT TACCGCTGTT GAGATCCAGT TCGATGTAAC CCACTCGTGC
              a                                   a                   >
              c          PUC19 BACKBONE H3 TO AATII                   >
                            AMP-ORF
           >MspAlI 3610        3620       3630       3640       3650        3660
     *     *        *       *           *       *        *       *     >
ACCCAACTGA TCTTCAGCAT CTTTTACTTT CACCAGCGTT TCTGGGTGAG CAAAAACAGG
              a                                   a                   >
              c          PUC19 BACKBONE H3 TO AATII                   >
                            AMP-ORF
>BsiHKAI
```

FIG. 4-17.

```
       3670        3680        3690        3700        3710        3720
        *           *           *           *           *           *
AAGGCAAAAAT GCCGCAAAAA AGGGAATAAG GGCGACACGG AAATGTTGAA TACTCATACT
         a                          AMP-ORF                     a
         c  PUC19 BACKBONE H3 TO AATII                          c

>EarI    >SspI                                    >BspHI    >BsrBI
    | 3730   | *                                      |  3770   |
    |  *     |              3750        3760          |   *     |
CTTCCTTTTT CAATATTATT GAAGCATTTA TCAGGGTTAT TGTCTCATGA GCGGATACAT
    c              PUC19 BACKBONE H3 TO AATII                  c 3790        3800        3810        3820        3830        3840
        *           *           *           *           *           *
ATTTGAATGT ATTTAGAAAA ATAAACAAAT AGGGGTTCCG CGCACATTTC CCCGAAAAGT
         c              PUC19 BACKBONE H3 TO AATII              c

>HincII
  |
  >AccI
  ||
  >AatII
  |||
   >SalI
   ||||
       3850
        *
GCCACCTGAC GTC
         c
```

FIG. 4-18.

```
                                         >HincII
                                            ------
                                         >AccI
                                            ---
                                         >SalI
>BglII                                     ---
    ---
    *        *        *        *        *        *
    10       20       30       40       50       60
GACGGATCGG GAGATCTCCC GATCCCCTAT GGTCGACTCT CAGTACAAATC TGCTCTGATG >AlwNI
              ---
    *        *        *        *        *        *
    70       80       90       100      110      120
CCGCATAGTT AAGCCAGTAT CTGCTCCCTG CTTGTGTGTT GGAGGTCGCT GAGTAGTGCG >MfeI
                                     ---
    *        *        *        *        *        *
    130      140      150      160      170      180
CGAGCAAAAT TTAAGCTACA ACAAGGCAAG GCTTGACCGA CAATTGCATG AAGAATCTGC >NruI
               ---                                        >HincII
                                                            ------
                                                         >AflIII
                                                             ---
                                                         >MluI
                                                             ---
    *        *        *        *        *
    190      200      210      220      230
TTAGGGTTAG GCGTTTTGCG CTGCTTCG CGA TGT ACG GGC CAG ATA TAC GCG TTG
                                Arg Cys Thr Gly Gln Ile Tyr Ala Leu>
                   e_____e_____CMV PROMOTER_____e_____e
```

FIG. 6-1.

```
                     >SpeI          >AseI
       240            250             260             270             280
        *              *               *               *               *
ACA TTG ATT ATT GAC TAG TTA ATA GTA ATC AAT TAC GGG GTC ATT
Thr Leu Ile Ile Asp *** Leu Leu Val Ile Asn Tyr Gly Val Ile>
  e       e       e       e_CMV PROMOTER_e       e       e       >

290             300             310             320             330
        *               *               *               *               *
AGT TCA TAG CCC ATA TAT GGA GTT CCG CGT TAC ATA ACT TAC GGT AAA
Ser Ser *** Pro Ile Tyr Gly Val Pro Arg Tyr Ile Thr Tyr Gly Lys>
  e       e       e_CMV PROMOTER_e       e       e       e       >

>BglI                                        >AatII
             340             350             360             370
              *               *               *               *
TGG CCC GCC TGG CTG ACC GCC CAA CGA CCC CCG CCC ATT GAC GTC AAT
Trp Pro Ala Trp Leu Thr Ala Gln Arg Pro Pro Pro Ile Asp Val Asn>
  e       e       e       e_CMV PROMOTER_e       e       e       >

380             390             400             410             420
   *               *               *               *               *
AAT GAC GTA TGT TCC CAT AGT AAC GCC AAT AGG GAC TTT CCA TTG ACG
Asn Asp Val Cys Ser His Ser Asn Ala Asn Arg Asp Phe Pro Leu Thr>
  e       e       e       e       e       e       e       e       >
```

FIG. 6-2.

```
>AatII
 —
430          440          450          460          470
 *|    *      *      *      *      *      *      *      *|
TCA ATG GGT GGA CTA TTT ACG GTA AAC TGC CCA CTT GGC AGT ACA TCA
Ser Met Gly Gly Leu Phe Thr Val Asn Cys Pro Leu Gly Ser Thr Ser>
 e___e___e___e___e___e_CMV PROMOTER_e___e___e___e___e___e___e___
                            >NdeI                        >BglI
                             —                            —
        480          490          500          510          520
 *      *|   *      *      *      *      *|  *|     *      *
AGT GTA TCA TAT GCC AAG TAC GCC CCC TAT TGA CGT CAA TGA CGG TAA
Ser Val Ser Tyr Ala Lys Tyr Ala Pro Tyr *** Arg Gln *** Arg ***>
 e___e___e___e___e___e___e___e___e_CMV PROMOTER_e___e___e___e___

>BglI                        >BsaAI
 —                            —
                             >SnaBI
                              —
530          540          550          560          570
 *|    *      *      *      *      *      *      *      *|
ATG GCC CGC CTG GCA TTA TGC CCA GTA CAT GAC CTT ATG GGA CTT TCC
Met Ala Arg Leu Ala Leu Cys Pro Val His Asp Leu Met Gly Leu Ser>
 e___e___e___e___e___e___e___e___e___e___e___e___e___e___e___e___

>NcoI
                                            —
                                           >StyI    >MslI
                                            —        —
        580          590          600          610
 *      *      *      *      *      *      *|      *|
TAC TTG GCA GTA CAT CTA CGT ATT AGT CAT CGC TAT TAC CAT GGT GAT
Tyr Leu Ala Val His Leu Arg Ile Ser His Arg Tyr Tyr His Gly Asp>
 e___e___e___e___e___e___e___e___e_CMV PROMOTER_e___e___e___e___
```

FIG 6-3.

```
         620       630       640       650       660
           *         *         *         *         *
         GCG GTT TTG GCA GTA CAT CAA TGG GCG TGG ATA GCG GTT TGA CTC ACG
         Ala Val Leu Ala Val His Gln Trp Ala Trp Ile Ala Val *** Leu Thr>
         |_____e_CMV PROMOTER_e_____e_____e_____|

>AatII                       >BanI
                                    |——|                         |——|*
          670       680       690       700       710
            *         *         *         *         *
         GGG ATT TCC AAG TCT CCA CCC CAT TGA CGT CAA CGT CAA TGG GAG TTT GTT TTG
         Gly Ile Ser Lys Ser Pro Pro His *** Arg Gln Arg Gln Trp Glu Phe Val Leu>
         |_____e_CMV PROMOTER_e_____e_____e_____|

720       730       740       750       760
            *         *         *         *         *
         GCA CCA AAA TCA ACG GGA CTT TCC AAA ATG TCG TAA CAA CTC CGC CCC
         Ala Pro Lys Ser Thr Gly Leu Ser Lys Met Ser *** Gln Leu Arg Pro>
         |_____e_CMV PROMOTER_e_____e_____e_____|

770       780       790       800       810
            *         *         *         *         *
         ATT GAC GCA AAT GGG CGG TAG GCG TGT ACG GTG GGA GGT CTA TAT AAG
         Ile Asp Ala Asn Gly Arg *** Ala Cys Thr Val Gly Gly Leu Tyr Lys>
         |_____e_CMV PROMOTER_e_____e_____e_____|
```

FIG. 6-4.

```
>SacI
   |
   BanII
   |
   >BsiHKAI
   |
>Ecl136II
   |     820             830             840             850
   |      *               *               *               *
CAG AGC TCT CTG GCT AAC TAG AGA ACC CAC TGC TTA CTG GCT TAT CGA
Gln Ser Ser Leu Ala Asn *** Arg Thr His Cys Leu Leu Ala Tyr Arg>
__e_____e_____e_____e_CMV PROMOTER__e_____e_____e_____e__

>BsaI                                >KpnI
                     |                                    |
                    >SfcI                                >Acc65II
                     |                                    |    >BanI
                     |                                    |     |
                        *       *  >HindIII  *       *    *     *
                       880              890             900            910
AAT T AATACGA CTCACTATAG GGAGACCCAA GCTTCGGCG GGTACCACTC
   |
  >AseI
   |
   >T7_PROMOTER
   |      *
  860
   *
Asn Xxx>
   e_>
_____

FIG. 6-5.
```

```
                                                                                >PflMI
                         >EarI                  >PvuII| >BanII
                     |920       930       940       950       960       970
                     *|   *        *        |*       |*        *        *
                 TCTTCCGCAT CGCTGTCTGC GAGGGCCAGC TGTTGGGCTC GCGGTTGAGG ACAAACTCTT
                            f_____
                            f__TRIPARTITE LEADER_____

>EarI           >ScaI
  |970       980       990      1000      1010      1020      1030
  *|   *     |*   *        *        *        *        *        *
 CGCGGTCTTT CCAGTACTCT TGGATCGGAA ACCCGTCGGC CTCCGAACGG TACTCCGCCA
 _____f
 _____TRIPARTITE LEADER_____f

>BsoBI
                    >BsiEI                 >AvaI
>EcoO109I            >BsaWI                 >XhoI
 >PpuMI               |                     >PaeR7I
  |1040      1050      |1060      1070       |1080      1090
  *|   *        *       |*        *          |*        *        *
 CCGAGGGACC TGAGCGAGTC CGCATCGACC GGATCGGAAA ACCTCTCGAG GAACTGAAAA
 _____f
 _____TRIPARTITE LEADER_____f
```

FIG. 6-6.

```
                                                      >ApaI
                                                       |-|
                                     >BspDI  >EcoO109I
                                       |-|     |-|
                    >EcoRV|  >ClaI   |  >Bsp120I
                      |-|    |-|     |    |-|                                    >MslI
        >ApoI >BsiWI    1290   *     |  |  >BanII    >SfcI                        |-|
         |-|    |-|  |-|       |     |  |  |-|       |-|                  1320
>EcoRI    1280   *   |  *      |     |  |  |1300     |  1310              |-|    *
 |-|  *          |      |      |     |  |  |-|*      |  |-|*              |  *
GACGAATTCG CGTACGATAT CGATGGGCCC TATT CTA TAG TGT CAC CTA AAT
                                     Leu *** Cys His Leu Asn>
                                        c_SP6 PROMOTER  c    >

>SacI
            |-|
            >BanII
             |-|
            >BsiHKAI
             |-|                    1340
>Ecl136II  |  >BclI                  |-|
 |-|  1330 |   |-|                   |  *
BGH_POLY_A |-|*|                     |
  |-|* |-| |  ||
  |  * |  *|  ||
GCTAGAGC TCGCTGATCA GCCTCGACTG TGCCTTCTAG TTGCCAGCCA TCTGTGTTT
            1350       *       1360       *       1370       *       1380
                                                                      *

>BanI
                              |-|
       1390         1400        1410       1420       1430       1440
        *            *           *          *          *          *
GCCCCTCCCC CGTGCCTTCC TTGACCCTGG AAGGTGCCAC TCCCACTGTC CTTTCCTAAT
```

FIG. 6-8.

```
       1450        1460        1470        1480        1490        1500
         *           *           *           *           *           *
AAAATGAGGA  AATTGCATCG  CATTGTCTGA  GTAGGTGTCA  TTCTATTCTG  GGGGGTGGGG
                                            >BbsI
                                            —
       1510        1520        1530        1540        1550        1560
         *           *           *           *           *           *
TGGGCAGGA   CAGCAAGGGG  GAGGATTGGG  AAGACAATAG  CCGAAATGAC  CGACCAAGCG
        >BspMI
        —
        >BssSI
        —
       1570        1580        1590        1600        1610        1620
         *           *           *           *           *           *
ACGCCCAACC  TGCCATCACG  AGATTTCGAT  TCCACCGCCG  CCTTCTATGA  AAGGTTGGGC
                    >NaeI
                    —
                    >NgoMI
                    —
                    >BpmI
                    —
                    >BsrFI
                    —
       1630        1640        1650        1660        1670        1680
         *           *           *           *           *           *
TTCGGAATCG  TTTTCCGGGA  CGCCGGCTGG  ATGATCCTCC  AGCGCCGGGA  TCTCATGCTG
```

FIG 6-9.

```
                  >BpmI
        >SV40_early_poly_A
                    |
      1690      1700      1710      1720      1730      1740
    *    *    *    *    *    *    *    *    *    *    *    *
GAGTCTTCG CCCACCCCAA CTTGTTTATT GCAGCTTATA ATGGTTACAA ATAAAGCAAT
                                              >BsmI
      >ApoI                                     |
        |                                       |
      1750      1760      1770      1780      1790      1800
    *    *    *    *    *    *    *    *    *    *    *    *
AGCATCACAA ATTTCACAAA TAAAGCATTT TTTCACTGC ATTCTAGTTG TGGTTTGTCC
                                      >HincII
                                        |
                      >BstII07I       >AccI
                        |  |          |  |
                        >AccI  >SalI  |  |
                        |  |   |  |   |  |
      1810      1820      1830      1840      1850      1860
    *    *    *    *    *    *    *    *    *    *    *    *
AAACTCATCA ATGTATCTTA TCATGTCTGT ATACCGTCGA CCTCTAGCTA GAGCTTGGCG
 d                   PUC19 BACKBONE                            d >BsrBI
                                               |
      1870      1880      1890      1900      1910      1920
    *    *    *    *    *    *    *    *    *    *    *    *
TAATCATGGT CATAGCTGTT TCCTGTGTGA AATTGTTATC CGCTCACAAT TCCACACAAC
 d                                                             d
```

FIG. 6-10.

```
                1930      1940      1950      1960      1970      1980
                   *         *         *         *         *         *
         ATACGAGCCG GAAGCATAAA GTGTAAAGCC TGGGGTGCCT AATGAGTGAG CTAACTCACA
         |_____d__PUC19 BACKBONE_____|
>AseI                                   >BanI                          >AseI
 |--|                                    |--|                          |--|
 | *|                                    |*|                           |  |

1990      2000      2010      2020      2030      2040
                   *         *         *         *         *         *
         TTAATTGCGT TGCGCTCACT GCCCGCTTTC CAGTCGGGAA ACCTGTCGTG CCAGCTGCAT
         |_____d__PUC19 BACKBONE_____|
                                                         >PvuII
                                                          |--|
                                                          | *|

2050      2060      2070      2080      2090      2100
                   *         *         *         *         *         *
         TAATGAATCG GCCAACGCGC GGGGAGAGGC GGTTTGCGTA TGGGGCGCTC TTCCGCTTCC
         |_____d__PUC19 BACKBONE_____|
         >EaeI                                >HaeII  >EarI >SapI
         |--|                                  |--|   |--|  |--|
         |* |                                  |* |   |  |  |  |

FIG 6-11.
```

```
                    >BsiEI                      >BsrBI
       2110      2120      2130      2140      2150      2160
        *         *        |*         *         *|        *         >
TCGCTCACTG ACTCGCTGCG CTCGGTCGTT CGGCTGCGGC GAGCGGTATC AGCTCACTCA
        d                                                         d   pUC19 BACKBONE

>AflIII
       2170      2180      2190      2200      2210      2220
        *         *         *         *        |*         *        >
AAGGCGGTAA TACGGTTATC CACAGAATCA GGGGATAACG CAGGAAAGAA CATGTGAGCA
        d                                                         d   pUC19 BACKBONE 2230      2240      2250      2260      2270      2280
        *         *         *         *         *         *        >
AAAGGCCAGC AAAAGGCCAG GAACCGTAAA AAGGCCGCGT TGCTGGCGTT TTTCCATAGG
        d                                                         d   pUC19 BACKBONE

>DrdI
       2290      2300      2310      2320      2330      2340
        *         *         *        |*         *|        *        >
CTCCGCCCCC CTGACGAGCA TCACAAAAAT CGACGCTCAA GTCAGAGGTG GCGAAACCCG
        d                                                         d   pUC19 BACKBONE

>BssSI
       2350      2360      2370      2380      2390      2400
        *         *         *         *        |*         *        >
ACAGGACTAT AAAGATACCA GGCGTTTCCC CCTGGAAGCT CCCTCGTGCG CTCTCCTGTT
        d                                                         d   pUC19 BACKBONE
```

FIG. 6-12.

```
                                                          >HaeII
            >BsaWI                                         |-|
            |-|2420            2430         2440    2450   2460
   2410       *                  *            *       *     *
     *
CCGACCCTGC CGCTTACCGG ATACCTGTCC GCCTTTCTCC CTTCGGGAAG CGTGGCGCTT
          d          PUC19 BACKBONE                              d

>SfcI
              |-|
   2470       |2480            2490         2500    2510   2520
     *          *                *            *       *     *
TCTCAATGCT CACGCTGTAG GTATCTCAGT TCGGTGTAGG TCGTTCGCTC CAAGCTGGGC
          d          PUC19 BACKBONE                              d

>BsiHKAI
   |-------|                                 >BsiEI      >BsaWI
>ApaLI|                                      |-|         |-|
|---|*|2530            2540         2550     |2560   2570 |2580
   *  *                  *            *        *      *    *
TGTGTGCACG AACCCCCCGT TCAGCCCGAC CGCTGCGCCT TATCCGGTAA CTATCGTCTT
          d          PUC19 BACKBONE                              d

>AlwNI
                                                     |-|
   2590       2600             2610         2620     |2630   2640
     *          *                *            *        *      *
GAGTCCAACC CGGTAAGACA CGACTTATCG CCACTGGCAG CAGCCACTGG TAACAGATT
          d          PUC19 BACKBONE                              d
```

FIG. 6-13.

```
                      >SfcI
                       |
          2650      2660     |2670      2680      2690      2700
            *         *       *|         *         *         *
    AGCAGAGCCGA GGTATGTAGG CGGTGCTACA GAGTTCTTGA AGTGGTGGCC TAACTACGGC
                           d          PUC19 BACKBONE                 d

>Eco57I
                                                               |
          2710      2720      2730      2740      2750      |2760
            *         *         *         *         *         *|
    TACACTAGAA GGACAGTATT TGGTATCTGC GCTCTGCTGA AGCCAGTTAC CTTCGGAAAA
                           d          PUC19 BACKBONE                 d 2770      2780      2790      2800      2810      2820
            *         *         *         *         *         *
    AGAGTTGGTA GCTCTTGATC CGGCAAACAA ACCACCGCTG GTAGCGGGTGG TTTTTTTGTT
                           d          PUC19 BACKBONE                 d 2830      2840      2850      2860      2870      2880
            *         *         *         *         *         *
    TGCAAGCAGC AGATTACGCG CAGAAAAAAA GGATCTCAAG AAGATCCTTT GATCTTTTCT
                           d          PUC19 BACKBONE                 d

>BspHI
                                                      |
          2890      2900      2910      2920      2930|     2940
            *         *         *         *         *         *
    ACGGGGTCTG ACGCTCAGTG GAACGAAAAC TCACGTTAAG GGATTTTGGT CATGAGATTA
                           d          PUC19 BACKBONE                 d
```

FIG 6-14.

```
                                              >DraI
                                               -|-
    2950         2960         2970         2980         2990         3000
     *    *       *    *       *    *       *    *       *    *       *    *
TCAAAAAGGA TCTTCACCTA GATCCTTTTA AATTAAAAAT GAAGTTTTAA ATCAATCTAA  >
         d                    |d                                     
         ____PUC19 BACKBONE____|_____

>BanI
                                                                 -|-
    3010         3020         3030         3040         3050         3060
     *    *       *    *       *    *       *    *       *    *       *    *
AGTATATATG AGTAAACTTG GTCTGACAGT TACCAATGCT TAATCAGTGA GGCACCTATC  >
         |a                                           AMP-ORF       
         |d                                                     a   
         ___PUC19 BACKBONE____|_____d

>AhdI
                                            -|-
    3070         3080         3090         3100         3110         3120
     *    *       *    *       *    *       *    *       *    *       *    *
TCAGCGATCT GTCTATTTCG TTCATCCATA GTTGCCTGAC TCCCCGTCGT GTAGATAACT  >
                    a                                               
AMP-ORF                                                         a   
_____d

>BsaI
                                                     -|-
                                              >BsrDI      >BpmI
                                               -|-         -|-
    3130         3140         3150         3160         3170         3180
     *    *       *    *       *    *       *    *       *    *       *    *
ACGATACGGG AGGGCTTACC ATCTGGCCCC AGTGCTGCAA TGATACCGCG AGACCCACGC  >
                    a                                           a   
AMP-ORF                                                             
_____PUC19 BACKBONE_____d

FIG. 6-15.
```

```
                >BsrFI                              >BglI
          —  |                              —  |
     |        3190         3200         3210         3220         3230         3240
     *           *            *            *            *            *            *
          TCACCGGCTC CAGATTTATC AGCAATAAAC CAGCCAGCCG GAAGGGCCGA GCGCAGAAGT
     a                                AMP-ORF                                    a>
     d     PUC19 BACKBONE                                                         d>

>AseI
                                         —  |
          3250         3260         3270         3280         3290         3300
     *           *            *            *            *            *            *
          GGTCCTGCAA CTTTATCCGC CTCCATCCAG TCTATTAATT GTTGCCGGGA AGCTAGAGTA
     a                                AMP-ORF                                    a>
     d     PUC19 BACKBONE                                                         d>

>Pspl406I                                          >MslI
                 —  |                                                —  |
          >FspI                   >BsrDI     >SfcI
          —  |                    —  |      —  |
     3310         3320         3330         3340         3350         3360
     *           *            *            *            *            *            *
          AGTAGTTCGC CAGTTAATAG TTTGCGCAAC GTTGTTGCCA TTGCTACAGG CATCGTGGTG
     a                                AMP-ORF                                    a>
     d     PUC19 BACKBONE                                                         d>
```

FIG. 6-16.

```
                                              >BsiEI
                    3610       3620        3630        3640       3650        3660
                      *          *           *           *          *           *
              TGAGAATAGT GTATGCGGCG ACCGAGTTGC TCTTGCCCGG CGTCAATACG GGATAATACC
              a                                AMP-ORF                                 a>
              d                              PUC19 BACKBONE                            d>

>Psp1406I
                                        >DraI  >BsiHKAI        >XmnI
                    3670       3680        3690        3700       3710        3720
                      *          *           *           *          *           *
              GCGCCACATA GCAGAACTTT AAAAGTGCTC ATCATTGGAA AACGTTCTTC GGGGCGAAAA
              a                                AMP-ORF                                 a>
              d                              PUC19 BACKBONE                            d>

>ApaLI
                                                                    >Eco57I
                                                          >BsssSI | >BsiHKAI
                    3730       3740        3750        3760       3770        3780
                      *          *           *           *          *           *
              CTCTCAAGGA TCTTACCGCT GTTGAGATCC AGTTCGATGT AACCCACTCG TGCACCCAAC
              a                                AMP-ORF                                 a>
              d                              PUC19 BACKBONE                            d>
```

*FIG. 6-18.*

```
       3790         3800         3810         3820         3830         3840
         *    *       *    *       *    *       *    *       *    *       *    *
TGATCTTCAG CATCTTTTAC TTTCACCAGC GTTTCTGGGT GAGCAAAAAC AGGAAGGCAA
          a                             AMP-ORF                          a  >
          d    pUC19 BACKBONE                                            d  >
                                       >MslI
                                        —
       3850         3860         3870     — 3880         3890         3900  >EarI
         *    *       *    *       *    * *  *    *       *    *       *    —*
AATGCCGCAA AAAGGGAAT AAGGGCGACA CGGAAATGTT GAATACTCAT ACTCTTCCTT
          a                             AMP-ORF                          a  >
          d    pUC19 BACKBONE                                            d  >
                                              >BspHI   >BsrBI
  >SspI                                        —        —
   —   3910         3920         3930     — 3940 — 3950         3960
   —*    *       *    *       *    *       *  *   *  *    *       *    *  >
TTTCAATATT ATTGAAGCAT TTATCAGGGT TATTGTCTCA TGAGCGGATA CATATTTGAA
          d    pUC19 BACKBONE                                            d  >
```

FIG. 6-19.

```
         3970       3980       3990       4000       4010       4020
          *          *          *          *          *          *
TGTATTTAGA AAAATAAACA AATAGGGGTT CCGCGCACAT TTCCCCGAAA AGTGCCACCT
          |_____d_____|_____d__pUC19 BACKBONE_d_____d_____>
>HincII
   |--|
>AatII
   |--|
>AccI
   |---|
>SalI
   |--*-|
GACGTC
|_____>
```

FIG 6-20.

```
                                          >HincII
                                             ---
                                             >AccI
                                             ---
                                             >SalI
        >BglII                               ---
        ---                                  ---
         10         20         30         40         50         60
       * |        * |        * |        * |        * |        * |
GACGGATCGG GAGATCTCCC GATCCCCTAT GGTCGACTCT CAGTACAATC TGCTCTGATG >AlwNI
            ---
         70         80         90        100        110        120
       * |        * |        * |        * |        * |        * |
CCGCATAGTT AAGCCAGTAT CTGCTCCCTG CTTGTGTGTT GGAGGTCGCT GAGTAGTGCG >ApoI                                  >MfeI
  ---                                    ---
        130        140        150        160        170        180
       * |        * |        * |        * |        * |        * |
CGAGCAAAAT TTAAGCTACA ACAAGGCAAG GCTTGACCGA CAATTGCATG AAGAATCTGC >NruI                     >AflIII
                         ---                       ---
                                                       >MluI      >HincII
                                                       ---        ---
        190        200        210        220        230            ---
       * |        * |        * |        * |        * |            * |
TTAGGGTTAG GCGTTTGCG CTGCTTCG CGA TGT ACG GGC CAG ATA TAC GCG TTG
                              Arg Cys Thr Gly Gln Ile Tyr Ala Leu>
                              f____f____CMV PROMOTER____f____f____>
```

FIG. 8-1.

```
                    >SpeI         >AseI
                    |--|          |--|
     240            250            260            270            280
       *              *              *              *              *
ACA TTG ATT ATT GAC TAG TTA ATA GTA ATC AAT TAC GGG GTC ATT
Thr Leu Ile Ile Asp *** Leu Leu Ile Val Ile Asn Tyr Gly Val Ile>
|__f__|__f__|__f__|__f__|__f__CMV PROMOTER__f__|__f__|__f__|__f__|

290            300            310            320            330
       *              *              *              *              *
AGT TCA TAG CCC ATA TAT GGA GTT CCG CGT TAC ATA ACT TAC GGT AAA
Ser Ser *** Pro Ile Tyr Gly Val Pro Arg Tyr Ile Thr Tyr Gly Lys>
|__f__|__f__|__f__|__f__|__f__CMV PROMOTER__f__|__f__|__f__|__f__|

>BglI                                              >AatII
          |--|                                               |--|
     340            350            360            370
       *              *              *              *
TGG CCC GCC TGG CTG ACC GCC CAA CGA CCC CCG CCC ATT GAC GTC AAT
Trp Pro Ala Trp Leu Thr Ala Gln Arg Pro Pro Pro Ile Asp Val Asn>
|__f__|__f__|__f__|__f__|__f__CMV PROMOTER__f__|__f__|__f__|__f__|

380            390            400            410            420
       *              *              *              *              *
AAT GAC GTA TGT TCC CAT AGT AAC GCC AAT AGG GAC TTT CCA TTG ACG
Asn Asp Val Cys Ser His Ser Asn Ala Asn Arg Asp Phe Pro Leu Thr>
|__f__|__f__|__f__|__f__|__f__CMV PROMOTER__f__|__f__|__f__|__f__|
```

FIG. 8-2.

```
                                              >BglI
       430         440         450         460         470
TCA ATG GGT GGA CTA TTT ACG GTA AAC TGC CCA CTT GGC AGT ACA TCA
Ser Met Gly Gly Leu Phe Thr Val Asn Cys Pro Leu Gly Ser Thr Ser>
    f_CMV PROMOTER_f

>NdeI                                        >AatII
       480         490         500         510         520
AGT GTA TCA TAT GCC AAG TAC GCC CCC TAT TGA CGT CAA TGA CGG TAA
Ser Val Ser Tyr Ala Lys Tyr Ala Pro Tyr *** Arg Gln *** Arg ***>
    f_CMV PROMOTER_f

>BglI                         >BsaAI                  >StyI
       530         540      >SnaBI  550         560    >NcoI   >MslI
                                               570
ATG GCC CGC CTG GCA CTG TTA TGC CCA GTA CAT GAC CTT ATG GGA CTT TCC
Met Ala Arg Leu Ala Leu Leu Cys Pro Val His Asp Leu Met Gly Leu Ser>
    f_CMV PROMOTER_f 580         590         600         610
TAC TTG GCA GTA CAT CTA CGT ATT AGT CAT CGC TAT CAT TAC CAT GGT GAT
Tyr Leu Ala Val His Leu Arg Ile Ser His Arg Tyr His Gly Asp>
    f_CMV PROMOTER_f
```

FIG. 8-3.

```
                    630            640            650            660
     620             *              *              *              *                                            >BanI
      *              |              |              |              |                                          |—  —  *
GCG GTT TTG GCA GTA CAT CAA TGG GCG TGG ATA GCG GTT TGA CTC ACG
Ala Val Leu Ala Val His Gln Trp Ala Trp Ile Ala Val *** Leu Thr>
|___f___|___f___|___f___f_CMV PROMOTER__f___|___f___|___f___|___f___|  >

680            690           >AatII           710
     670             *              *           |—  —  *           *
      *              |              |              |              |
GGG ATT TCC AAG TCT CCA CCC CAT TGA CGT CAA TGG GAG TTT GTT TTG
Gly Ile Ser Lys Ser Pro Pro His *** Arg Gln Trp Glu Phe Val Leu>
|___f___|___f___|___f___|___f___f_CMV PROMOTER__f___|___f___|___f___|  >

730            740            750            760
     720             *              *              *              *
      *              |              |              |              |
GCA CCA AAA TCA ACG GGA CTT TCC AAA ATG TCG TAA CAA CTC CGC CCC
Ala Pro Lys Ser Thr Gly Leu Ser Lys Met Ser *** Gln Leu Arg Pro>
|___f___|___f___|___f___|___f___|___f_CMV PROMOTER__f___|___f___|  >

780            790            800            810
     770             *              *              *              *
      *              |              |              |              |
ATT GAC GCA AAT GGG CGG TAG GCG TGT ACG GTG GGA GGT CTA TAT AAG
Ile Asp Ala Asn Gly Arg *** Ala Cys Thr Val Gly Gly Leu Tyr Lys>
|___f___|___f___|___f___|___f___|___f___|___f___|___f___|___f___|  >
```

FIG. 8-4.

```
>BsiHKAI
   SacI
      BanII
>Ecl136II
   |   |   820            830            840            850
   |   |    *              *              *              *
CAG AGC TCT CTG GCT AAC TAG AGA ACC CAC TGC TTA CTG GCT TAT CGA
Gln Ser Ser Leu Ala Asn ***  Arg Thr His Cys Leu Leu Ala Tyr Arg>
 f   f   f   f   f   f  f_CMV_PROMOTER  f   f   f   f   f   f

>BsaI
                    >SfcI         >HindIII         >KpnI
                     |             |                >BanI
                     |             |                >Acc65I
      860            |   870       |    880            890            900            910
       *             |    *        |     *              *              *              *
>AseI
>T7_PROMOTER
AAT T AATACGA CTCACTATAG GGAGACCCAA GCTTCGGCGC GGAGACCCAA GCTTCGGCG GGTACCACTC
Asn Xxx>
 f_>
```

FIG. 8-5.

```
                                              >PflMI
                    >EarI          >PvuII        >BanII
      |  920      | 930      | 940      | 950      | 960      | 970
      *    *      *    *     *    *     *    *     *    *     *    *    >
TCTTCCGCAT CGCTGTCTGC GAGGGCCAGC TGTTGGGCTC GCGGTTGAGG ACAAACTCTT
      g                                                       g
                                                TRIPARTITE LEADER SEQUENCE

>EarI       >ScaI
      |  980      | 990      | 1000     | 1010     | 1020     | 1030
      *    *      *    *     *    *     *    *     *    *     *    *    >
CGCGGTCTTT CCAGTACTCT TGGATCGGAA ACCCGTCGGC CTCCGAACGG TACTCCGCCA
      g                                                       g
                                    TRIPARTITE LEADER SEQUENCE

>XhoI
                                                       >AvaI
                                                       >BsoBI
     >EcoO109I         >BsiEI                          >PaeR7I
      |  1040    |     >BsaWI                           |
      *    *     *  1050|*   * |1060    *    * 1070     *    * 1080    *    * 1090
CCGAGGGACC TGAGCGAGTC CGCATCGACC GGATCGGAAA ACCTCTCGAG GAACTGAAAA

FIG 8-6.
```

```
                    TRIPARTITE LEADER SEQUENCE                  g          >
            >HpaI                                      >PpuMI
            >HincII                          >EcoO109I
    1100      1110      1120      1130       1140      1150
  *   *    *    *    *    *    *    *    *     *    *    *
ACCAGAAAGT TAACTGGTAA GTTAGTCTT TTTGTCTTTT TATTTCAGGT CCCGGATCTG
               b     HYBRID SV40 LATE INTRON   b    >

>21_bp_tandem_repeat_III_[110],[102],[112]           >Ppu10I
    1160      1170      1180      1190       1200      1210
  *   *    *    *    *    *    *    *    *     *    *    *
AGTTAGGGCG GGACATGGGC GGAGTTAGGG GCGGGACTAT GGTTGCTGAC TAATTGAGAT
         <                       h_EARLY MRNA          h >SphI                                <72_bp_tandem_repeat_enhancer_sequence_|
>NsiI
    1220      1230      1240      1250       1260      1270
  *   *    *    *    *    *    *    *    *     *    *    *
GCATGCTTTG CATACTTCTG CCTGCTGGGG AGCCTGGGGA CTTTCCACAC CTGGTTGCTG
 <           h      EARLY MRNA           h
```

```
         1570       1580       1590       1600       1610       1620
           *          *          *          *          *          *
    TCAGCCTCGA CTGTGCCTTC TAGTTGCCAG CCATCTGTTG TTTGCCCCTC CCCCGTGCCT
                         >BanI
                          |
         1630      |1640       1650       1660       1670       1680
           *          *          *          *          *          *
    TCCTTGACCC TGGAAGGTGC CACTCCCACT GTCCTTTCCT AATAAAATGA GGAAATTGCA 1690       1700       1710       1720       1730       1740
           *          *          *          *          *          *
    TCGCATTGTC TGAGTAGGTG TCATTCTATT CTGGGGGGTG GGGTGGGGCA GGACAGCAAG

>BspMI
                                                             |
                              >BbsI                        >BsssI
                                |                            |
         1750       1760       1770       1780       1790       1800
           *          *          *          *          *          *
    GGGGAGGATT GGGAAGACAA TAGCCGAAAT GACCGACCAA GCGACGCCCA ACCTGCCATC 1810       1820       1830       1840       1850       1860
           *          *          *          *          *          *
    ACGAGATTTC GATTCCACCG CCGCCTTCTA TGAAAGGTTG GGCTTCGAA TCGTTTTCCG
```

FIG. 8-10.

```
>NaeI       
  ---
>BpmI       
  ---
>BsrFI      
  ---
NgoMI
  ---
       *         *         *         *         *         *
      1870      1880      1890      1900      1910      1920
GGACGCCGGC TGGATGATCC TCCAGCGCGG GGATCTCATG CTGGAGTTCT TCGCCCACCC

>BpmI
  ---
>SV40_early_poly_A
                                                            >ApoI
                                                              ---
       *         *         *         *         *         *
      1930      1940      1950      1960      1970      1980
CAACTTGTTT ATTGCAGCTT ATAATGGTTA CAAATAAAGC AATAGCATCA CAAATTTCAC >BsmI
                           ---
       *         *         *         *         *         *
      1990      2000      2010      2020      2030      2040
AAATAAAGCA TTTTTTTCAC TGCATTCTAG TTGTGGTTTG TCCAAACTCA TCAATGTATC
```

FIG. 8-11.

```
                  >HincII
       >Bstl107I  >AccI
           >AccI  >SalI
   2050     2060     2070     2080     2090     2100
    *         *        *        *        *        *
TTATCATGTC TGTATACCGT CGACCTCTAG CTAGAGCTTG GCGTAATCAT GGTCATAGCT
                                                      PUC19 BACKBONE >
                              >BsrBI
   2110     2120     2130     2140     2150     2160
    *         *        *        *        *        *
GTTTCCTGTG TGAAATTGTT ATCCGCTCAC AATTCCACAC AACATACGAG CCGGAAGCAT
   e         e        e       PUC19 BACKBONE                      e >BanI                         >AseI
   2170     2180     2190     2200     2210     2220
    *         *        *        *        *        *
AAAGTGTAAA GCCTGGGGTG CCTAATGAGT GAGCTAACTC ACATTAATTG CGTTGCGCTC
   e                              e                              e >PvuII   >AseI     >EaeI
   2230     2240     2250     2260     2270     2280
    *         *        *        *        *        *
ACTGCCCGCT TTCCAGTCGG GAAACCTGTC GTGCCAGCTG CATTAATGAA TCGGCCAACG
   e        PUC19 BACKBONE                           e            e
```

FIG 8-12.

```
                                       >SapI
                        >HaeII         >EarI
      *    2290    *    2300    *    2310    *    2320    *    2330    *    2340
CGCGGGGAGA GGCGGTTTGC GTATTGGGCG CTCTTCCGCT TCCTCGCTCA CTGACTCGCT
           e               e               e PUC19 BACKBONE           e         >

>BsiEI              >BsrBI
      *    2350    *    2360    *    2370    *    2380    *    2390    *    2400
GCGCTCGGTC GTTCGGCTGC GGCGAGCGGT ATCAGCTCAC TCAAAGGCGG TAATACGGTT
           e               e               e PUC19 BACKBONE           e         >

>AflIII
      *    2410    *    2420    *    2430    *    2440    *    2450    *    2460
ATCCACAGAA TCAGGGGATA ACGCAGGAAA GAACATGTGA GCAAAAGGCC AGCAAAAGGC
           e               e               e PUC19 BACKBONE           e         >

*    2470    *    2480    *    2490    *    2500    *    2510    *    2520
CAGGAACCGT AAAAAGGCCG CGTTGCTGGC GTTTTTCCAT AGGCTCCGCC CCCCTGACGA
           e               e               e PUC19 BACKBONE           e         >
```

FIG. 8-13.

```
                 2530          2540          2550          2560          2570          2580
                   *     *       *     *       *     *       *     *       *     *       *     *
         GCATCACAAA AATCGACGCT CAAGTCAGAG GTGGCGAAAC CCGACAGGAC TATAAAGATA
                             |->DrdI                                                        
         e_____ pUC19 BACKBONE _____e 2590          2600          2610          2620          2630          2640
                   *     *       *     *       *     *       *     *       *     *       *     *
         CCAGGCGTTT CCCCCTGGAA GCTCCCTCGT GCGCTCTCCT GTTCCGACCC TGCCGCTTAC
                                        |->BssSI                                |->BsaWI
         e_____ pUC19 BACKBONE _____e 2650          2660          2670          2680          2690          2700
                   *     *       *     *       *     *       *     *       *     *       *     *
         CGGATACCTG TCCGCCTTTC TCCCTTCGGG AAGCGTGGCG CTTTCTCAAT GCTCACGCTG
                                                  |->HaeII                              |->SfcI
         e_____ pUC19 BACKBONE _____e 2710          2720          2730          2740          2750          2760
                   *     *       *     *       *     *       *     *       *     *       *     *
         TAGGTATCTC AGTTCGGTGT AGGTCGTTCG CTCCAAGCTG GGCTGTGTGC ACGAACCCCC
                                                                     |->BsiHKAI
                                                            |->ApaLI
         e_____ pUC19 BACKBONE _____e
```

FIG. 8-14.

```
         >BsiEI          >BsaWI
         —|—             —|
       2770    2780    2790    2800    2810    2820
         *       *       *       *       *       *
CGTTCAGCCC GACCGCTGCG CCTTATCCGG TAACTATCGT CTTGAGTCCA ACCCGGTAAG
         e       e       e    PUC19 BACKBONE e       e

>AlwNI
                              —|—
       2830    2840    2850    2860    2870    2880
         *       *       *       *       *       *
ACACGACTTA TCGCCACTGG CAGCAGCCAC TGGTAACAGG ATTAGCAGAG CGAGGTATGT
         e       e       e    PUC19 BACKBONE e       e

>SfcI
    —|—
       2890    2900    2910    2920    2930    2940
         *       *       *       *       *       *
AGGCGGTGCT ACAGAGTTCT TGAAGTGGTG GCCTAACTAC GGCTACACTA GAAGGACAGT
         e       e       e    PUC19 BACKBONE e       e

>Eco57I
                                             —|—
       2950    2960    2970    2980    2990    3000
         *       *       *       *       *       *
ATTTGGTATC TGCGCTCTGC TGAAGCCAGT TACCTTCGGA AAAAGAGTTG GTAGCTCTTG
         e       e       e    PUC19 BACKBONE e       e
```

FIG 8-15.

```
       3010       3020       3030       3040       3050       3060
    *    |    *    |    *    |    *    |    *    |    *    |    *    |
ATCCGGCAAA CAAACCACCG CTGGTAGCGG TGGTTTTTTT GTTTGCAAGC AGCAGATTAC
e_____PUC19 BACKBONE_____e 3070       3080       3090       3100       3110       3120
    *    |    *    |    *    |    *    |    *    |    *    |    *    |
GCGCAGAAAA AAAGGATCTC AAGAAGATCC TTTGATCTTT TCTACGGGGT CTGACGCTCA
e_____PUC19 BACKBONE_____e
                                       >BspHI 3130       3140       3150       3160       3170       3180
    *    |    *    |    *    |    *    |    *    |    *    |    *    |
GTGGAACGAA AACTCACGTT AAGGGATTTT GGTCATGAGA TTATCAAAAA GGATCTTCAC
e_____PUC19 BACKBONE_____e
   >DraI                        >DraI 3190       3200       3210       3220       3230       3240
    *    |    *    |    *    |    *    |    *    |    *    |    *    |
CTAGATCCTT TTAAATTAAA AATGAAGTTT TAAATCAATC TAAAGTATAT ATGAGTAAAC
e_____PUC19 BACKBONE_____e
                                             >BanI 3250       3260       3270       3280       3290       3300
    *    |    *    |    *    |    *    |    *    |    *    |    *    |
TTGGTCTGAC AGTTACCAAT GCTTAATCAG TGAGGCACCT ATCTCAGCGA TCTGTCTATT
e____PUC19 BACKBONE____e  a_____AMP-ORF_____a
```

*FIG. 8-16.*

```
                                                      >AseI
                                                       —
           3490          3500          3510          3520          3530          3540
            *    *        *    *        *    *        *    *        *    *        *    *
       CGCCTCCATC CAGTCTATTA ATTGTTGCCG GGAAGCTAGA GTAAGTAGTT CGCCAGTTAA >
       ─────────────────────a─────────────────────────────────────────a─
                            AMP-ORF
       ─────────────────────e─────────────────────────────────────────e─ >
                            PUC19 BACKBONE

>PspI406I
       ┌──────
       >FspI           >BsrDI        >SfcI       >MslI
        —               —              —           —
           3550          3560          3570          3580          3590          3600
            *    *        *    *        *    *        *    *        *    *        *    *
       TAGTTTGCGC AACGTTGTTG CCATTGCTAC AGGCATCGTG GTGTCACGCT CGTCGTTTGG >
       ─────────a─────────────────────────────────────────a─────────────
                AMP-ORF
       ─────────e─────────────────────────────────────────e───────────── >
                PUC19 BACKBONE

>BsaWI
                    —
           3610          3620          3630          3640          3650          3660
            *    *        *    *        *    *        *    *        *    *        *    *
       TATGGCTTCA TTCAGCTCCG GTTCCCAACG ATCAAGGCGA GTTACATGAT CCCCATGTT >
       ─────────a─────────────────────────────────────────a────────────
                AMP-ORF
       ─────────e─────────────────────────────────────────e──────────── >
                PUC19 BACKBONE

>BsiEI
                                              —
                                             >PvuI
                                              —                     >EaeI
                                                                     —
           3670          3680          3690          3700          3710          3720
            *    *        *    *        *    *        *    *        *    *        *    *
       GTGCAAAAAA GCGGTTAGCT CCTTCGGTCC TCCGATCGTT GTCAGAAGTA AGTTGGCCGC >
       ─────────a─────────────────────────────────────────a─────────────
                AMP-ORF
       ─────────e─────────────────────────────────────────e───────────── >
                PUC19 BACKBONE
```

*FIG. 8-18.*

```
         >MslI
        |----|
      3730      3740       3750       3760       3770       3780
    *    *    *    *    *    *    *    *    *    *    *    *
  AGTGTTATCA CTCATGGTTA TGGCAGCACT GCATAATTCT CTTACTGTCA TGCCATCCGT
  a                              a                              e  >
  e  _____AMP-ORF_____
     _____pUC19 BACKBONE_____

>ScaI
                                   |----|
      3790       3800       3810       3820       3830       3840
    *    *    *    *    *    *    *    *    *    *    *    *
  AAGATGCTTT TCTGTGACTG GTGAGTACTC AACCAAGTCA TTCTGAGAAT AGTGTATGCG
  a                              a                              e  >
  e  _____AMP-ORF_____
     _____pUC19 BACKBONE_____

>BsiEI
  |---|
      3850       3860       3870       3880       3890       3900
    *    *    *    *    *    *    *    *    *    *    *    *
  GCGACCGAGT TGCTCTTGCC CGGCGTCAAT ACGGGATAAT ACCGCGCCAC ATAGCAGAAC
  a                              a                              e  >
  e  _____AMP-ORF_____
     _____pUC19 BACKBONE_____

>Psp1406I
                             |--|   >XmnI
                                   |----|
  >DraI  >BsiHKAI
  |---| |----|
      3910       3920       3930       3940       3950       3960
    *    *    *    *    *    *    *    *    *    *    *    *
  TTTAAAAGTG CTCATCATTG GAAAACGTTC TTCGGGGCGA AAACTCTCAA GGATCTTACC
  a                              a                              e  >
  e  _____AMP-ORF_____
     _____pUC19 BACKBONE_____
```

FIG. 8-19.

```
                                      >Eco57I
                                        >ApaLI
                     >BssSI  >BsiHKAI
           3980          3990          4000          4010          4020
             *             *             *             *             *
GCTGTTGAGA TCCAGTTCGA TGTAACCCAC TCGTGCACCC AACTGATCTT CAGCATCTTT
         a                                                          a
         e    AMP-ORF                                               e
              PUC19 BACKBONE 4030          4040          4050          4060          4070          4080
             *             *             *             *             *             *
TACTTTCACC AGCGTTTCTG GGTGAGCAAA AACAGGAAGG CAAAATGCCG CAAAAAAGGG
         a                                                          a
         e    AMP-ORF                                               e
              PUC19 BACKBONE

>MslI                              >EarI    >SspI
           4090          4100          4110          4120          4130          4140
             *             *             *             *             *             *
AATAAGGGCG ACACGGAAAT GTTGAATACT CATACTCTTC CTTTTTCAAT ATTATTGAAG
         a                                  a
         e    AMP-ORF                                               e
              PUC19 BACKBONE
```

FIG. 8-20.

```
                >BspHI   >BsrBI
                  -|-      -|-
     4150       4160       4170       4180       4190       4200
       *    *    *    *    *    *    *    *    *    *    *
CATTTATCAG GGTTATTGTC TCATGAGCGG ATACATATTT GAATGTATTT AGAAAAATAA
                                e———————————————————————————————>
         e——————————————————————
             PUC19 BACKBONE

>HincII
                                                 -|-
                                              >AccI
                                                =|=
                                              >AatII
                                                -|-
                                                >SalI
                                                 =|=
     4210       4220       4230       4240
       *    *    *    *    *    *    *    *
ACAAATAGGG GTTCCGCGCA CATTTCCCCG AAAAGTGCCA CCTGACGTC
                                                    e———————————>
        e——————————————————————————————————
                      PUC19 BACKBONE
```

RETINOBLASTOMA FUSION PROTEINS

This is a divisional application of application Ser. No. 08/801,092, filed Feb. 14, 1997 and now U.S. Pat. No. 6,074,850, which is a continuation-in-part of application Ser. No. 08/751,517, filed Nov. 15, 1996, now abandoned.

BACKGROUND OF THE INVENTION

Both the retinoblastoma gene (RB) and transcription factor E2F play a critical role in cell growth control (for a review, see Adams, P. & Kaelin, W. *Seminars in Cancer Biology* 6:99–108 (1995)). The RB locus is frequently inactivated in a variety of human tumor cells. Reintroduction of a wild-type RB gene (e.g., Bookstein et al. *Science* 247:712–715 (1990)) or RB protein (pRB) (e.g., Antelman et al. *Oncogene* 10:697–704(1995)) into RBneg/RBmut cells can suppress growth in culture and tumorigenicity in vivo.

While E2F serves to activate transcription of S-phase genes, its activity is kept in check by RB. RB arrests cells by blocking exit from G into S-phase (for example, Dowdy et al. *Cell* 73:499–511 (1993)) but the precise pathway of the arrest remains unclear.

Although E2F forms complexes with RB, complex formation is more efficient if an E2F-related protein, DP-1, is present. E2F-1 and DP-1 form stable heterodimers which bind to DNA (for example, Qin et al. *Genes and Dev.* 6-:953–964 (1992)). DP-1-E2F complexes serve to cooperatively activate transcription of E2F-dependent genes. Such transcription can be repressed by pRB in the same manner as E2F-1 or DP-1 activated transcription.

Transcriptional repression of genes by RB in some instances can be achieved by tethering pRB to a promoter. For example, GAL4-pRB fusions bind to GAL4 DNA binding domains and repress transcription from p53, Sp-1 or AP-1 elements (Adnane, et al. *J. Biol. Chem.* 270:8837–8843 (1995); Weintraub, et al. *Nature* 358:259–261 (1995)). Sellers, et al. (*Proc. Natl. Acad. Sci.* 92:11544–11548 (1995)) disclosed fusions of amino acid residues 1–368 of E2F with amino acids 379–792 or 379–928 of RB.

Chang, et al. (*Science* 267:518–521 (1995)) disclosed the use of a replication-defective adenovirus-RB construct in the reduction of neointima formation in two animal models of restenosis, a hyperproliferative disorders.

SUMMARY OF THE INVENTION

The instant invention provides the surprising result that a-fusion of an E2F polypeptide with an RB polypeptide is more efficient in repressing transcription of the E2F promoter than RB alone, and that such fusions can cause cell cycle arrest in a variety of cell types. Such fusions can thus address the urgent need for therapy of hyperproliferative disorders, including cancer.

One aspect of the invention is a polypeptide comprising a fusion of a transcription factor, the transcription factor comprising a DNA binding domain, and a retinoblastoma (RB) polypeptide, the RB polypeptide comprising a growth suppression domain. Another aspect of the invention is DNA encoding such a fusion polypeptide. The DNA can be inserted in an adenovirus vector.

In some embodiments of the invention, the transcription factor is E2F. The cyclin A binding domain of the E2F can be deleted or nonfunctional. The E2F can comprise amino acid residues about 95 to about 194 or about 95 to about 286 in some embodiments.

The retinoblastoma polypeptide can be wild-type RB, RB56, or a variant or fragment thereof. In some embodiments, the retinoblastoma polypeptide comprises amino acid residues of about 379 to about 928. Preferred amino acid substitutions of the RB polypeptide include residues 2, 608, 788, 807, and 811.

Another aspect of the invention is an expression vector comprising DNA encoding a polypeptide, the polypeptide comprising a fusion of a transcription factor, the transcription factor comprising a DNA binding domain, and a retinoblastoma (RB) polypeptide, the RB polypeptide comprising a growth suppression domain. In some embodiments a tissue-specific promoter is operatively linked to DNA encoding the fusion polypeptide. The tissue-specific promoter can be a smooth muscle alpha actin promoter.

Another aspect of the invention is a method for treatment of hyperproliferative disorders comprising administering to a patient a therapeutically effective dose of an E2F-RB fusion polypeptide. The hyperproliferative disorder can be cancer. In some embodiments the hyperproliferative disorder is restenosis. The fusion polypeptide and nucleic acid encoding the fusion polypeptide can be used to coat devices used for angioplasty.

BRIEF DESCRIPTION OF THE DRAWINGS

FIG. 1A (SEQ ID NO:1) depicts the predicted amino acid sequence of E2F.

FIG. 1B (SEQ ID NO:2) depicts the nucleotide sequence of transcription factor E2F.

FIG. 2A (SEQ ID NO:3) depicts the nucleotide sequence of pRB as disclosed by Lee, et al. (*Nature* 329:642–645 (1987).

FIG. 2B (SEQ ID NO:4) depicts the predicted amino acid sequence of pRB.

FIG. 4 (SEQ ID NOS:5–18) depicts the nucleotide sequence of plasmid pCTM.

is a mock transfection. In panel B, results are shown for transfection of Saos-2 cells with (1) RB56, (2,3) E2F194-5s, and (4,5) E2F286-5s. In panel C, results are shown for transfection of 5637 cells with (2,3) RB56 wild-type, (4,5) RB56-5s; (6,7) E2F194-5s; (7,8) E2F286-5S. Lane (1) is an RB56 protein standard. In panel D, results are shown for NIH-3T3 transfected (3) RB56, (4) E2F286-5s, (5) E2F194-5s. Lane (1) is an RB56 standard; lane (2) is an RB110 standard.

Figures 6, 7:
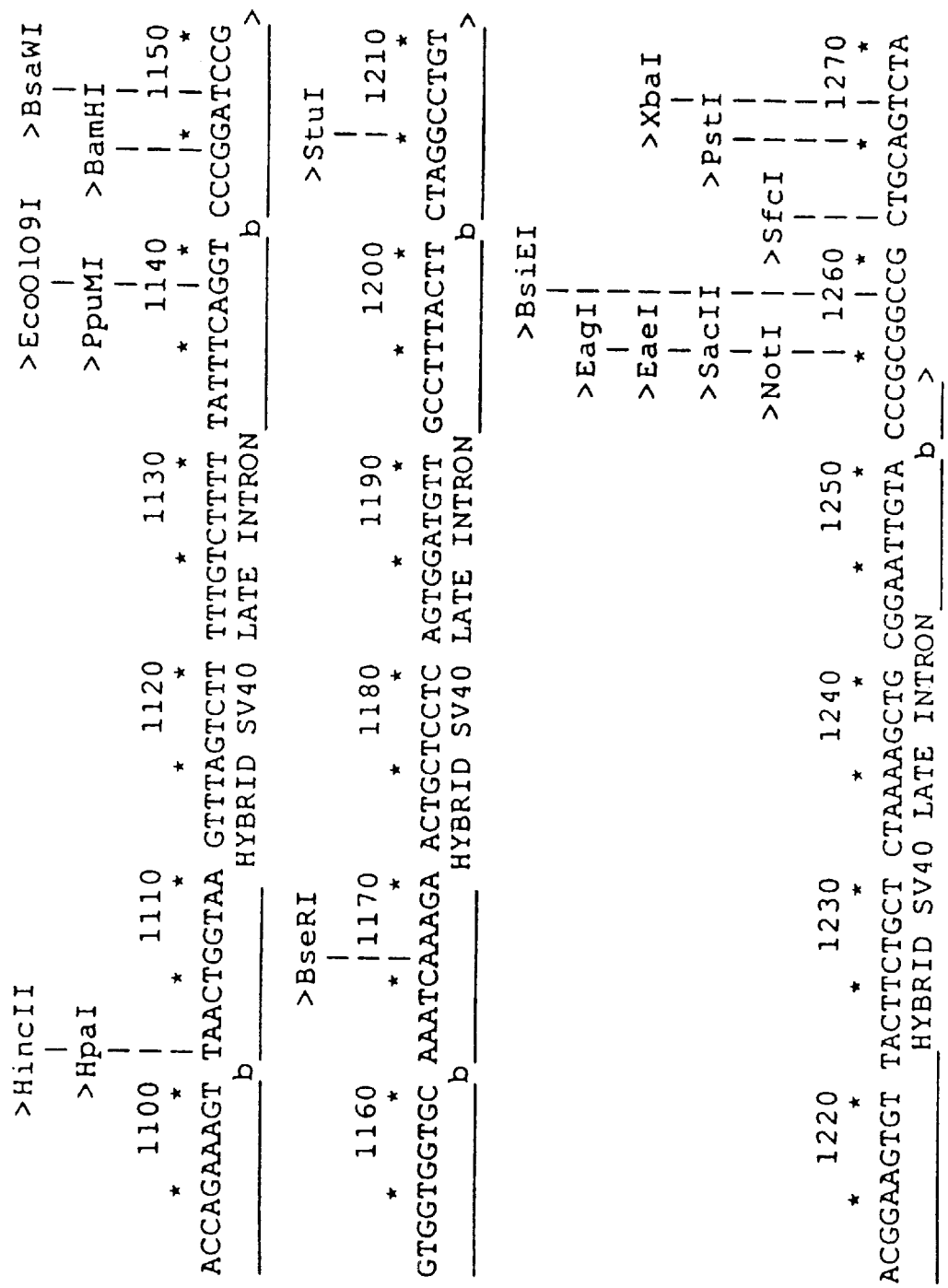
FIG. 6 depicts the nucleotide sequence of pCTMI.
FIG. 7 is a diagrammatic representation of plasmid pCT-MIE.
Figures 6, 7, 8, 9, 10, 11, 12, 13, 14, 15, 16, 17:
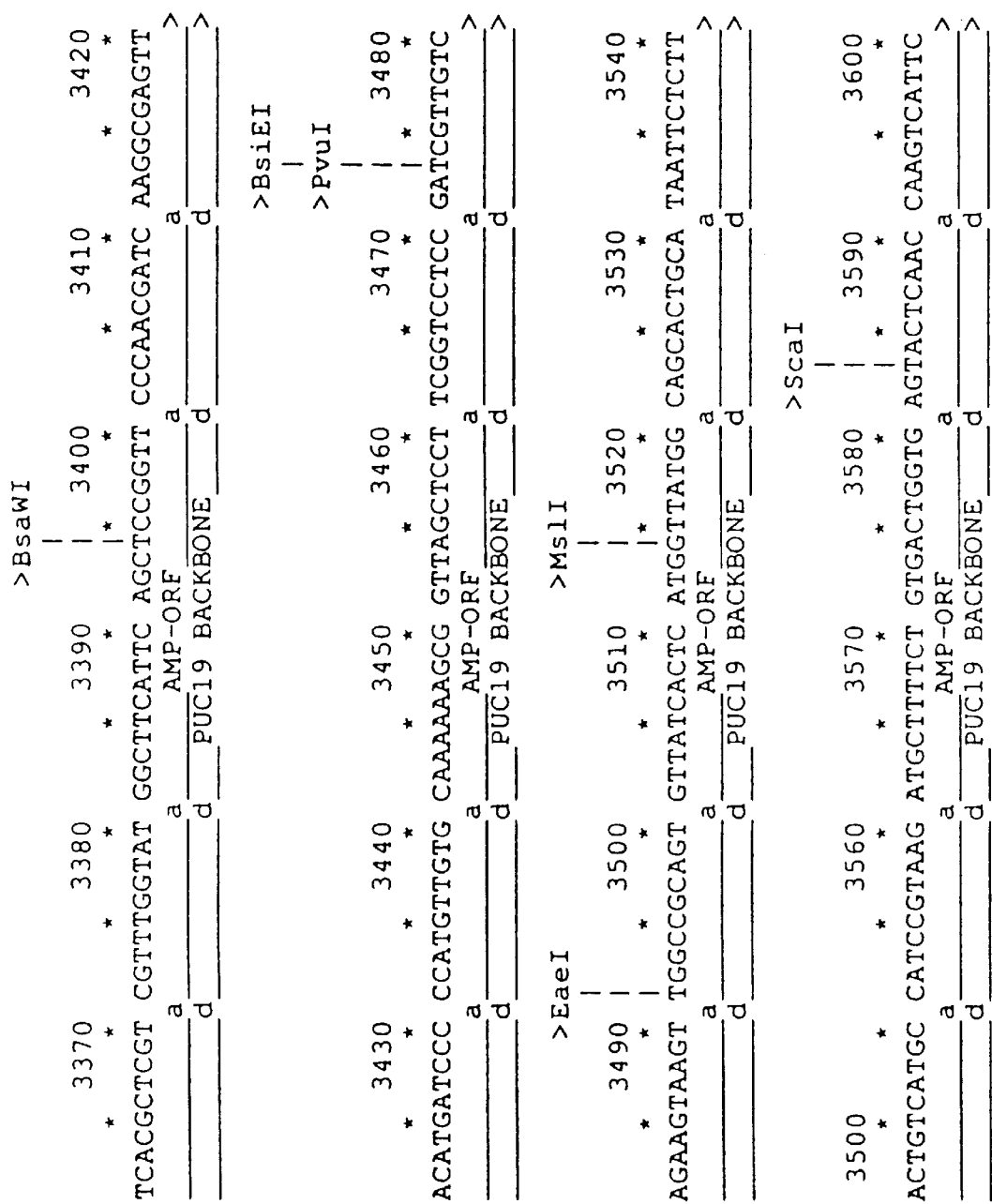
FIG. 8 (SEQ ID NO:33–46) depicts the nucleotide sequence of pCTMIE.
FIG. 9 is a diagram depicting E2F-RB fusion constructs used in the examples. All E2F constructs commenced at amino acid 95 and lacked part of the cyclin A binding domain. E2F-437 contained the DNA binding domain (black), heterodimerization domain (white), and the transactivation domain (stippled). E2F-194 contained solely the DNA binding domain. E2F-286 contained the DNA binding domain and the DP-1heterodimerization domain. To generate E2F-194-RB56-5s and E2F-286-RB56-5s, the E2F constructs were fused in-frame to codon 379 of RB. C706F is an inactivating point mutation.
FIG. 10 is a diagram depicting transcriptional repression by E2F-RB fusion constructs.
FIGS. 11(A–D) depicts expression of E2F-RB fusion proteins in mammalian cell lines. Extracts were prepared from cells used in E2-CAT reporter assays or in FACS assays and analyzed with an anti-RB monoclonal antibody. In panel A, the results are shown from C33A cells transfected with (3) RB56-H209, (4) RB56 wild-type, (5) RB56-5s, (6) E2F286-5s, (7) E2F194-5s, (8) E2F194, (9) E2F286, (10) E2F437. Lane (1) is an RB56 protein standard. Lane (2)
Figure 7:
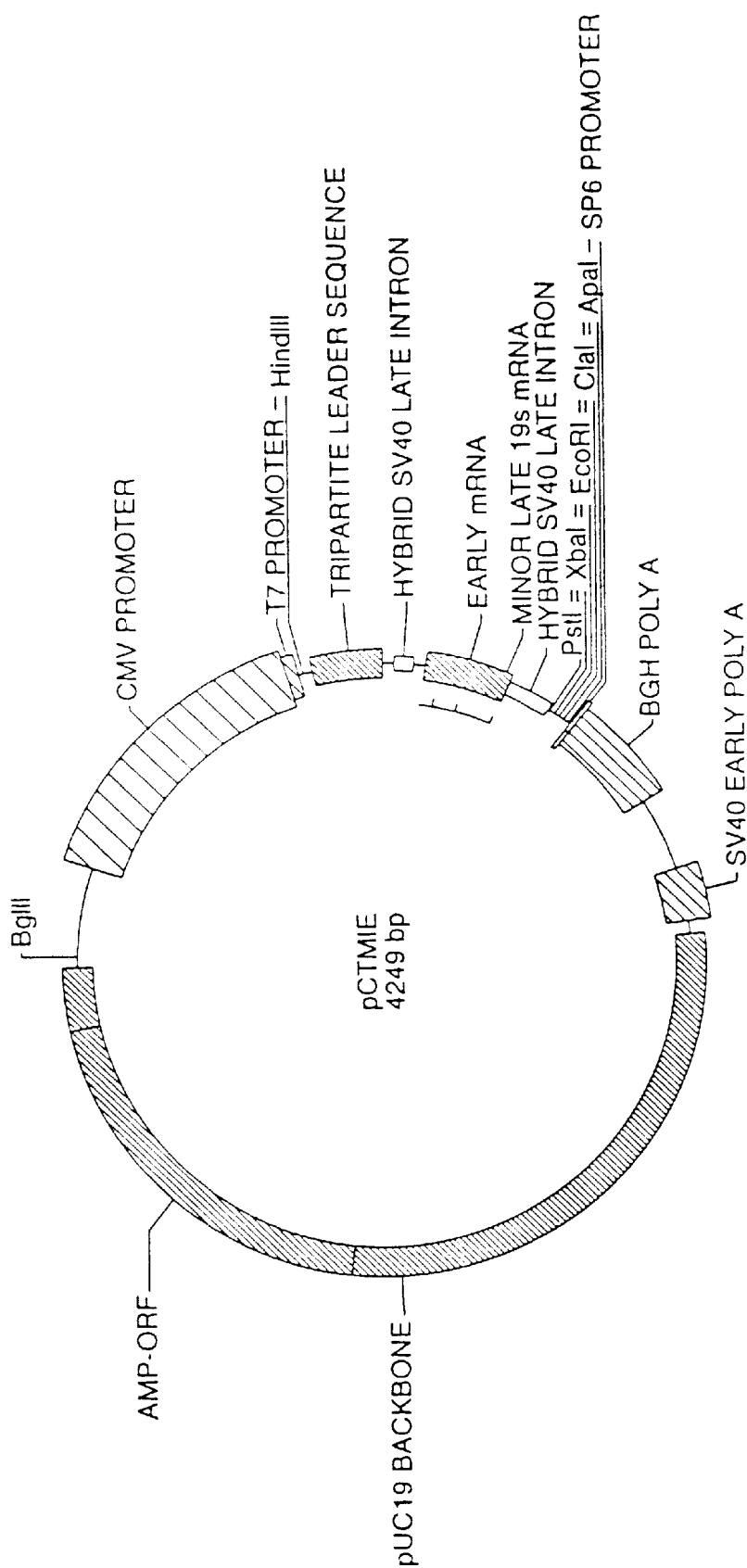
Figure 8:
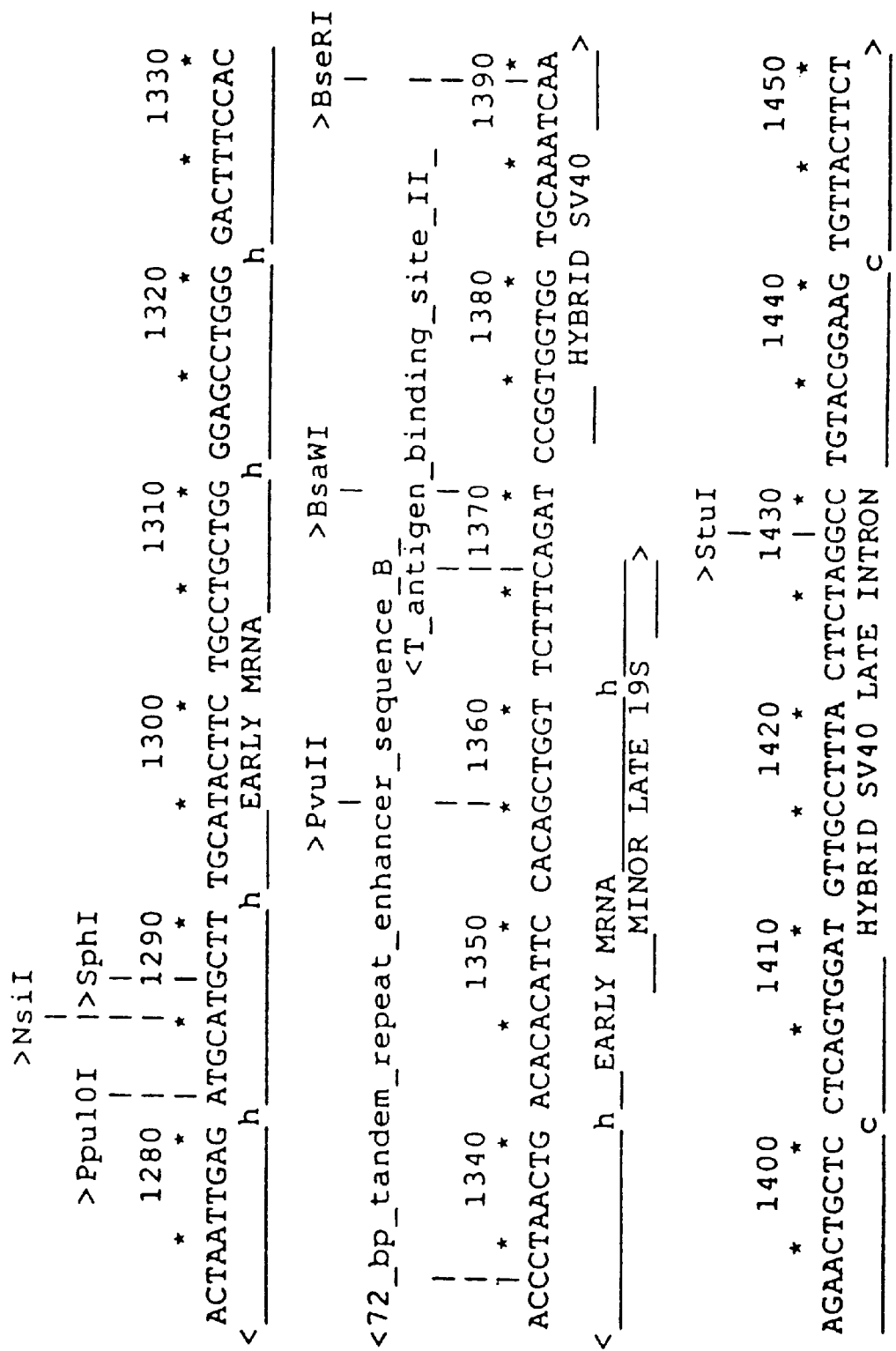
Figures 8, 9, 10, 11, 12, 13, 14, 15, 16, 17:
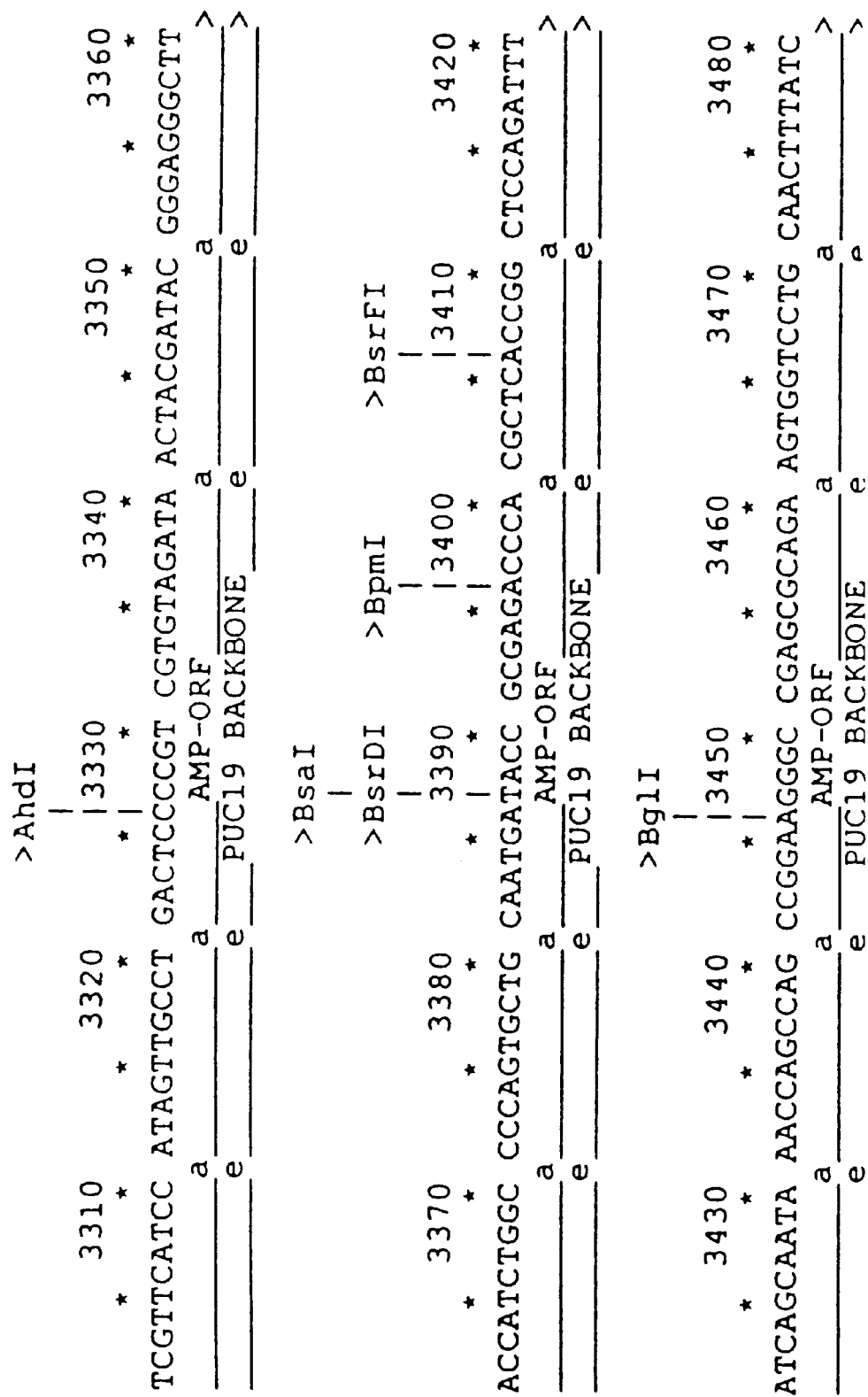
Figure 9:
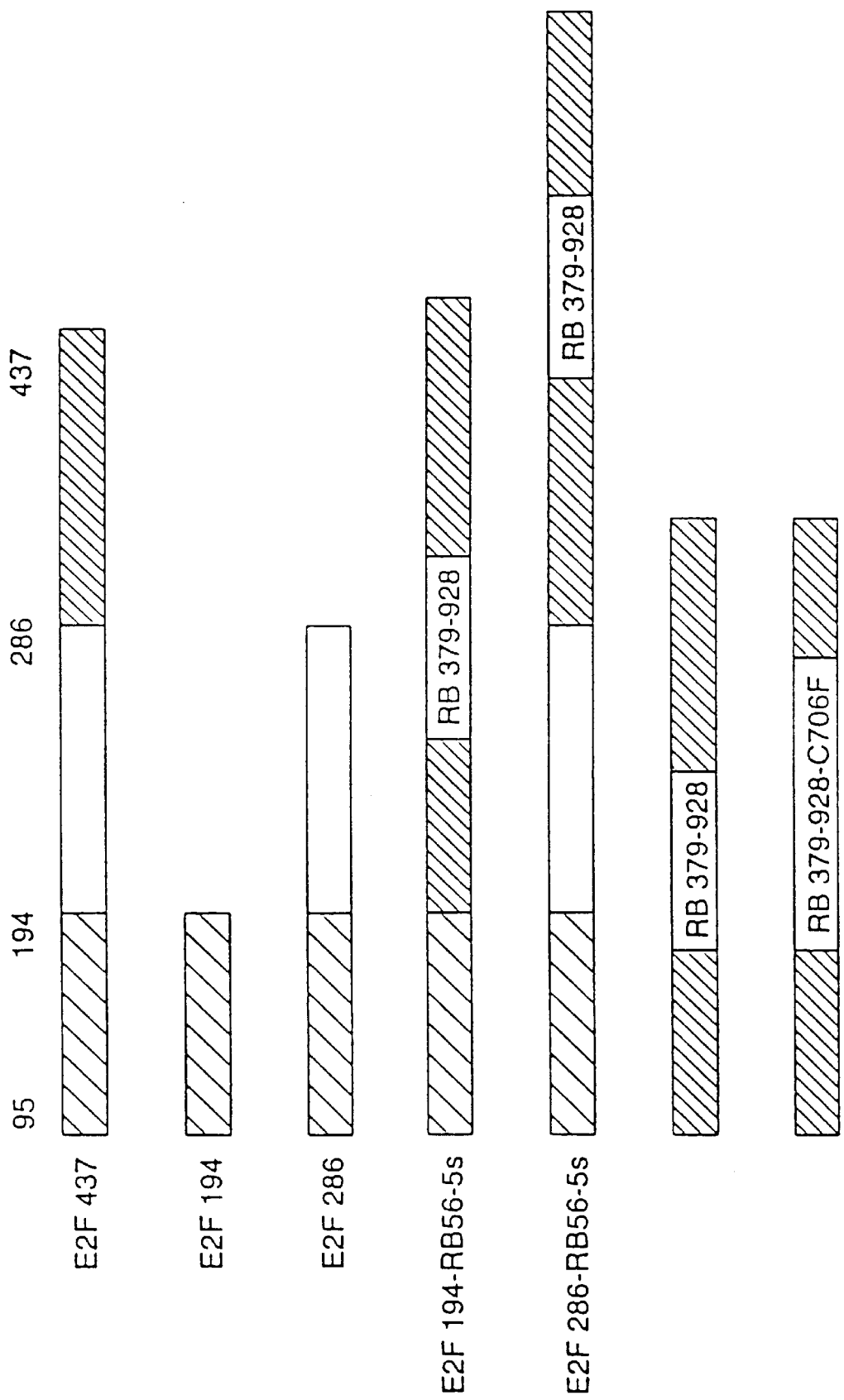
Figure 10:
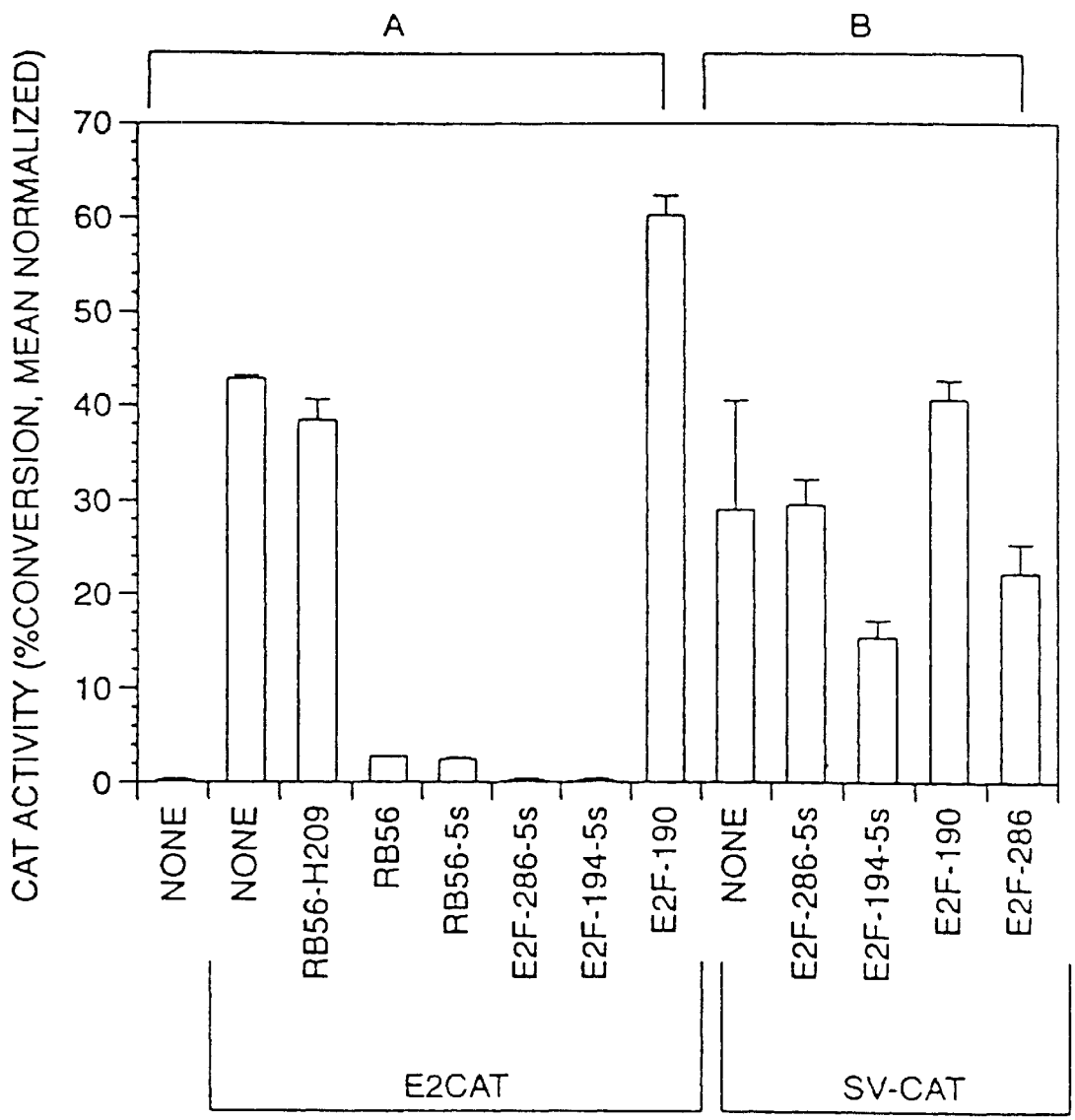
Figure 11:
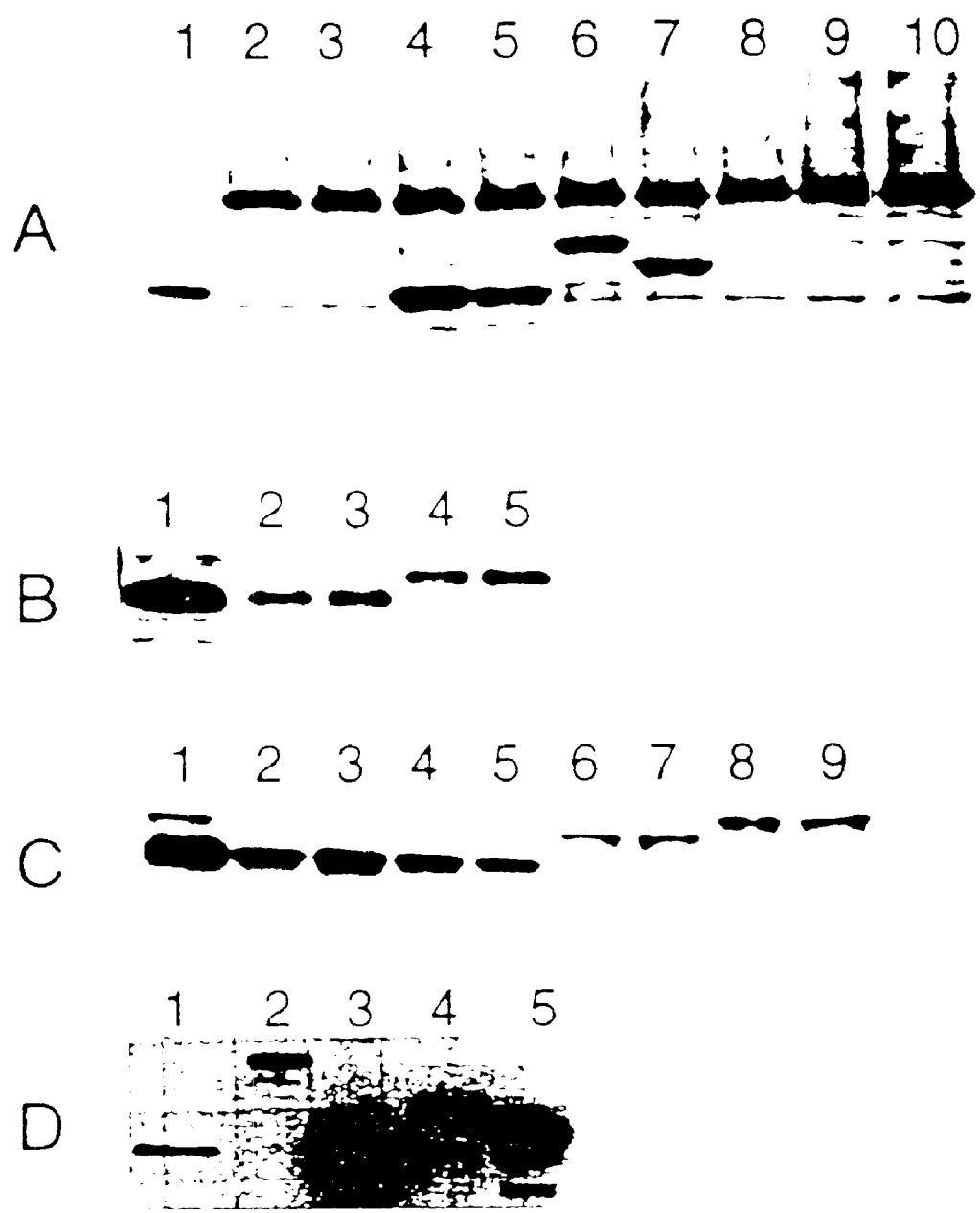
Figure 12:
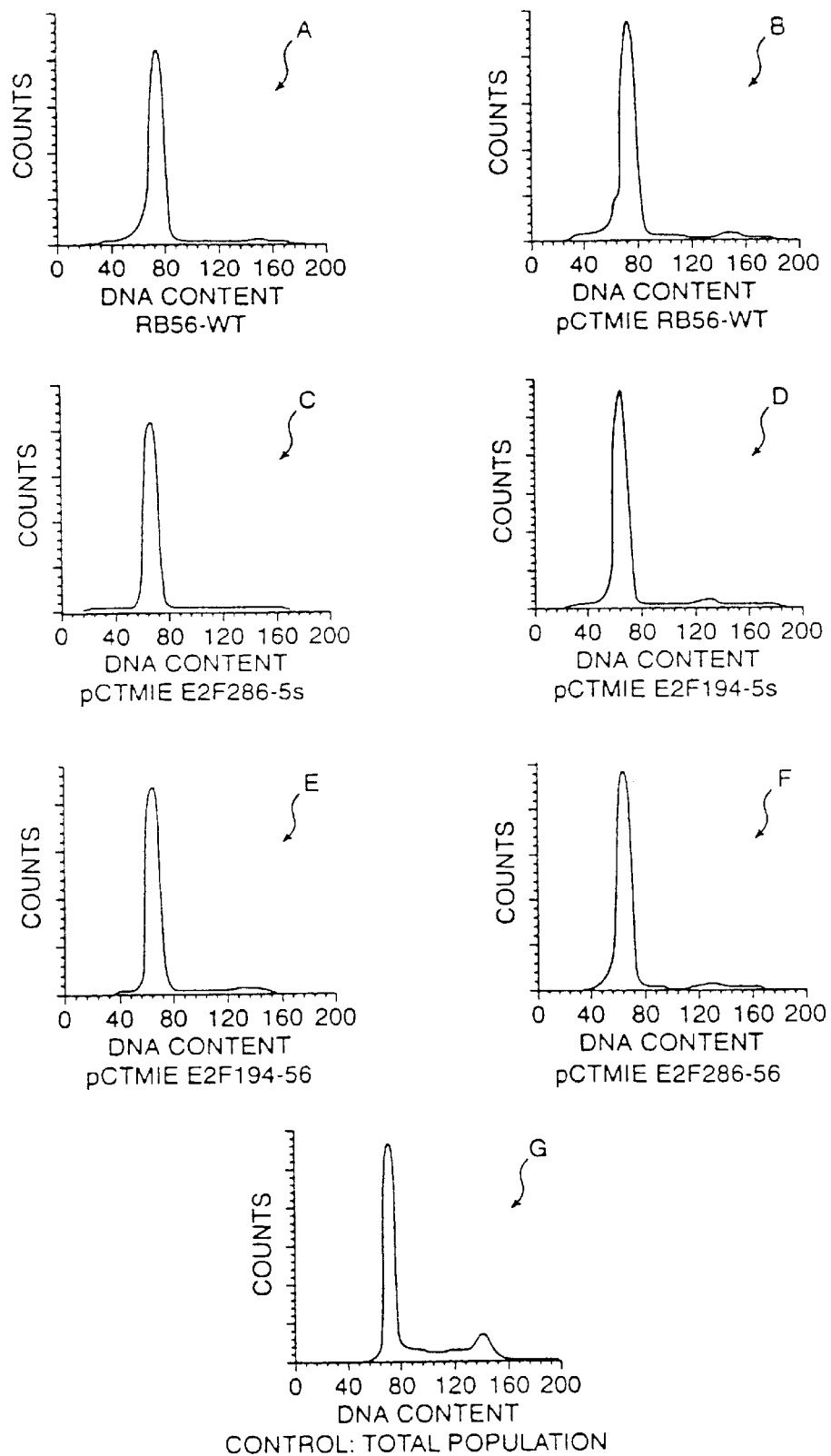
Figure 13A:
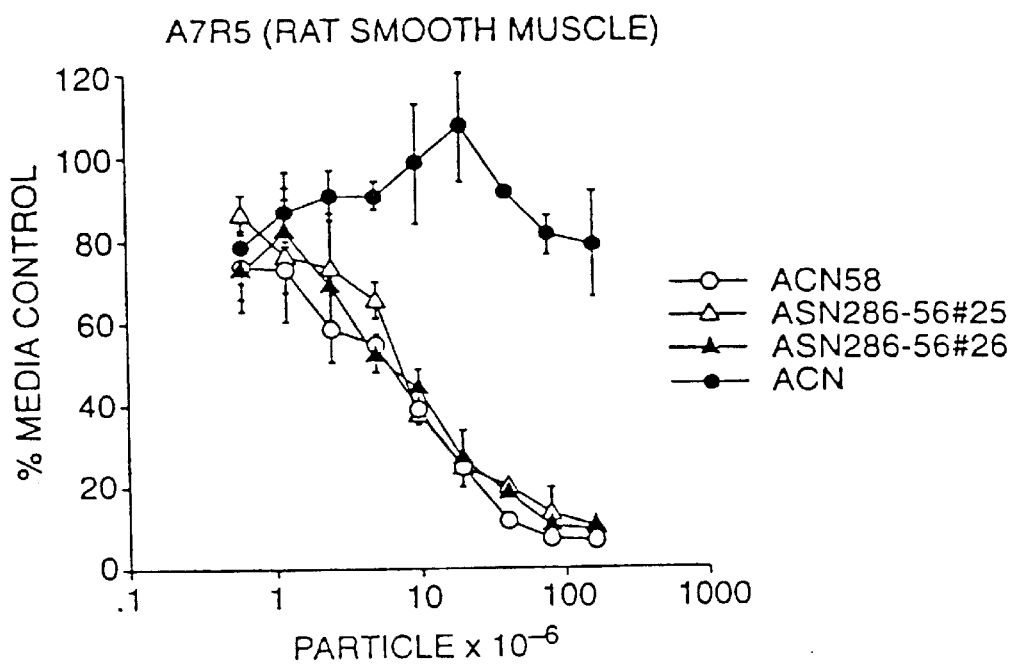
Figure 13B:
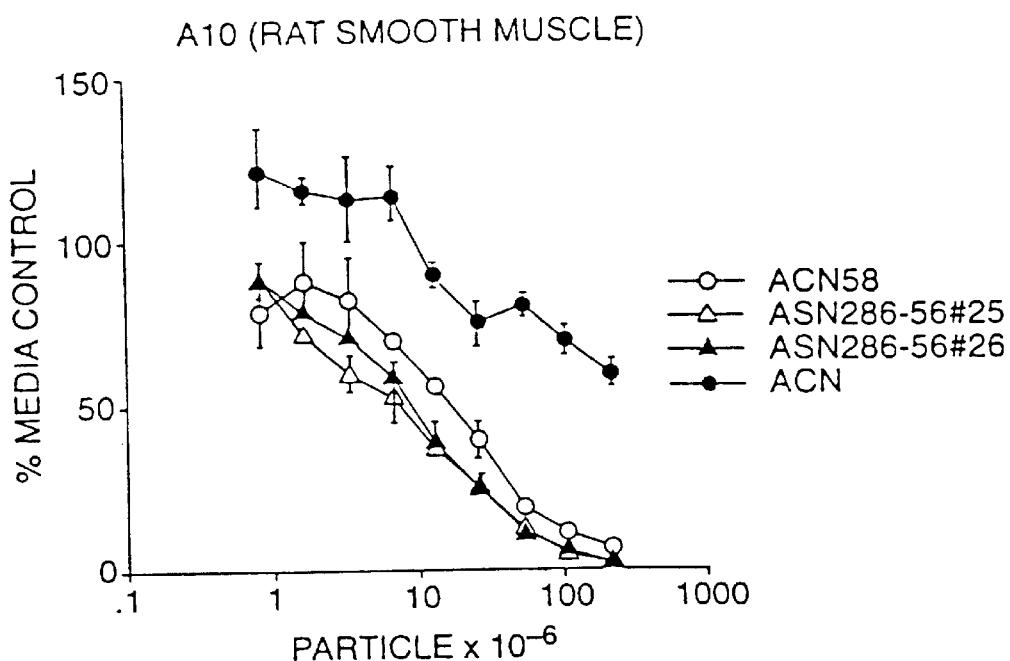
Figure 14A:
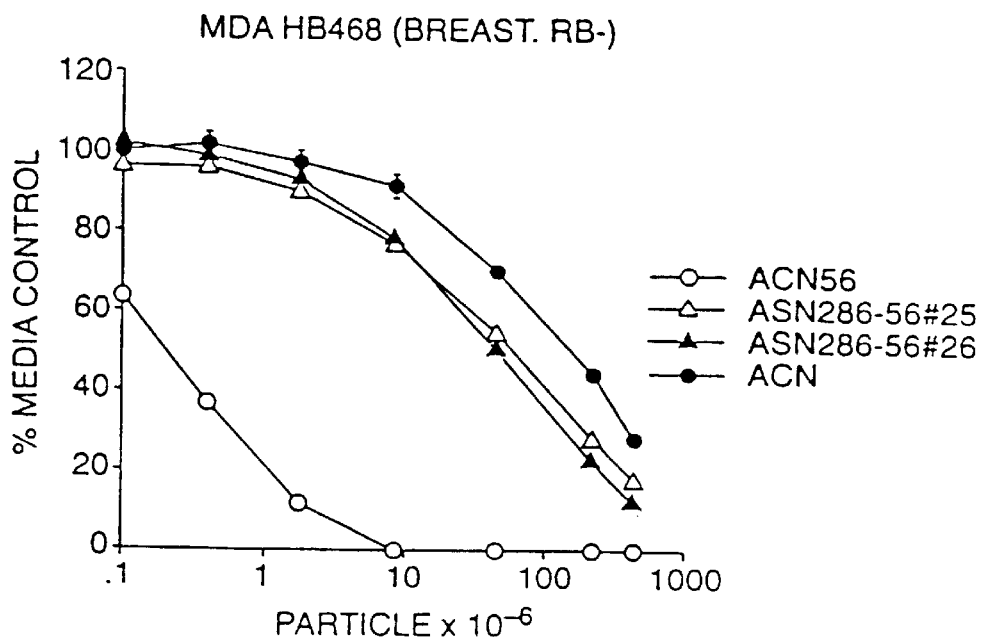
Figure 14B:
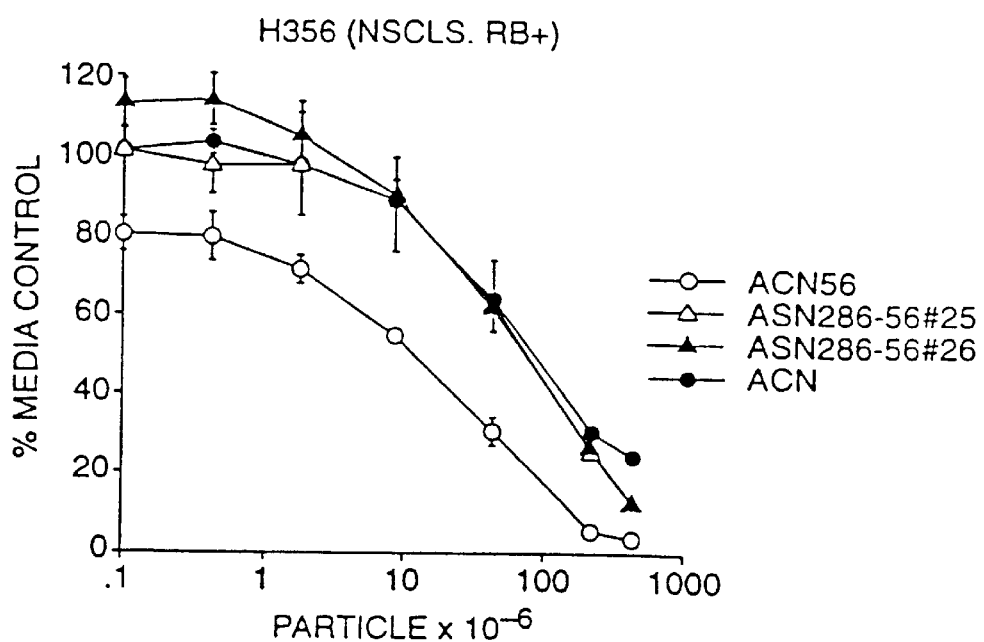
Figure 15:
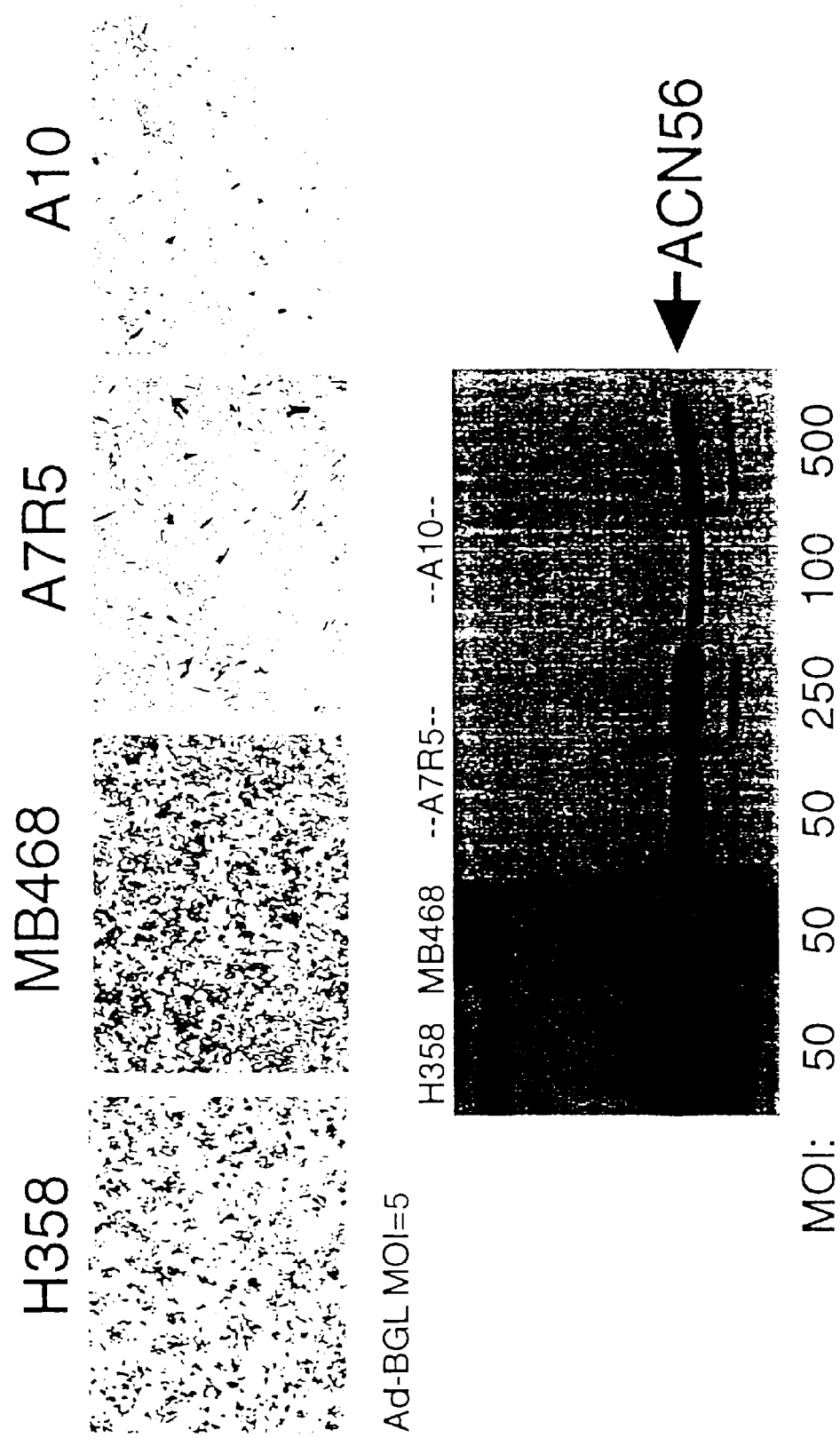
Figure 16:
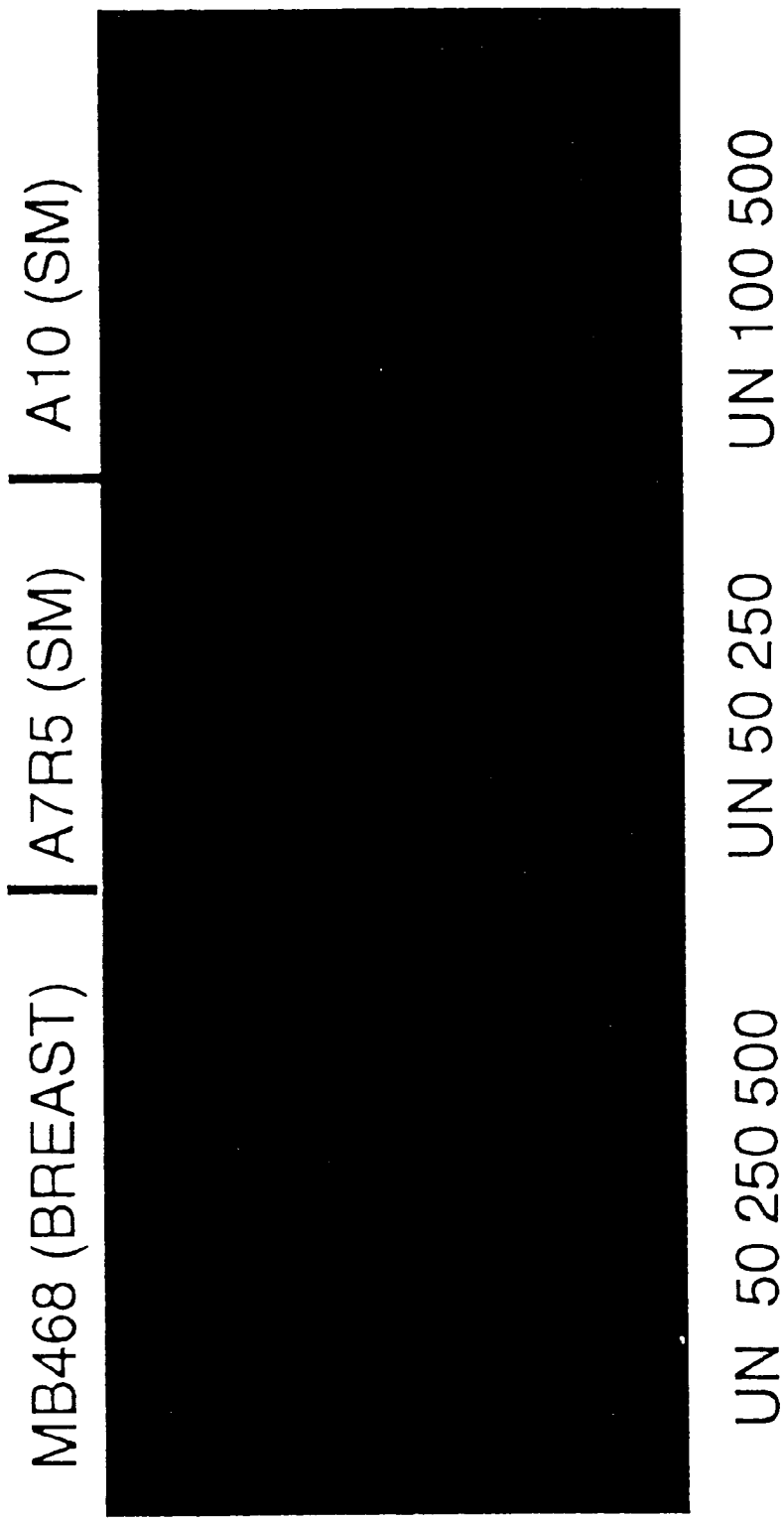
Figure 17:
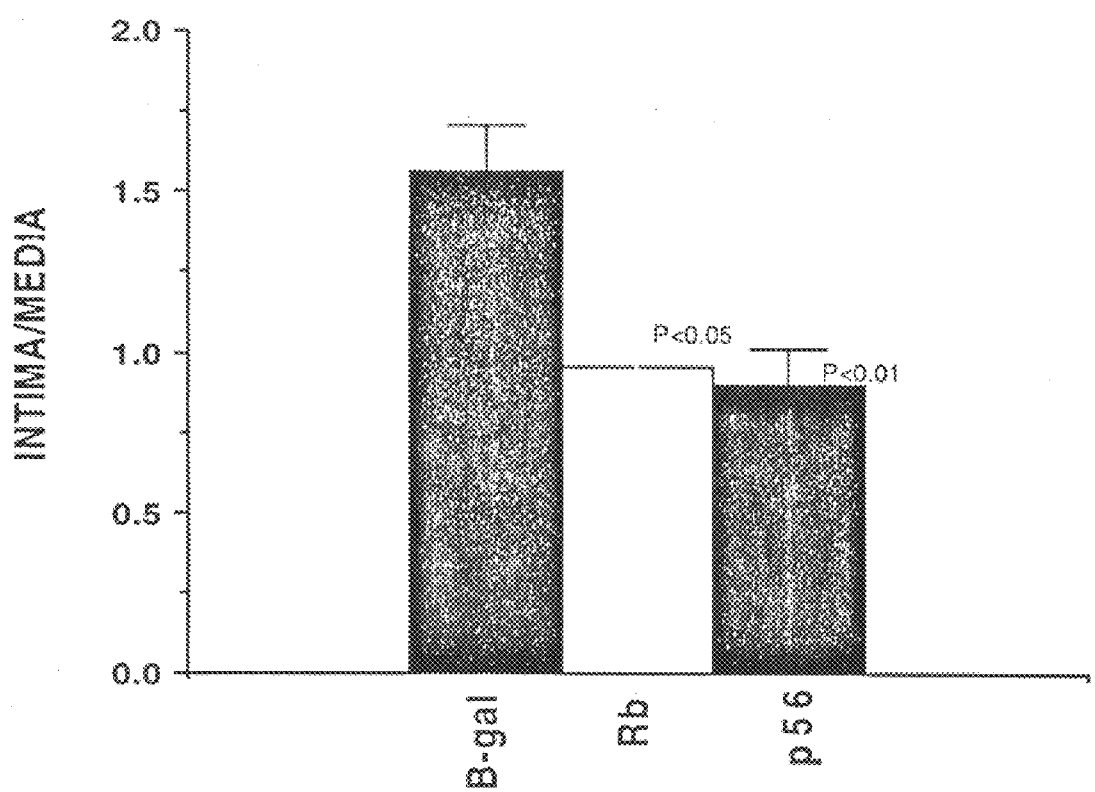

FIG. 12 depicts histogram analyses of flow cytometry of RB-expressing NIH-3T3 cells.

FIG. 13, panel A, depicts a comparison of the effects of a CMV-driven recombinant adenovirus (ACN56) with two isolates of a human smooth muscle alpha actin-driven E2F-p56 fusion construct consisting of amino acids 95 through 286 of E2F linked directly and in-frame to p56 (amino acids 379–928 of RB cDNA), vs. a control virus (ACN) in a $^3$H-thymidine uptake assay in the rat smooth muscle cell line A7R5. Panel (B) depicts the effects of the same constructs in the rat smooth muscle cell line A10.

FIG. 14 depicts a comparison of the effects of the viruses described in FIG. 13 in non-muscle cells. Panel (A) depicts results in the breast carcinoma cell line MDA MB468. Panel (B) depicts results in the non-small cell lung cell carcinoma line H358.

FIG. 15, top panel, depicts the relative infectivity by adenovirus of different cell lines as judged by the level of β-galactosidase (β-gal) staining following infection with equal amounts of a recombinant adenovirus expressing β-gal driven by a CMV promoter. H358 is non-small lung cell carcinoma cell line; MB468 is a breast carcinoma cell line; A7R5 and A10 are smooth muscle cell lines. The lower portion of the figure depicts the relative levels of p56 protein expressed in the same cells when infected with the recombinant adenovirus ACN56, in which the p56 cDNA is driven by the non-tissue specific CMV promoter.

FIG. 16 depicts relative protein levels in cells infected with the smooth muscle alpha actin promoter-driven E2F-p56 fusion construct (ASN286-56). UN denoted uninfected; 50, 100, 250, and 500 refer to multiplicities of infection (MOI).

FIG. 17 is a bar graph depicting the ratio of intima to media area (as a measurement of the inhibition of neointima formation) from cross-sections (n=9) of rat carotid arteries which were injured and treated with recombinant adenoviruses expressing either β-gal, RB (ACNRB) or p56 (ACN56), all under the control of the CMV promoter.

Figure 18:
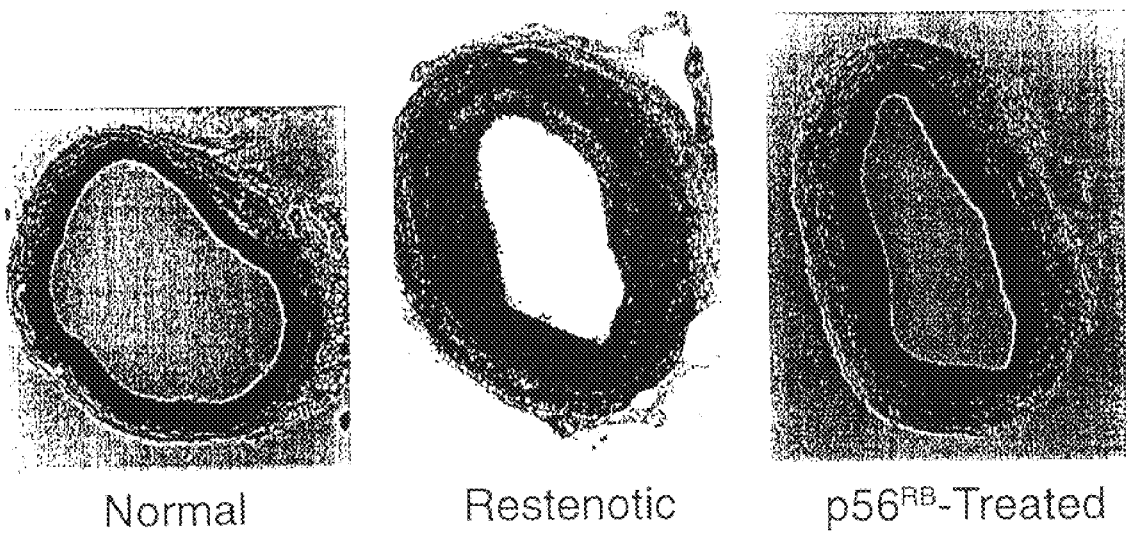

FIG. 18 is a series of three photographs depicting restenosis in a rat angioplasty model. The panel on the left depicts data from a normal animal; the central panel depicts data from an animal injured and then treated with a β-gal expressing recombinant virus; the panel on the right depicts data from an animal injured and then treated with a recombinant adenovirus expressing p56 (ACN56).

Figure 19:
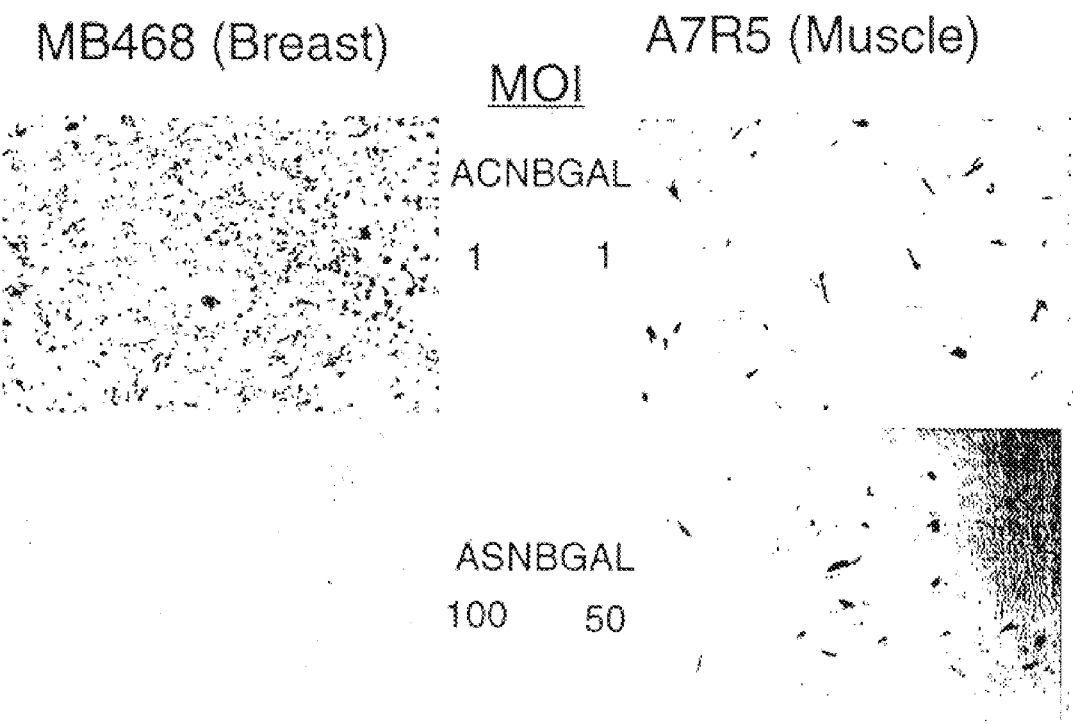

FIG. 19 depicts tissue-specificity of the smooth muscle alpha actin promoter, as demonstrated by its selective ability to express the β-gal transgene in muscle cells but not non-muscle cells. The panels on the left compare β-gal expression in the breast cell carcinoma line MB468 infected with either an MOI=1 with a CMV-driven β-gal (ACNBGAL) vs an MOI=100 with the smooth muscle promoter construct (ASNBGAL). The panels on the right show β-gal expression of the rat smooth muscle cell line A7R5 infected with either an MOI=1 of ACNBGAL or an MOI=50 of ASNBGAL. Expression from ASNBGAL is seen in the muscle cell line, but absent in the non-muscle cell line, despite the higher degree of infectivity of the cells.

Figure 20:
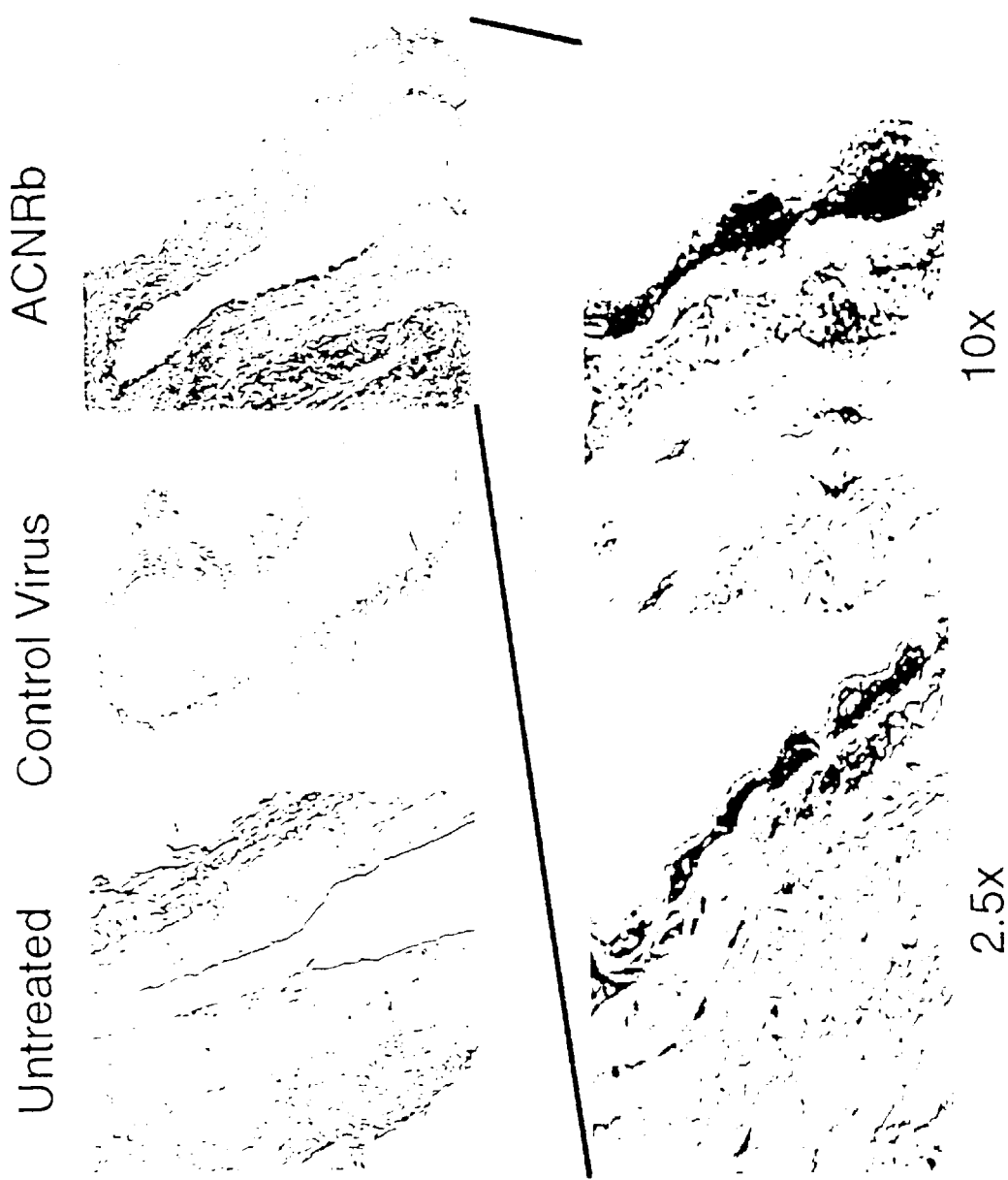

FIG. 20 depicts the ability of recombinant adenovirus expressing RB to transduce rat carotid arteries. Recombinant adenovirus-treated arteries (1×10$^9$ pfu) were harvested two days following balloon injury and infection. Cross sections were fixed and an RB specific antibody was used to detect the presence of RB protein in the tissue. The control virus used was ACN. RB protein staining was evident in the ACNRB treated sample, especially at higher magnifications.

Figure 21A:
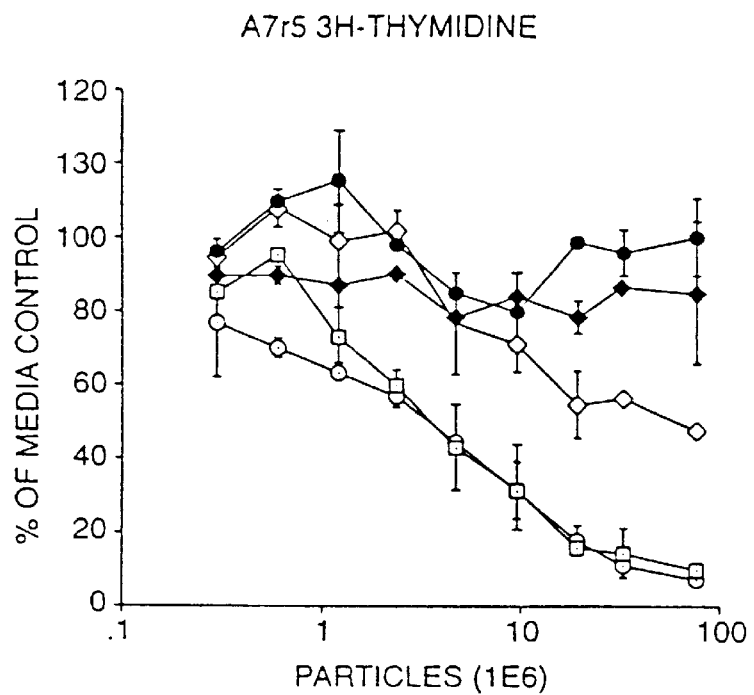
Figure 21B:
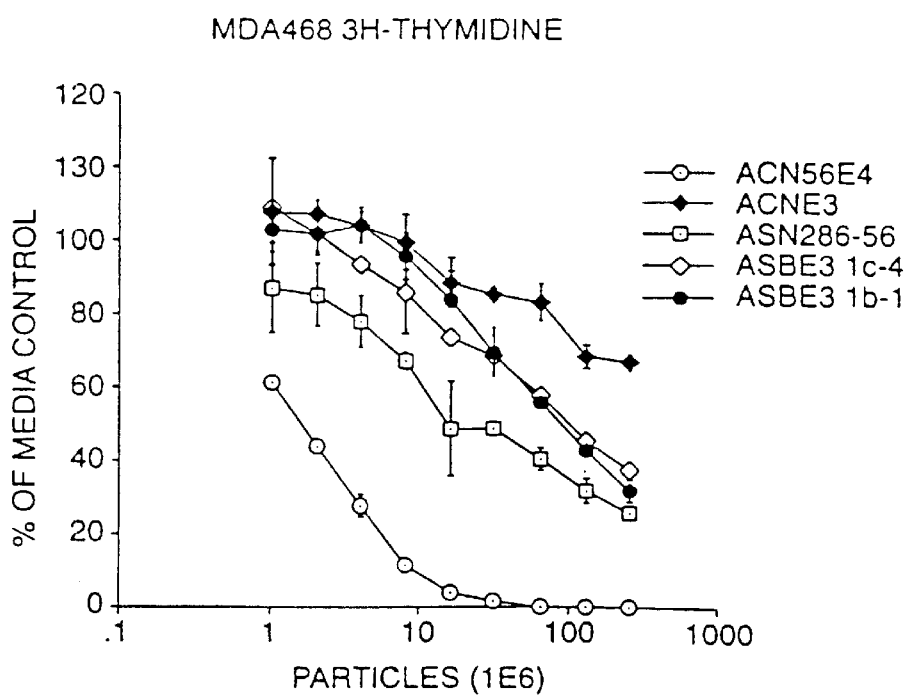

FIG. 21 depicts a comparison of the effects of a CMV-driven p56 recombinant adenovirus (ACN56E4) vs a human smooth muscle alpha-actin promoter-driven E2F-p56 fusion construct (ASN286-56) vs control adenoviral constructs containing either the CMV or smooth muscle alpha-actin promoters without a downstream transgene (ACNE3 or ASBE3-2 isolates shown, respectively). Assays were $^3$H-thymidine uptake either in a smooth muscle cell line (A7R5) or a non-muscle cell line (MDA-MB468, breast carcinoma). Results demonstrated muscle tissue specificity using the smooth muscle alpha-actin promoter and specific inhibition by both the p56 and E2F-p56 transgenes relative to their respective controls.

DESCRIPTION OF THE PREFERRED EMBODIMENT

The instant invention provides RB fusion constructs including fusion polypeptides and vectors encoding them, and methods for the use of such constructs in the treatment of hyperproliferative diseases. In some preferred embodiments of the invention, an RB polypeptide is fused to an E2F polypeptide. Any E2F species can be used, typically E2F-1, -2, -3, -3, or -5 (see, e.g., Wu et al. *Mol Cell. Biol.* 15:2536–2546 (1995); Ivey-Hoyle et al. *Mol. Cell. Biol.* 13:7802 (1993); Vairo et al. *Genes and Dev.* 9:869 (1995); Beijersbergen et al. *Genes and Dev.* 8:2680 (1994)); Ginsberg et al. *Genes and Dev.* 8:2665 (1994); Buck et al. *Oncogene* 11:31 (1995)), more typically E2F-1. Typically, the EF2 polypeptide comprises at least the DNA binding domain of E2F, and may optionally include the cyclin A binding domain, the heterodimerization domain, and/or the transactivation domain. Preferably, the cyclin A binding domain is not functional. The nucleotide and amino acid sequence of E2F referred to herein are those of Genbank HUME2F, shown in FIGS. 1A and 1B. Nucleic acid, preferably DNA, encoding such an EF2 polypeptide is fused in reading frame to an RB polypeptide. The RB polypeptide can be any RB polypeptide, including conservative amino acid variants, allelic variants, amino acid substitution, deletion, or insertion mutants, or fragments thereof. Preferably, the growth suppression domain, i.e., amino acids residues 379–928, of the RB polypeptide is functional (Hiebert, et al. *MCB* 13:3384–3391 (1993); Qin, et al. *Genes and Dev.* 6:953–964 (1992)). In some embodiments, wild-type pRB110 is used. More preferably, a truncated version of RB, RB56, is used. RB56 comprises amino acid residues 379–928 of pRB110 (Hiebert, et al. *MCB* 13:3384–3391 (1993); Qin, et al. *Genes and Dev.* 6:953–964 (1992)). In some embodiments, amino acid variants of RB at positions 2, 608, 612, 788, 807, or 811, are used singly or in combination. The variant RB56-5s comprises wild-type RB56 having alanine substitutions at 608, 612, 788, 807, and 811. Numbering of RB amino acids and nucleotides is according to the RB sequence disclosed by Lee, et al. (*Nature* 329:642–645 (1987)), hereby incorporated by reference in its entirety for all purposes. (FIG. 2).

Nucleic acids encoding the polypeptides of the invention can be DNA or RNA. The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein. It is further understood that the sequence includes the degenerate codons of the native sequence or sequences which may be introduced to provide codon preference in a specific host cell.

The term "vector" as used herein refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome. A vector contains multiple genetic elements positionally and sequentially oriented, i.e., operatively linked with other necessary elements such that nucleic acid in the vector encoding the constructs of the invention can be transcribed, and when necessary, translated in transfected cells.

The term "gene" as used herein is intended to refer to a nucleic acid sequence which encodes a polypeptide. This definition includes various sequence polymorphisms, mutations, and/or sequence variants wherein such alterations do not affect the function of the gene product. The term "gene" is intended to include not only coding sequences but also regulatory regions such as promoters, enhancers, and termination regions. The term further includes all introns and other DNA sequences spliced from the mRNA transcript, along with variants resulting from alternative splice sites.

The term "plasmid" refers to an autonomous circular DNA molecule capable of replication in a cell, and includes both the expression and nonexpression types. Where a recombinant microorganism or cell culture is described as hosting an "expression plasmid", this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein. The terms "protein" and "polypeptide" are used interchangeably herein.

In general, a construct of the invention is provided in an expression vector comprising the following elements linked sequentially at appropriate distances for functional expression: a tissue-specific promoter, an initiation site for transcription, a 3' untranslated region, a 5' MRNA leader sequence, a nucleic acid sequence encoding a polypeptide of the invention, and a polyadenylation signal. Such linkage is termed "operatively linked." Enhancer sequences and other sequences aiding expression and/or secretion can also be included in the expression vector. Additional genes, such as those encoding drug resistance, can be included to allow selection or screening for the presence of the recombinant vector. Such additional genes can include, for example, genes encoding neomycin resistance, multi-drug resistance, thymidine kinase, beta-galactosidase, dihydrofolate reductase (DHFR), and chloramphenicol acetyl transferase.

In the instant invention, tissue-specific expression of the RB constructs of the invention is preferably accomplished by the use of a promoter preferentially used by a tissue of interest. Examples of tissue-specific promoters include the promoter for creatine kinase, which has been used to direct the expression of dystrophin cDNA expression in muscle and cardiac tissue (Cox, et al. *Nature* 364:725–729 (1993)) and immunoglobulin heavy or light chain promoters for the expression of suicide genes in B cells (Maxwell, et al. *Cancer Res.* 51:4299–4304 (1991)). An endothelial cell-specific regulatory region has also been characterized (Jahroudi, et al. *Mol. Cell. Biol.* 14:999–1008 (1994)). Amphotrophic retroviral vectors have been constructed carrying a herpes simplex virus thymidine kinase gene under the control of either the albumin or alpha-fetoprotein promoters (Huber, et al. *Proc. Natl. Acad. Sci. U.S.A.* 88:8039–8043 (1991)) to target cells of liver lineage and hepatoma cells, respectively. Such tissue specific promoters can be used in retroviral vectors (Hartzoglou, et al. *J. Biol. Chem.* 265:17285–17293 (1990)) and adenovirus vectors (Friedman, et al. *Mol. Cell. Biol.* 6:3791–3797 (1986); Wills et al. *Cancer Gene Therapy* 3:191–197 (1995)) and still retain their tissue specificity.

In the instant invention, a preferred promoter for tissue-specific expression of exogenous genes is the human smooth muscle alpha-actin promoter. Reddy, et al. (*J. Cell Biology* 265:1683–1687 (1990)) disclosed the isolation and nucleotide sequence of this promoter, while Nakano, et al. (*Gene* 99:285–289 (1991)) disclosed transcriptional regulatory elements in the 5' upstream and the first intron regions of the human smooth muscle (aortic type) alpha-actin gene.

Petropoulos, et al. (*J. Virol.* 66:3391–3397 (1992)) disclosed a comparison of expression of bacterial chloramphenicol transferase (CAT) operatively linked to either the chicken skeletal muscle alpha actin promoter or the cytoplasmic beta-actin promoter. These constructs were provided in a retroviral vector and used to infect chicken eggs.

Exemplary tissue-specific expression elements for the liver include but are not limited to HMG-CoA reductase promoter (Luskey, *Mol. Cell. Biol.* 7(5):1881–1893 (1987)); sterol regulatory element 1 (SRE-1; Smith et al. *J. Biol. Chem.* 265(4):2306–2310 (1990); phosphoenol pyruvate carboxy kinase (PEPCK) promoter (Eisenberger et al. *Mol. Cell Biol.* 12(3):1396–1403 (1992)); human C-reactive protein (CRP) promoter (Li et al. *J. Biol. Chem.* 265(7): 4136–4142 (1990)); human glucokinase promoter (Tanizawa et al. *Mol. Endocrinology* 6(7):1070–81 (1992); cholesterol 7-alpha hydroylase (CYP-7) promoter (Lee et al. *J. Biol. Chem.* 269(20):14681–9 (1994)); beta-galactosidase alpha-2,6 sialyltransferase promoter (Svensson et al. *J. Biol. Chem.* 265(34):20863–8 (1990); insulin-like growth factor binding protein (IGFBP-1) promoter (Babajko et al. *Biochem Biophys. Res. Comm.* 196 (1):480–6 (1993)); aldolase B promoter (Bingle et al. *Biochem J.* 294(Pt2):473–9 (1993)); human transferrin promoter (Mendelzon et al. *Nucl. Acids Res.* 18(19):5717–21 (1990); collagen type I promoter (Houglum et al. *J. Clin. Invest.* 94(2):808–14 (1994)).

Exemplary tissue-specific expression elements for the prostate include but are not limited to the prostatic acid phosphatase (PAP) promoter (Banas et al. *Biochim. Biophys. Acta*. 1217(2):188–94 (1994); prostatic secretory protein of 94 (PSP 94) promoter (Nolet et al. *Biochim. Biophys. ACTA* 1089(2):247–9 (1991)); prostate specific antigen complex promoter (Kasper et al. *J. Steroid Biochem. Mol. Biol.* 47 (16):127–35 (1993)); human glandular kallikrein gene promoter (hgt-1) (Lilja et al. *World J. Urology* 11(4):188–91 (1993).

Exemplary tissue-specific expression elements for gastric tissue include but are not limited to the human $H^+/K^+$-ATPase alpha subunit promoter (Tamura et al. *FEBS Letters* 298:(2–3):137–41 (1992)).

Exemplary tissue-specific expression elements for the pancreas include but are not limited to pancreatitis associated protein promoter (PAP) (Dusetti et al. *J. Biol. Chem.* 268(19):14470–5 (1993)); elastase 1 transcriptional enhancer (Kruse et al. *Genes and Development* 7(5):774–86 (1993)); pancreas specific amylase and elastase enhancer promoter (Wu et al. *Mol. Cell. Biol.* 11(9):4423–30 (1991); Keller et al. *Genes & Dev.* 4(8):1316–21 (1990)); pancreatic cholesterol esterase gene promoter (Fontaine et al. *Biochemistry* 30(28):7008–14 (1991)).

Exemplary tissue-specific expression elements for the endometrium include but are not limited to the uteroglobin promoter (Helftenbein et al. *Annal. NY Acad. Sci.* 622:69–79 (1991)).

Exemplary tissue-specific expression elements for adrenal cells include but are not limited to cholesterol side-chain cleavage (SCC) promoter (Rice et al. *J. Biol. Chem.* 265:11713–20 (1990).

Exemplary tissue-specific expression elements for the general nervous system include but are not limited to gamma-gamma enolase (neuron-specific enolase, NSE) promoter (Forss-Petter et al. *Neuron* 5(2):187–97 (1990)).

Exemplary tissue-specific expression elements for the brain include but are not limited to the neurofilament heavy chain (NF-H) promoter (Schwartz et al. *J. Biol. Chem.* 269(18):13444–50 (1994)).

Exemplary tissue-specific expression elements for lymphocytes include but are not limited to the human CGL1/granzyme B promoter (Hanson et al. *J. Biol. Chem.* 266 (36):24433–8 (1991)); the terminal deoxy transferase (TdT), lambda 5, VpreB, and lck (lymphocyte specific tyrosine protein kinase p56lck) promoter (Lo et al. *Mol. Cell. Biol.* 11(10):5229–43 (1991)); the humans CD2 promoter and its 3'transcriptional enhancer (Lake et al. *EMBO J.* 9(10): 3129–36 (1990)), and the human NK and T cell specific activation (NKG5) promoter (Houchins et al. *Immunogenetics* 37(2):102–7 (1993)).

Exemplary tissue-specific expression elements for the colon include but are not limited to pp60c-src tyrosine kinase promoter (Talamonti et al. *J. Clin. Invest* 91(1):53–60 (1993)); organ-specific neoantigens (OSNs), mw 40 kDa (p40) promoter (Ilantzis et al. *Microbiol. Immunol.* 37(2): 119–28 (1993)); colon specific antigen-P promoter (Sharkey et al. *Cancer* 73(3 supp.) 864–77 (1994)).

Exemplary tissue-specific expression elements for breast cells include but are not limited to the human alpha-lactalbumin promoter (Thean et al. *British J. Cancer.* 61(5): 773–5 (1990)).

Other elements aiding specificity of expression in a tissue of interest can include secretion leader sequences, enhancers, nuclear localization signals, endosmolytic peptides, etc. Preferably, these elements are derived from the tissue of interest to aid specificity.

Techniques for nucleic acid manipulation of the nucleic acid sequences of the invention such as subcloning nucleic acid sequences encoding polypeptides into expression vectors, labelling probes, DNA hybridization, and the like are described generally in Sambrook et al., *Molecular Cloning—A Laboratory Manual* (2nd Ed.), Vol. 1–3, Cold Spring Harbor Laboratory, Cold Spring Harbor, N.Y., (1989), which is incorporated herein by reference. This manual is hereinafter referred to as "Sambrook et al."

Once DNA encoding a sequence of interest is isolated and cloned, one can express the encoded proteins in a variety of recombinantly engineered cells. It is expected that those of skill in the art are knowledgeable in the numerous expression systems available for expression of DNA encoding. No attempt to describe in detail the various methods known for the expression of proteins in prokaryotes or eukaryotes is made here.

In brief summary, the expression of natural or synthetic nucleic acids encoding a sequence of interest will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of polynucleotide sequence of interest. To obtain high level expression of a cloned gene, it is desirable to construct expression plasmids which contain, at the minimum, a strong promoter to direct transcription, a ribosome binding site for translational initiation, and a transcription/translation terminator. The expression vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems. See Sambrook et al.

The E2F-RB fusion constructs of the invention can be introduced into the tissue of interest in vivo or ex vivo by a variety of methods. In some embodiments of the invention, the nucleic acid, preferably DNA, is introduced to cells by such methods as microinjection, calcium phosphate precipitation, liposome fusion, or biolistics. In further embodiments, the DNA is taken up directly by the tissue of interest. In other embodiments, the constructs are packaged into a viral vector system to facilitate introduction into cells.

Viral vector systems useful in the practice of the instant invention include adenovirus, herpesvirus, adenoassociated virus, minute virus of mice (MVM), HIV, sindbis virus, and retroviruses such as Rous sarcoma virus, and MoMLV. Typically, the constructs of the instant invention are inserted into such vectors to allow packaging of the E2F-RB expression construct, typically with accompanying viral DNA, infection of a sensitive host cell, and expression of the E2F-RB gene. A particularly advantageous vector is the adenovirus vector disclosed in Wills, et al. *Human Gene Therapy* 5:1079–1088 (1994).

In still other embodiments of the invention, the recombinant DNA constructs of the invention are conjugated to a cell receptor ligand for facilitated uptake (e.g., invagination of coated pits and internalization of the endosome) through a DNA linking moiety (Wu, et al. *J. Biol. Chem.* 263:14621–14624 (1988); WO 92/06180). For example, the DNA constructs of the invention can be linked through a polylysine moiety to asialo-oromucocid, which is a ligand for the asialoglycoprotein receptor of hepatocytes.

Similarly, viral envelopes used for packaging the constructs of the invention can be modified by the addition of receptor ligands or antibodies specific for a receptor to permit receptor-mediated endocytosis into specific cells (e.g., WO 93/20221, WO 93/14188; WO 94/06923). In some embodiments of the invention, the DNA constructs of the invention are linked to viral proteins, such as adenovirus particles, to facilitate endocytosis (Curiel, et al. *Proc. Natl. Acad. Sci. U.S.A.* 88:8850–8854 (1991)). In other embodiments, molecular conjugates of the instant invention can include microtubule inhibitors (WO 94/06922); synthetic peptides mimicking influenza virus hemagglutinin (Plank, et al. *J. Biol. Chem.* 269:12918–12924 (1994)); and nuclear localization signals such as SV40 T antigen (WO 93/19768).

In some embodiments of the invention, the RB polypeptides of the invention are administered directly to a patient in need of treatment. A "therapeutically effective" dose is a dose of polypeptide sufficient to prevent or reduce severity of a hyperproliferative disorder. As used herein, the term "hyperproliferative cells" includes but is not limited to cells having the capacity for autonomous growth, i.e., existing and reproducing independently of normal regulatory mechanisms. Hyperproliferative diseases may be categorized as pathologic, i.e., deviating from normal cells, characterizing for constituting disease, or may be categorized as non-pathologic, i.e., deviation from normal but not associated with a disease state. Pathologic hyperproliferative cells are characteristic of the following disease states: restenosis, diabetic retinopathy, thyroid hyperplasia, Grave's disease, psoriasis, benign prostatic hypertrophy, Li-Fraumeni syndrome including breast cancer, sarcomas and other neoplasms, bladder cancer, colon cancer, lung cancer, various leukemias and lymphomas. Examples of non-pathological hyperproliferative cells are found, for instance, in mammary ductal epithelial cells during development of lactation and also in cells associated with wound repair. Pathological hyperproliferative cells characteristically exhibit loss of contact inhibition and a decline in their ability to selectively adhere which implies a further breakdown in intercellular communication. These changes include stimulation to divide and the ability to secrete proteolytic enzymes.

The constructs of the invention are useful in the therapy of various cancers and other conditions in which the administration of RB is advantageous, including but not limited to peripheral vascular diseases and diabetic retinopathy. Although any tissue can be targeted for which some tissue-specific expression element, such as a promoter, can be identified, of particular interest is the tissue-specific administration of an RB construct for hyperproliferative disorders such as restenosis, for which the smooth muscle actin promoter is preferable.

The compositions of the invention will be formulated for administration by manners known in the art acceptable for administration to a mammalian subject, preferably a human. In some embodiments of the invention, the compositions of the invention can be administered directly into a tissue by injection or into a blood vessel supplying the tissue of interest. In further embodiments of the invention the compositions of the invention are administered "locoregionally", i.e., intravesically, intralesionally, and/or topically. In other embodiments of the invention, the compositions of the invention are administered systemically by injection, inhalation, suppository, transdermal delivery, etc. In further embodiments of the invention, the compositions are administered through catheters or other devices to allow access to a remote tissue of interest, such as an internal organ. The compositions of the invention can also be administered in depot type devices, implants, or encapsulated formulations to allow slow or sustained release of the compositions.

The invention provides compositions for administration which comprise a solution of the compositions of the invention dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may also be administered via liposomes. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule which binds to a desired target, such as antibody, or with other therapeutic or immunogenic compositions. Thus, liposomes either filled or decorated with a desired composition of the invention of the invention can delivered systemically, or can be directed to a tissue of interest, where the liposomes then deliver the selected therapeutic/immunogenic peptide compositions.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. *Ann. Rev. Biophys. Bioeng.* 9:467 (1980), U.S. Pat. Nos. 4,235,871, 4,501,728, 4,837, 028, and 5,019,369, incorporated herein by reference.

A liposome suspension containing a composition of the invention may be administered intravenously, locally, topically, etc. in a dose which varies according to, inter alia, the manner of administration, the composition of the invention being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more compositions of the invention of the invention, and more preferably at a concentration of 25%–75%.

For aerosol administration, the compositions of the invention are preferably supplied in finely divided form along with a surfactant and propellant. Typical percentages of compositions of the invention are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

The constructs of the invention can additionally be delivered in a depot-type system, an encapsulated form, or an implant by techniques well-known in the art. Similarly, the constructs can be delivered via a pump to a tissue of interest.

In some embodiments of the invention, the compositions of the invention are administered ex vivo to cells or tissues explanted from a patient, then returned to the patient. Examples of ex vivo administration of gene therapy constructs include Arteaga et al. *Cancer Research* 56(5):1098–1103 (1996); Nolta et al. *Proc Natl. Acad. Sci. USA* 93(6):2414–9 (1996); Koc et al. *Seminars in Oncology* 23(1):46–65 (1996); Raper et al. *Annals of Surgery* 223(2):116–26 (1996); Dalesandro et al. *J. Thorac. Cardi. Surg.* 111(2):416–22 (1996); and Makarov et al. *Proc. Natl. Acad. Sci. USA* 93(1):402–6 (1996).

In some embodiments of the invention, the constructs of the invention are administered to a cardiac artery after balloon angioplasty to prevent or reduce the severity of restenosis. The constructs of the invention can be used to coat the device used for angioplasty (see, for example, Willard, et al. *Circulation* 89:2190–2197 (1994); French, et al. *Circulation* 90:2402–2413 (1994)). In further embodiments, the fusion polypeptides of the invention can be used in the same manner.

The following examples are included for illustrative purposes and should not be considered to limit the present invention.

EXAMPLES

Example I

E2F-RB Fusions

A. Introduction

In this example, expression plasmids which encode different segments of E2F fused to RB56 polypeptide were constructed. RB56 is a subfragment of full length RB which contains the "pocket" domains necessary for growth suppression (Hiebert, et al. *MCB* 13:3384–3391 (1993); Qin, et al. *Genes and Dev.* 6:953–964 (1992)). E2F194 contains E2F amino acids 95–194. This fragment contains only the DNA binding domain of E2F. E2F286 contains the DNA binding domain and the DP-1 heterodimerization domain. Both E2F fragments lack the N-terminal cyclin A-kinase binding domain, which appears to down-regulate the DNA binding activity of E2F (Krek et al. *Cell* 83:1149–1158 (1995); Krek et al. *Cell* 78:161–172 (1994)).

B. Construction of Vectors

Figure 3:
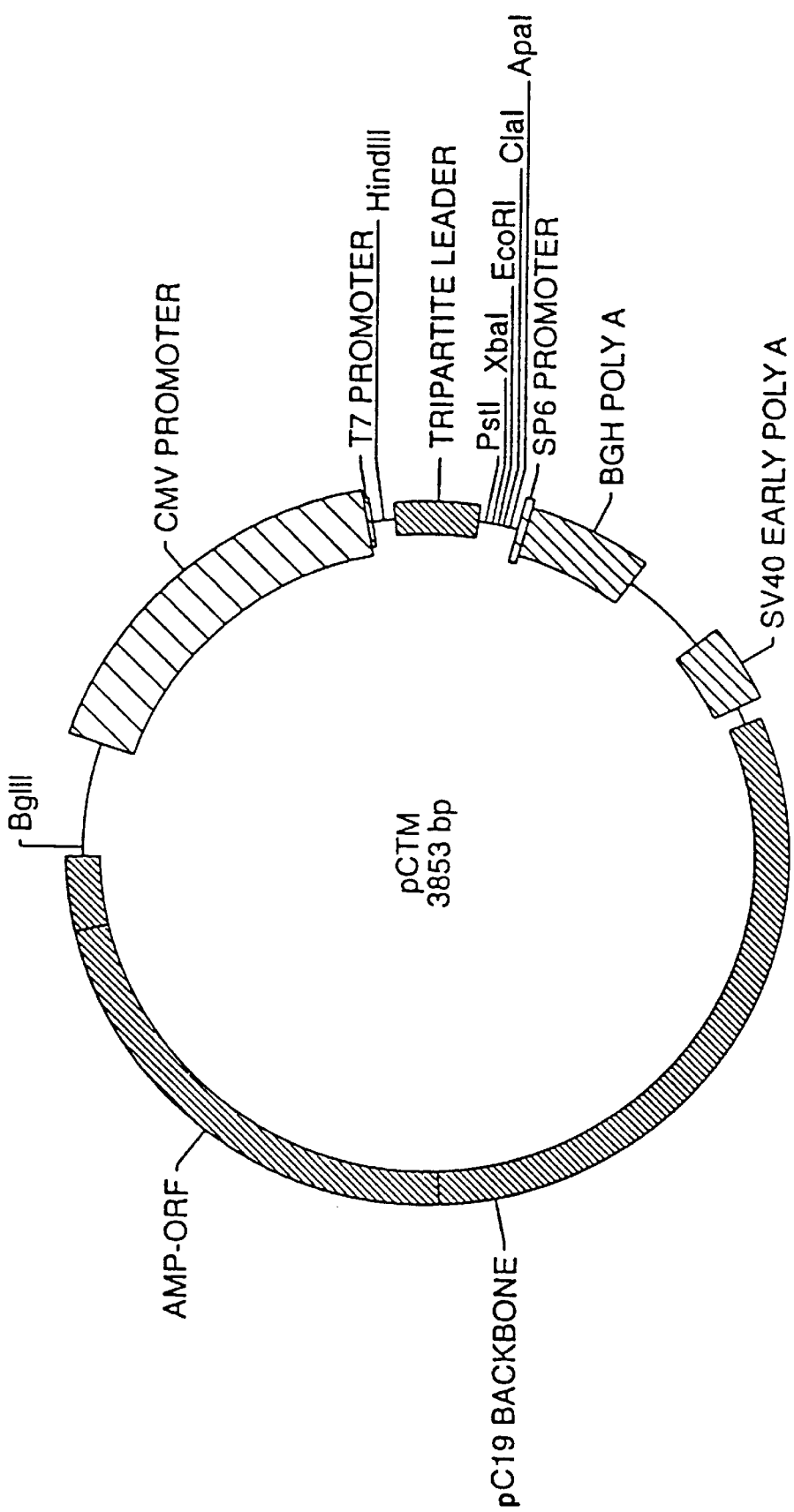
FIG. 3 is a diagrammatic representation of PCTM.
Figure 5:
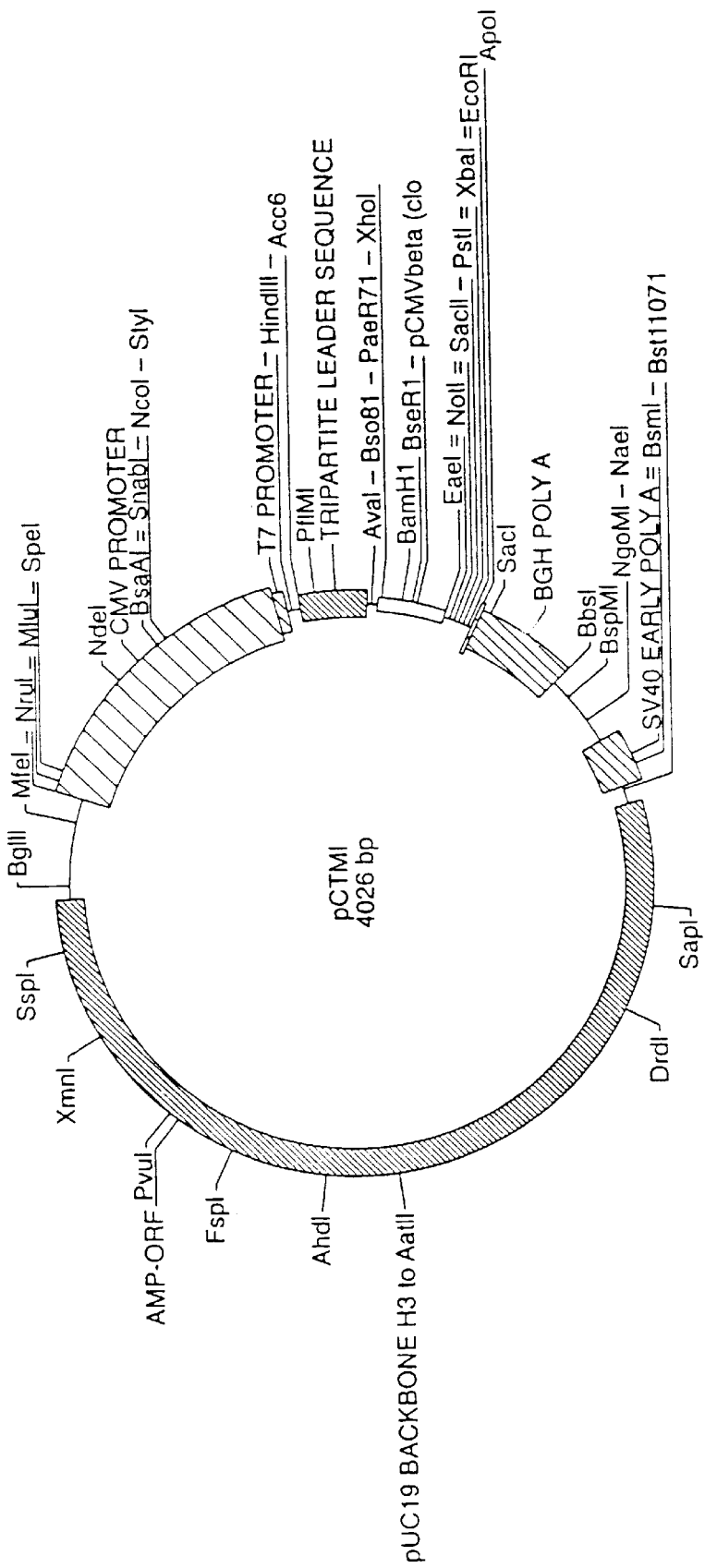
FIG. 5 is a diagrammatic representation of pCTMI.

Plasmid pCTM contains a CMV promoter, a tripartite adenovirus leader flanked by T7 and SP6 promoters, and a multiple cloning site with a bovine growth hormone (BGH) polyadenylation site and a SV-40 poly adenylation site downstream. A diagrammatic representation of pCTM is provided in FIG. 3. The DNA sequence for pCTM is provided in FIG. 4.

pCTMI was constructed from pCTM by digesting pCTM with Xho I and Not I and subcloning a 180 bp intron Xhol-Not I fragment from a pCMV-β-gal vector (Clonetech). A diagrammatic representation of pCTMI is provided in FIG. 5. The DNA sequence is provided in FIG. 6.

pCTMIE was constructed by amplifying the SV40 enhancer from SV40 viral DNA in a polymerase chain reaction. The amplified product was digested with BglII and inserted into BamH1-digested pCMTI and ligated in the presence of BamHI. The plasmid is depicted diagrammatically in FIG. 7. The DNA sequence is provided in FIG. 8.

PCTM-RB was prepared as follows. A 3.2 KB Xba I-Cla I fragment of pETRBc (Huang et al. *Nature* 350:160–162 (1991)) containing the full length human RB cDNA was ligated to Xba I-Cla I digested pCTM. pCTM-RB56 was prepared by ligating the digested pCTM to a 1.7 KB Xba 1-Cla I fragment containing the coding sequence for RB56. pCTMI-RB, pCTMIE-RB, pCTMI-RB56(amino acids 381–928) and pCTMIE-RB56(amino acids 381–928) were all constructed by the same methods.

C. RB-E2F fusion Constructs

FIG. 9 depicts the fusion constructs used in these studies. These E2F constructs commenced at amino acid 95 and lacked part of the cyclin A binding domain. E2F437 contained the DNA binding domain (black), heterodimerization domain (white) and transactivation domain (stippled). E2Fl94 contained solely the DNA binding domain. E2F286 contained the DNA binding domain and DP-1 heterodimerization domain. RB56-5s refers to an RB variant having alanine substitutions at amino acid residues 606, 612, 788, 807 and 811. In E2Fl94-RB56-5s and E2F286-RB56-5s, the E2F fragments were fused in frame to codon 379 of RB-5s. RB56-C706F contained an inactivating point mutation (Kaye et al. *Proc. Natl. Acad. Sci. U.S.A.* 87:6922–6926 (1990)).

pCMV-E2F194 and pCMV-E2F437 were constructed as follows. DNA encoding amino acids 95–194 of E2F (containing the DNA binding domain) or amino acids 95–437 was amplified in a polymerase chain reaction, digested with HindII, and ligated into SmaI/HindII digested pCMV-RB56 vectors. pCMVE2F286 was constructed by digesting pCMV-E2F437 with AflII, treating the ends with DNA pol I (Klenow fragment) and religating in the presence of AflII. The blunt end ligation created a stop codon at position 287. pCMV-E2F286-5s was constructed by ligating AflII (blunt)/HindIII digested pE2F437 to a Sal I (blunt)-HindIII fragment containing the RB56-5s coding sequence. pCTMIE-E2F194-5s and pCTMIE-E2F286-RB5s were constructed by ligating EcoRI-EcoRV digested pCTMIE (4.2 KB) to HindIII (blunt)-EcoRI fragments from either pCMV-E2F194-RB5s or pCMV-E2F286-RB5s.

D. Promoter Repression

To measure the effect of the E2F-RB fusion proteins, cervical carcinoma cell line C33A (ATCC # HTB-31) was transfected with equivalent amounts of E2F194-RB56 or E2F RB56 with an E2-CAT reporter plasmid (See, e.g., Weintraub et al. *Nature* 358:259–261 (1992)).

In the C33A assay, 250,000 C33A cells were seeded into each of well of 6-well tissue culture plates and allowed to adhere overnight. 5 µg each of pCMV-RB56, pCMV-E2F RB56, or pCMV-E2F plasmid were cotransfected (calcium phosphate method, MBS transfection kit, Stratagene) with 5 μg of indicated reporter construct E2-CAT or SVCAT) and 2.5 μg β-gal plasmid (pCMV-β, Clontech) per well into duplicate wells. Cells were harvested 72 hour after transfection and extracts were prepared.

In the 5637 assay, 250,000 5637 cells were seeded as described above. 1 μg each of RB or E2F-RB fusion plasmid, E2-CAT or SV-CAT reporter plasmid and pCMV-β-galactosidase were cotransfected using the lipofectin reagent (BRL, Bethesda, Md.) according to the manufacturer's instructions.

CAT assays were performed using either 20 μL (C33A) or 50 μL (5637) of cell extract (Gorman et al. Mol. Cell. Biol. 2:1044 (1982)). TLCs were analyzed on a Phosphoimager SF (Molecular Dynamics). CAT activities were normalized for transfection efficiency according to β-galactosidase activities of each extract. β-galactosidase activities of extracts were assayed as described by Rosenthal et al. (*Meth. Enzym.* 152:704 (1987)).

The results of these studies were as follows. Transfection of the E2-CAT reporter alone or in the presence of the nonfunctional control RB56-H209 mutant yielded relatively high CAT activity. Cotransfection of wild-type RB56 or the variant RB56-5s resulted in a 10 to 12 fold repression of CAT activity, indicating that RB56 or RB56-5s are both capable of efficiently repressing E2F-dependent transcription. E2F194-RB5s and E2F286-RB5s repressed transcription approximately 50 fold. Transcriptional repression required both the RB56 and the E2F components of the fusion proteins, as expression of E2F194 and E2F286 did not mediate transcriptional repression. No repression of SV40-CAT transcription occurred with E2F-RB constructs, thus demonstrating the specificity of the transcriptional repression by E2FRB for the E2 promoter. These results are depicted diagrammatically in FIG. 10.

E. Cell cycle arrest

The ability of E2F-RB fusion polypeptides to cause G1 arrest in Saos-2 (RB-/- cells) (ATCC # HTB-85) and C33A cells was investigated. Previous studies have shown that RB-mediated E2 promoter repression and G1 arrest are linked in Saos-2 cells but dissociated in C33A (RBmut) cells (Xu, et al. *PNAS* 92:1357–1361 (1992)). Cells were washed in PBS and were fixed in 1 mL −20° C. 70% ethanol for 30 minutes. Cells were collected by centrifugation and resuspended in 0.5 mL 2% serum containing 10 μg/ml RNase A and incubated for 30 minutes at 37° C. 0.5 mL of PBS containing propidium iodide (100 μg/ml) was added to each sample, mixed and cells were filtered through a FACS tube capstrainer. FACS analysis was performed on a FACS-Scan (Becton-Dickenson) using doublet discrimination. 5,000–10,000 CD20+ events were analyzed. Percent of cells in $G_0/G_1$, S, and $G_2/M$ was determined using Modfit modeling software.

The results of this experiment were as follows. Both full length RB110 and the truncated version RB56, but not the control mutant RB-H209, caused $G_1$ arrest in Saos-2 cells (Table 1). Similarly, the RB56-5s, E2F-194-RB56-5s and E2F286-RB56-5s all were capable of arresting cells in $G_0/G_1$. Transfection of the DNA binding domain, E2F194, did not block S-phase entry in Saos-2 as previously described for rodent cells (Dobrowolski, et al. *Oncogene* 9:2605–2612 (1994)). In contrast, RB110, RB56, and E2F-RB fusion proteins were not capable of arresting C33A cell lines indicating that the transcriptional repression observed in these cells does not translate into $G_1$ arrest.

The ability of the E2F-RB fusion proteins to arrest 5637 cells was also investigated (Table 2). RB56 and RB56-5s both efficiently arrested cells in $G_0/G_1$ (approximately 90% of cells in $G_0$–$G_1$), whereas E2F194-RB56-5s and E2F286-RB56-5s are slightly less efficient (about 80% of cells in $G_0/G_1$) at promoting $G_0/G_1$ arrest. Without being limited to any one theory, the less efficient arrest of both Saos-2 and 5637 cells by the E2F-RB fusion proteins appears due to the lower levels of steady-state protein produced in these cells (FIG. 11, panels b and c).

TABLE 1

Cell Cycle Regulation by RB and E2F-RB fusion proteins in RBneg cells

| | % Cells | | |
|---|---|---|---|
| | CD20+ | | |
| | $G_0/G_1$ | $G_2/M$ | S-phase |
| H209 | 52.1 | 27.1 | 20.8 |
| p56RB | 78.8 | 14.2 | 7.0 |
| p110RB | 70.9 | 14.3 | 14.8 |
| p56RB-5s | 84.8 | 13.2 | 2.0 |
| p56RB-p5 | 81.3 | 11.5 | 7.3 |
| E2F-194-5s | 77.8 | 14.9 | 7.3 |
| E2F-286-5s | 72.2 | 15.0 | 12.8 |
| E2F-194 | 49.9 | 28.0 | 22.1 |

TABLE 2

Growth Suppression of 5637 Bladder Cells by RB and E2F-RB fusion proteins

| | % Cells | | |
|---|---|---|---|
| 5637/CD20+ | $G_0/G_1$ | S | $G_2/M$ |
| CD20 | 59.7 | 16.9 | 20.6 |
| RB56-C706F | 57.4 | 16.3 | 24.3 |
| RB56WT | 90.7 | 4.12 | 4.88 |
| RB56-5s | 89.91 | 3.51 | 6.1 |
| E2F1 94-5s | 80.1 | 1.31 | 0 |
| E2F-286-5s | 79.21 | 8.1 | 0 |

F. Activity of Fusion Proteins in Functional RB Background

The activity of the E2F-RB fusion proteins in a cellular background containing functional RB was then determined. NIH-3T3 cells were transfected with RB56 or E2F-RB56fusions and stained with anti-RB monoclonal antibody 3C8 (Wen et al. *J. Immuno. Meth.* 169:231–240 (1994)). FACS analysis was performed of the RB expressing cells. The results are shown in FIG. 12. The non-gated population (g) shows the characteristic cell cycle distribution for NIH-3T3 cells (60% GO, 28% S, 10% G2/M). In contrast, in cells transfected with RB56 (a,b) or E2F-RB fusion proteins (c-f), greater than 90% of the RB-expressing cells were arrested in $G_0/G_1$. These data demonstrate that the ability of RB and E2F-RB56fusions to arrest cells in $G_0/G_1$ is not limited to RB negative tumor cells. The relative levels of protein expressed in transfected NIH-3T3 cells was also investigated. RB110 was not expressed efficiently in these cells.

Thus, these data demonstrate that E2F-RB fusion proteins are more efficient transcriptional repressors than either pRB or RB56 alone, and that RB can repress transcription by remaining bound to E2F rather than directly blocking the transactivation domain of E2F. These data support the use of E2F-RB fusions as RB agonists in both RB+ cells and in RB negative or RB mutant cells.

Example II
Tissue-Specific Expression of E2F-RB Fusions
A. Construction of Recombinant Adenovirus:

In this experiment, recombinant adenoviruses comprising an RB polypeptide under the control of a CMV or smooth muscle alpha actin promoter were generated.

The smooth muscle α-actin promoter (bases −670 through +5, Reddy et al. "Structure of the Human Smooth Muscle α-Actin Gene." *J. Biol. Chem.* 265:1683–1687 (1990), Nakano, et al. "Transcriptional Regulatory Elements In The 5' Upstream and First Intron Regions of The Human Smooth Muscle (aortic type) α-Actin-Encoding Gene." *Gene* 99:285–289 (1991) was isolated by PCR from a genomic library with 5' Xho I and Avr II and 3' Xba I, Cla I and Hind III restriction sites added for cloning purposes. The fragment was subcloned as an Xho 1, Hind III fragment into a plasmid for sequencing to verify base composition. A fusion construct 286-56 containing the DNA and heterodimerization domain of E2F-1 (bases 95–286) linked to p56 (amino acids 379–928 of full length RB) was subcloned as an Xba I, Cla I fragment directly downstream of the smooth muscle α-actin promoter, and this expression cassette was digested out and cloned into the plasmid pAd/ITR/IX- as an Xba I to AvrII, and Cla I fragment to create the plasmid pASN286-56. This plasmid consisted of the adenovirus type 5 inverted terminal repeat (ITR), packaging signals and Ela enhancer, followed by the human smooth muscle α-actin promoter and 286-56 cassette, and then Ad 2 sequence 4021–10462 (which contains the E1b/protein IX poly A signal) in a pBR322 background. Recombinant adenovirus was produced by standard procedures. The plasmid pASN286-56 was linearized with Ngo MI and co-transfected into 293 cells with the large fragment of Cla I digested rAd34 which has deletions in both the E3 and E4 regions of adenovirus type 5. Ad34 was a serotype 5 derivative with a 1.9 KB deletion in early region 3 resulting from deletion of the Xba I restriction fragment extending from Ad5 coordinates 28593 to 30470 and a 1.4 KB deletion of early region 4 resulting from a Taq 1 fragment of E4 (coordinates 33055-35573) being replaced with a cDNA containing E4 ORF 6 and 6/7.

Recombinant adenovirus produced by homologous recombination was isolated and identified by restriction digest analysis and further purified by limiting dilution. Additional control recombinant adenoviruses are described elsewhere and include the control virus ACN (CMV promoter, Wills, et al. "Gene Therapy For Hepatocellular Carcinoma: Chemosensitivity Conferred By Adenovirus-Mediated Transfer of The HSV-1 Thymidine Kinase Gene." *Cancer Gene Therapy* 2:191–197 (1995)), and ACN56 (RB expressed under control of a CMV promoter).

ACN56 was prepared as follows. A plasmid containing p56 cDNA was constructed by replacing the p53 cDNA from the plasmid ACNP53 (Wills et al. Human Gene Therapy 5:1079–1088 (1994)) with a 1.7 KB Xba I- BamHI fragment isolated from plasmid pET 9a-Rb56 (Antelman et al. *Oncogene* 10:697–704 (1995)) which contains p56 cDNA. The resulting plasmid contained amino acids 381–928 of p56, the Ad5 inverted terminal repeat, viral packaging signals and E1a enhancer, followed by the human cytomegalovirus immediate early promoter (CMV) and Ad 2 tripartite leader cDNA to drive p56 expression. The p56 CDNA was followed by Ad 2 sequence 4021–10462 in a pBR322 background. This plasmid was linearized with EcoRI and cotransfected with the large fragment of bsp 106 digested DL327 (E3 deleted; Thimmappayn et al. *Cell* 31:543–551 (1982)) or h5ile4 (E4 deleted; Hemstrom et al. *J. Virol.* 62:3258–3264 (1988)). Recombinant viruses were further purified by limiting dilution.

B. Cellular Proliferation

In this experiment, cell lines were infected in culture with recombinant adenovirus RB constructs to ascertain the relative expression of the RB polypeptide and the effect on cell proliferation.

For H358 (ATCC # Crl 5807) and MDA-MB468 (ATCC # HTB 132, breast adenocarcinoma) cells, 5,000 cell/well were plated in normal growth media in a 96 well microtiter plate (Costar) and allowed to incubate overnight at 37° C., 7% $CO_2$. Viruses were serially diluted in growth media and used to infect cells at the indicated doses for 48 hours. At this point, $^3$H-thymidine was added (Amersham, 0.5 µCi/well) and the cells were incubated at 37° C. for another 3 hours prior to harvest. Both A7r5 (ATCC CRL1444, rat smooth muscle) and A10 (ATCC CRL 1476, rat smooth muscle) cells were seeded at 3,000 cells/well in either DME+0.5% FCS or DME+20% FCS respectively. Virus was serially diluted in the seeding media and used to infect the cells at the doses indicated in the Figures. The infection and labelling procedure were the same for A10 cells as with the H358 and MDA-MB468 cells except that 2 µCi/well of label was used. The A7r5 cells were not infected with virus until 48 hours after seeding. Forty eight hours after infection, the serum concentration was raised to 10% FCS and 2 µCi/well of $^3$H-thymidine was added and incubation continued for an additional 3 hours prior to harvest. All cells were harvested by aspirating media from the wells, trypsinization of the cells, and harvesting using a 96 well GF/C filter with a Packard Top count cell harvester. Results are plotted as the mean percentage (+/− SD) of media treated control proliferation versus dose of virus in FIGS. 13 and 14.

Thus, FIG. 13 depicts a comparison of the effects of adenovirus p56 constructs on muscle cells A10 and A7R5 cells. The CMV-driven p56 (ACN 56) virus inhibited A10 growth to approximately the same extent as the actin promoter-driven E2F-fusion constructs (ASN586-56 #25, 26). In FIG. 14, the effects of adenovirus constructs on inhibition of a breast cancer cell line, MDA Mβ468 and a non-small cell lung carcinoma cell line, H358, are depicted. In these experiments, actin promoter-driven E2F-p56 was ineffective, while the CMV promoter-driven p56 was effective in inhibiting growth of non-smooth muscle cells.

To determine whether the non-smooth muscle cells were more infectable with adenovirus than the smooth muscle cell lines used, the four cells lines, H358, MB468, A7R5, and A10 were infected at an MOI of 5 with an adenovirus expressing β-galactosidase (ACβGL; Wills, et al. *Human Gene Therapy* 5:1079–1088 (1994)) and degree of β-gal staining was examined. As shown in FIG. 15 (top), the non-smooth muscle cell lines were significantly more infectable than the smooth muscle cell lines. In a further test, cells were infected at higher multiplicities of infection (50, 100, 250, 500) with ACN56 and the amount of p56 present in the infected cells detected by autoradiography. As can be seen in FIG. 15 (bottom), the non-muscle cell lines had significantly more p56 present, since as a result of their greater infectivity, infected cells have a greater viral load and thus more copies of the p56 template driven by the non-tissue specific CMV promoter.

In a further experiment, the specificity of the actin smooth muscle promoter for smooth muscle tissue was ascertained. In this experiment, β-gal expression levels in cells infected with β-gal constructs driven with different promoters were measured. As can be seen in FIG. 19, despite the lower infectivity of the smooth muscle cells, expression was only evident in these cells using the smooth muscle alpha actin promoter.

FIG. 21 depicts a comparison of the effects of a CMV driven p56 recombinant adenovirus (ACN56E4) vs a human smooth muscle alpha-actin promoter driven E2F-p56 fusion construct (ASN286-56) vs control adenoviral construct containing either the CMV or smooth muscle alpha-actin promoters without a downstream transgene (ACNE3 or ASBE3-2 isolates shown, respectively). Assays were 3H-thymidine uptake either in a smooth muscle cell line (A7R5) or a non-muscle cell line (MDA-MB468, breast carcinoma). Results demonstrated muscle tissue specificity using the smooth muscle alpha-actin promoter and specific inhibition of both the p56 and E2F-p56 transgenes relative to their respective controls.

C. Inhibition of Restenosis

The model of balloon injury was based on that described by Clowes, et al. (Clowes, *Lab. Invest.* 49:327–333 (1983)). Male Sprague-Dawley rats weighing 400–500 g were anesthetized with an intraperitoneal injection of sodium ipentobarbital (45 mg/kg. Abbot Laboratories, North Chicago, Ill.). The bifurcation of the left common carotid artery was exposed through a midline incision and the left common, internal, and external carotid arteries were temporarily ligated. A 2F embolectomy catheter (Baxter Edwards Healthcare Corp., Irvine, Calif.) was introduced into the external carotid and advanced to the distal ligation of the common carotid. The balloon was inflated with saline and drawn towards the arteriotomy site 3 times to produce a distending, deendothelializing injury. The catheter was then withdrawn. Adenovirus ($1 \times 10^9$ pfu of Ad-RB (ACNRb) or Ad-p56 (ACN56) in a volume of 10 μl diluted to 100 μl with 15% (wt/vol) Poloxamer 407 (BASF, Parsippany, N.J.) or Ad-β-Gal ($1 \times 10^9$ pfu, diluted as above) was injected via a canula, inserted just proximal to the carotid bifurcation into a temporarily isolated segment of the artery. The adenovirus solution was incubated for 20 minutes after which the viral infusion was withdrawn and the cannula removed. The proximal external carotid artery was then ligated and blood flow was restored to the common carotid artery by release of the ligatures. The experimental protocol was approved by the Institutional Animal Care and Use Committee and complied with the "Guide for the Care and Use of Laboratory Animals." (NIH Publication No. 86-23, revised 1985).

Rats were sacrificed at 14 days following treatment with an intraperitoneal injection of pentobarbital (100 mg/kg.). The initially balloon injured segment of the left common carotid artery, from the proximal edge of the omohyoid muscle to the carotid bifurcation, was perfused with saline and dissected free of the surrounding tissue. The tissue was fixed in 100% methanol until imbedded in paraffin. Several 4-μm sections were cut from each tissue specimen. One section from each specimen was stained with hematoxylin and eosin and another with Richardson's combination elastic-trichrome stain conventional light microscopic analysis.

Histological images of cross sections of hematoxylin and eosin or elastic-trichrome stained arterial sections were projected onto a digitizing board (Summagraphics) and the intimal, medial and luminal areas were measured by quantitative morphometric analysis using a computerized sketching program (MACMEASURE, version 1.9, National Institute of Mental Health).

Results were expressed as the mean±S.E.M. Differences between groups were analyzed using an unpaired two-tailed Student's t test. Statistical significance was assumed when the probability of a null effect was <0.05.

Results are shown in FIGS. 17 and 18. In FIG. 17, the relative inhibition of neointima formation is depicted graphically, demonstrating the ability of p56 and RB to inhibit neointima formation. FIG. 18 provides photographic evidence of the dramatic reduction of neointima in the presence of p56.

Adenovirus-treated carotid arteries were harvested from rats at 2 days following balloon injury and infections. Tissue was fixed in phosphate-buffered formalin until embedded in paraffin. Tissue was cut into 4 μm cross-sections and dewaxed through xylene and graded alcohols. Endogenous peroxidase was quenched with 1% hydrogen peroxide for 30 minutes. Antigen retrieval was performed in 10 mM sodium citrate buffer, pH 6.0 at 95° C. for 10 minutes. A monoclonal anti-RB antibody (AB-5, Oncogene Sciences, Uniondale, N.Y.) was applied 10 μg/ml in PBS in a humid chamber at 4° C. for 24 hours. Secondary antibody was applied from the Unitect Mouse Immunohistochemistry Kit (Oncogene Sciences, Uniondale, N.Y.) according to the manufacturer's instructions. The antibody complexes were visualized using 3,3'-diaminobenzidene (DAB, Vector Laboratories, Burlingame, Calif.). Slides were thin counterstained with hematoxylin and mounted. The results are depicted in FIG. 20.

All references cited herein are hereby incorporated by reference in their entirety for all purposes.

What is claimed is:

1. A fusion polypeptide that comprises a DNA binding domain of an E2F transcription factor and the functional growth suppression domain of a retinoblastoma (RB) polypeptide wherein the fusion polypeptide lacks a functional cyclin A-kinase binding domain of the transcription factor.

2. The polypeptide of claim 1, wherein the cyclin A binding domain of the E2F is deleted or nonfunctional.

3. The polypeptide of claim 2, wherein the E2F comprises about amino acid residues 95 to about 286 (SEQ ID NO:1).

4. The polypeptide of claim 1, wherein the retinoblastoma polypeptide is RB56.

5. The polypeptide of claim 1, wherein the retinoblastoma polypeptide is wild type RB.

6. The polypeptide of claim 1, wherein the retinoblastoma polypeptide comprises from about amino acid residue 379 to about amino acid residue 928 of pRB (SEQ ID NO:4).

7. The polypeptide of claim 1, wherein the retinoblastoma polypeptide comprises at least one substitution of amino acid residues selected from the group consisting of 2, 608, 612, 788, 807, and 811 of pRB (SEQ ID NO:4).

8. The polypeptide of claim 1, wherein the E2F comprises about amino acid residues 95 to about 194 (SEQ ID NO:1).

9. The polypeptide of claim 1, wherein the fusion polypeptide comprises EF2 amino acid residues from about 95 to about 194 operatively linked to RB amino acid residues from about 379 to about 928 (SEQ ID NO:4).

10. The polypeptide of claim 1, wherein the polypeptide further comprises a nuclear localization signal.

11. The polypeptide of claim 10, wherein the nuclear localization signal is that of SV40 T antigen.

* * * * *

```
                         SEQUENCE LISTING (1) GENERAL INFORMATION:

(iii) NUMBER OF SEQUENCES: 46

(2) INFORMATION FOR SEQ ID NO: 1:

(i) SEQUENCE CHARACTERISTICS:
         (A) LENGTH: 437 amino acids
         (B) TYPE: amino acid
         (C) STRANDEDNESS: not relevant
         (D) TOPOLOGY: not relevant (ii) MOLECULE TYPE: peptide (xi) SEQUENCE DESCRIPTION: SEQ ID NO: 1:
```

-continued

```
Met Ala Leu Ala Gly Ala Pro Ala Gly Gly Pro Cys Ala Pro Ala Leu
1               5                   10                  15

Glu Ala Leu Leu Gly Ala Gly Ala Leu Arg Leu Leu Asp Ser Ser Gln
            20                  25                  30

Ile Val Ile Ile Ser Ala Ala Gln Asp Ala Ser Ala Pro Pro Ala Pro
            35                  40                  45

Thr Gly Pro Ala Ala Pro Ala Ala Gly Pro Cys Asp Pro Asp Leu Leu
    50                  55                  60

Leu Phe Ala Thr Pro Gln Ala Pro Arg Pro Thr Pro Ser Ala Pro Arg
65                  70                  75                  80

Pro Ala Leu Gly Arg Pro Pro Val Lys Arg Arg Leu Asp Leu Glu Thr
                85                  90                  95

Asp His Gln Tyr Leu Ala Glu Ser Ser Gly Pro Ala Arg Gly Arg Gly
                100                 105                 110

Arg His Pro Gly Lys Gly Val Lys Ser Pro Gly Glu Lys Ser Arg Tyr
                115                 120                 125

Glu Thr Ser Leu Asn Leu Thr Thr Lys Arg Phe Leu Glu Leu Leu Ser
    130                 135                 140

His Ser Ala Asp Gly Val Val Asp Leu Asn Trp Ala Ala Glu Val Leu
145                 150                 155                 160

Lys Val Gln Lys Arg Arg Ile Tyr Asp Ile Thr Asn Val Leu Glu Gly
                165                 170                 175

Ile Gln Leu Ile Ala Lys Lys Ser Lys Asn His Ile Gln Trp Leu Gly
                180                 185                 190

Ser His Thr Thr Val Gly Val Gly Gly Arg Leu Glu Gly Leu Thr Gln
    195                 200                 205

Asp Leu Arg Gln Leu Gln Glu Ser Glu Gln Gln Leu Asp His Leu Met
    210                 215                 220

Asn Ile Cys Thr Thr Gln Leu Arg Leu Leu Ser Glu Asp Thr Asp Ser
225                 230                 235                 240

Gln Arg Leu Ala Tyr Val Thr Cys Gln Asp Leu Arg Ser Ile Ala Asp
                245                 250                 255

Pro Ala Glu Gln Met Val Met Val Ile Lys Ala Pro Pro Glu Thr Gln
                260                 265                 270

Leu Gln Ala Val Asp Ser Ser Glu Asn Phe Gln Ile Ser Leu Lys Ser
            275                 280                 285

Lys Gln Gly Pro Ile Asp Val Phe Leu Cys Pro Glu Glu Thr Val Gly
    290                 295                 300

Gly Ile Ser Pro Gly Lys Thr Pro Ser Gln Glu Val Thr Ser Glu Glu
305                 310                 315                 320

Glu Asn Arg Ala Thr Asp Ser Ala Thr Ile Val Ser Pro Pro Pro Ser
                325                 330                 335

Ser Pro Pro Ser Ser Leu Thr Thr Asp Pro Ser Gln Ser Leu Leu Ser
                340                 345                 350

Leu Glu Gln Glu Pro Leu Leu Ser Arg Met Gly Ser Leu Arg Ala Pro
            355                 360                 365

Val Asp Glu Asp Arg Leu Ser Pro Leu Val Ala Ala Asp Ser Leu Leu
    370                 375                 380

Glu His Val Arg Glu Asp Phe Ser Gly Leu Leu Pro Glu Glu Phe Ile
385                 390                 395                 400

Ser Leu Ser Pro Pro His Glu Ala Leu Asp Tyr His Phe Gly Leu Glu
                405                 410                 415

Glu Gly Glu Gly Ile Arg Asp Leu Phe Asp Cys Asp Phe Gly Asp Leu
```

```
              420            425            430
Thr Pro Leu Asp Phe
        435

(2) INFORMATION FOR SEQ ID NO: 2:

(i) SEQUENCE CHARACTERISTICS:
        (A) LENGTH: 2517 base pairs
        (B) TYPE: nucleic acid
        (C) STRANDEDNESS: single
        (D) TOPOLOGY: linear (xi) SEQUENCE DESCRIPTION: SEQ ID NO: 2:

GGAATTCCGT GGCCGGGACT TTGCAGGCAG CGGCGGCCGG GGGCGGAGCG GGATCGAGCC      60

CTCGCCGAGG CCTGCCGCCA TGGGCCCGCG CCGCCGCCGC CGCCTGTCAC CCGGGCCGCG     120

CGGGCCGTGA GCGTCATGGC CTTGGCCGGG CCCCTGCGG GCGGCCCATG CGCGCCGGCG      180

CTGGAGGCCC TGCTCGGGGC CGGCGCGCTG CGGCTGCTCG ACTCCTCGCA GATCGTCATC     240

ATCTCCGCCG CGCAGGACGC CAGCGCCCCG CCGGCTCCCA CCGGCCCCGC GGCGCCCGCC     300

GCCGGCCCCT GCGACCCTGA CCTGCTGCTC TTCGCCACAC CGCAGGCGCC CCGGCCCACA     360

CCCAGTGCGC CGCGGCCCGC GCTCGGCCGC CCGCCGGTGA AGCGGAGGCT GGACCTGGAA     420

ACTGACCATC AGTACCTGGC CGAGAGCAGT GGGCCAGCTC GGGGCAGAGG CCGCCATCCA     480

GGAAAAGGTG TGAAATCCCC GGGGGAGAAG TCACGCTATG AGACCTCACT GAATCTGACC     540

ACCAAGCGCT TCCTGGAGCT GCTGAGCCAC TCGGCTGACG GTGTCGTCGA CCTGAACTGG     600

GCTGCCGAGG TGCTGAAGGT GCAGAAGCGG CGCATCTATG ACATCACCAA CGTCCTTGAG     660

GGCATCCAGC TCATTGCCAA GAAGTCCAAG AACCACATCC AGTGGCTGGG CAGCCACACC     720

ACAGTGGGCG TCGGCGGACG GCTTGAGGGG TTGACCCAGG ACCTCCGACA GCTGCAGGAG     780

AGCGAGCAGC AGCTGGACCA CCTGATGAAT ATCTGTACTA CGCAGCTGCG CCTGCTCTCC     840

GAGGACACTG ACAGCCAGCG CCTGGCCTAC GTGACGTGTC AGGACCTTCG TAGCATTGCA     900

GACCCTGCAG AGCAGATGGT TATGGTGATC AAAGCCCCTC CTGAGACCCA GCTCCAAGCC     960

GTGGACTCTT CGGAGAACTT TCAGATCTCC CTTAAGAGCA AACAAGGCCC GATCGATGTT    1020

TTCCTGTGCC CTGAGGAGAC CGTAGGTGGG ATCAGCCCTG GAAGACCCC ATCCCAGGAG    1080

GTCACTTCTG AGGAGGAGAA CAGGGCCACT GACTCTGCCA CCATAGTGTC ACCACCACCA    1140

TCATCTCCCC CCTCATCCCT CACCACAGAT CCCAGCCAGT CTCTACTCAG CCTGGAGCAA    1200

GAACCGCTGT TGTCCCGGAT GGGCAGCCTG CGGGCTCCCG TGGACGAGGA CCGCCTGTCC    1260

CCGCTGGTGG CGGCCGACTC GCTCCTGGAG CATGTGCGGG AGGACTTCTC CGGCCTCCTC    1320

CCTGAGGAGT TCATCAGCCT TTCCCCACCC CACGAGGCCC TCGACTACCA CTTCGGCCTC    1380

GAGGAGGGCG AGGGCATCAG AGACCTCTTC GACTGTGACT TGGGGACCT CACCCCCCTG    1440

GATTTCTGAC AGGGCTTGGA GGGACCAGGG TTTCCAGAGT AGCTCACCTT GTCTCTGCAG    1500

CCCTGGAGCC CCCTGTCCCT GGCCGTCCTC CCAGCCTGTT TGGAAACATT TAATTTATAC    1560

CCCTCTCCTC TGTCTCCAGA AGCTTCTAGC TCTGGGTCT GGCTACCGCT AGGAGGCTGA    1620

GCAAGCCAGG AAGGGAAGGA GTCTGTGTGG TGTGTATGTG CATGCAGCCT ACACCCACAC    1680

GTGTGTACCG GGGGTGAATG TGTGTGAGCA TGTGTGTGTG CATGTACCGG GGAATGAAGG    1740

TGAACATACA CCTCTGTGTG TGCACTGCAG ACACGCCCCA GTGTGTCCAC ATGTGTGTGC    1800

ATGAGTCCAT CTCTGCGCGT GGGGGGGCTC TAACTGCACT TTCGGCCCTT TTGCTCGTGG    1860

GGTCCCACAA GGCCCAGGGC AGTGCCTGCT CCCAGAATCT GGTGCTCTGA CCAGGCCAGG    1920
```

-continued

```
TGGGGAGGCT TTGGCTGGCT GGGCGTGTAG GACGGTGAGA GCACTTCTGT CTTAAAGGTT    1980

TTTTCTGATT GAAGCTTTAA TGGAGCGTTA TTTATTTATC GAGGCCTCTT TGGTGAGCCT    2040

GGGGAATCAG CAAAAGGGGA GGAGGGGTGT GGGGTTGATA CCCCAACTCC CTCTACCCTT    2100

GAGCAAGGGC AGGGGTCCCT GAGCTGTTCT TCTGCCCCAT ACTGAAGGAA CTGAGGCCTG    2160

GGTGATTTAT TTATTGGGAA AGTGAGGGAG GGAGACAGAC TGACTGACAG CCATGGGTGG    2220

TCAGATGGTG GGGTGGGCCC TCTCCAGGGG GCCAGTTCAG GGCCCAGCTG CCCCCCAGGA    2280

TGGATATGAG ATGGGAGAGG TGAGTGGGGG ACCTTCACTG ATGTGGGCAG GAGGGGTGGT    2340

GAAGGCCTCC CCCAGCCCAG ACCCTGTGGT CCCTCCTGCA GTGTCTGAAG CGCCTGCCTC    2400

CCCACTGCTC TGCCCCACCC TCCAATCTGC ACTTTGATTT GCTTCCTAAC AGCTCTGTTC    2460

CCTCCTGCTT TGGTTTTAAT AAATATTTTG ATGACGTTAA AAAAAGGAAT TCGATAT      2517
```

(2) INFORMATION FOR SEQ ID NO: 3:

(i) SEQUENCE CHARACTERISTICS:
        (A) LENGTH: 2994 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
TTCCGGTTTT TCTCAGGGGA CGTTGAAATT ATTTTTGTAA CGGGAGTCGG GAGAGGACGG      60

GGCGTGCCCC GCGTGCGCGC GCGTCGTCCT CCCCGGCGCT CCTCCACAGC TCGCTGGCTC     120

CCGCCGCGGA AAGGCGTCAT GCCGCCCAAA ACCCCCCGAA AAACGGCCGC CACCGCCGCC     180

GCTGCCGCCG CGGAACCCCC GGCACCGCCG CCGCCGCCCC CTCCTGAGGA GGACCCAGAG     240

CAGGACAGCG GCCCGGAGGA CCTGCCTCTC GTCAGGCTTG AGTTTGAAGA AACAGAAGAA     300

CCTGATTTTA CTGCATTATG TCAGAAATTA AAGATACCAG ATCATGTCAG AGAGAGAGCT     360

TGGTTAACTT GGGAGAAAGT TTCATCTGTG GATGGAGTAT TGGGAGGTTA TATTCAAAAG     420

AAAAAGGAAC TGTGGGGAAT CTGTATCTTT ATTGCAGCAG TTGACCTAGA TGAGATGTCG     480

TTCACTTTTA CTGAGCTACA GAAAAACATA GAAATCAGTG TCCATAAATT CTTTAACTTA     540

CTAAAAGAAA TTGATACCAG TACCAAAGTT GATAATGCTA TGTCAAGACT GTTGAAGAAG     600

TATGATGTAT TGTTTGCACT CTTCAGCAAA TTGGAAAGGA CATGTGAACT TATATATTTG     660

ACACAACCCA GCAGTTCGAT ATCTACTGAA ATAAATTCTG CATTGGTGCT AAAAGTTTCT     720

TGGATCACAT TTTTATTAGC TAAAGGGGAA GTATTACAAA TGGAAGATGA TCTGGTGATT     780

TCATTTCAGT TAATGCTATG TGTCCTTGAC TATTTTATTA AACTCTCACC TCCCATGTTG     840

CTCAAAGAAC CATATAAAAC AGCTGTTATA CCCATTAATG TTCACCTCG AACACCCAGG      900

CGAGGTCAGA ACAGGAGTGC ACGGATAGCA AAACAACTAG AAAATGATAC AAGAATTATT     960

GAAGTTCTCT GTAAAGAACA TGAATGTAAT ATAGATGAGG TGAAAATGT TTATTTCAAA     1020

AATTTTATAC CTTTTATGAA TTCTCTTGGA CTTGTAACAT CTAATGGACT TCCAGAGGTT    1080

GAAAATCTTT CTAAACGATA CGAAGAAATT TATCTTAAAA ATAAAGATCT AGATGCAAGA    1140

TTATTTTTGG ATCATGATAA AACTCTTCAG ACTGATTCTA TAGACAGTTT TGAAACACAG    1200

AGAACACCAC GAAAAAGTAA CCTTGATGAA GAGGTGAATG TAATTCCTCC ACACACTCCA    1260

GTTAGGACTG TTATGAACAC TATCCAACAA TTAATGATGA TTTTAAATTC AGCAAGTGAT    1320

CAACCTTCAG AAAATCTGAT TTCCTATTTT AACAACTGCA CAGTGAATCC AAAAGAAAGT    1380
```

```
ATACTGAAAA GAGTGAAGGA TATAGGATAC ATCTTTAAAG AGAAATTTGC TAAAGCTGTG    1440

GGACAGGGTT GTGTCGAAAT TGGATCACAG CGATACAAAC TTGGAGTTCG CTTGTATTAC    1500

CGAGTAATGG AATCCATGCT TAAATCAGAA GAAGAACGAT TATCCATTCA AAATTTTAGC    1560

AAACTTCTGA ATGACAACAT TTTTCATATG TCTTTATTGG CGTGCGCTCT TGAGGTTGTA    1620

ATGGCCACAT ATAGCAGAAG TACATCTCAG AATCTTGATT CTGGAACAGA TTTGTCTTTC    1680

CCATGGATTC TGAATGTGCT TAATTTAAAA GCCTTTGATT TTTACAAAGT GATCGAAAGT    1740

TTTATCAAAG CAGAAGGCAA CTTGACAAGA GAAATGATAA ACATTTAGA ACGATGTGAA     1800

CATCGAATCA TGGAATCCCT TGCATGGCTC TCAGATTCAC CTTTATTTGA TCTTATTAAA    1860

CAATCAAAGG ACCGAGAAGG ACCAACTGAT CACCTTGAAT CTGCTTGTCC TCTTAATCTT    1920

CCTCTCCAGA ATAATCACAC TGCAGCAGAT ATGTATCTTT CTCCTGTAAG ATCTCCAAAG    1980

AAAAAAGGTT CAACTACGCG TGTAAATTCT ACTGCAAATG CAGAGACACA AGCAACCTCA    2040

GCCTTCCAGA CCCAGAAGCC ATTGAAATCT ACCTCTCTTT CACTGTTTTA TAAAAAGTG     2100

TATCGGCTAG CCTATCTCCG GCTAAATACA CTTTGTGAAC GCCTTCTGTC TGAGCACCCA    2160

GAATTAGAAC ATATCATCTG GACCCTTTTC CAGCACACCC TGCAGAATGA GTATGAACTC    2220

ATGAGAGACA GGCATTTGGA CCAAATTATG ATGTGTTCCA TGTATGGCAT ATGCAAAGTG    2280

AAGAATATAG ACCTTAAATT CAAAATCATT GTAACAGCAT ACAAGGATCT TCCTCATGCT    2340

GTTCAGGAGA CATTCAAACG TGTTTTGATC AAAGAAGAGG AGTATGATTC TATTATAGTA    2400

TTCTATAACT CGGTCTTCAT GCAGAGACTG AAAACAAATA TTTTGCAGTA TGCTTCCACC    2460

AGGCCCCCTA CCTTGTCACC AATACCTCAC ATTCCTCGAA GCCCTTACAA GTTTCCTAGT    2520

TCACCCTTAC GGATTCCTGG AGGGAACATC TATATTTCAC CCCTGAAGAG TCCATATAAA    2580

ATTTCAGAAG GTCTGCCAAC ACCAACAAAA ATGACTCCAA GATCAAGAAT CTTAGTATCA    2640

ATTGGTGAAT CATTCGGGAC TTCTGAGAAG TTCCAGAAAA TAAATCAGAT GGTATGTAAC    2700

AGCGACCGTG TGCTCAAAAG AAGTGCTGAA GGAAGCAACC CTCCTAAACC ACTGAAAAAA    2760

CTACGCTTTG ATATTGAAGG ATCAGATGAA GCAGATGGAA GTAAACATCT CCCAGGAGAG    2820

TCCAAATTTC AGCAGAAACT GGCAGAAATG ACTTCTACTC GAACACGAAT GCAAAAGCAG    2880

AAAATGAATG ATAGCATGGA TACCTCAAAC AAGGAAGAGA AATGAGGATC TCAGGACCTT    2940

GGTGGACACT GTGTACACCT CTGGATTCAT TGTCTCTCAC AGATGTGACT GTAT          2994
```

(2) INFORMATION FOR SEQ ID NO: 4:

(i) SEQUENCE CHARACTERISTICS:
        (A) LENGTH: 928 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 4:

```
Met Pro Pro Lys Thr Pro Arg Lys Thr Ala Ala Thr Ala Ala Ala Ala
1               5                   10                  15

Ala Ala Glu Pro Pro Ala Pro Pro Pro Pro Pro Pro Glu Glu Asp
            20                  25                  30

Pro Glu Gln Asp Ser Gly Pro Glu Asp Leu Pro Leu Val Arg Leu Glu
        35                  40                  45

Phe Glu Glu Thr Glu Glu Pro Asp Phe Thr Ala Leu Cys Gln Lys Leu
    50                  55                  60
```

```
Lys Ile Pro Asp His Val Arg Glu Arg Ala Trp Leu Thr Trp Glu Lys
 65                  70                  75                  80

Val Ser Ser Val Asp Gly Val Leu Gly Gly Tyr Ile Gln Lys Lys Lys
                 85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
            115                 120                 125

His Lys Phe Phe Asn Leu Leu Lys Glu Ile Asp Thr Ser Thr Lys Val
        130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
            195                 200                 205

Glu Asp Asp Leu Val Ile Ser Phe Gln Leu Met Leu Cys Val Leu Asp
210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
        275                 280                 285

Lys Asn Val Tyr Phe Lys Asn Phe Ile Pro Phe Met Asn Ser Leu Gly
290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
            340                 345                 350

Thr Gln Arg Thr Pro Arg Lys Ser Asn Leu Asp Glu Glu Val Asn Val
            355                 360                 365

Ile Pro Pro His Thr Pro Val Arg Thr Val Met Asn Thr Ile Gln Gln
370                 375                 380

Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
                405                 410                 415

Lys Arg Val Lys Asp Ile Gly Tyr Ile Phe Lys Glu Lys Phe Ala Lys
            420                 425                 430

Ala Val Gly Gln Gly Cys Val Glu Ile Gly Ser Gln Arg Tyr Lys Leu
            435                 440                 445

Gly Val Arg Leu Tyr Tyr Arg Val Met Glu Ser Met Leu Lys Ser Glu
            450                 455                 460

Glu Glu Arg Leu Ser Ile Gln Asn Phe Ser Lys Leu Leu Asn Asp Asn
465                 470                 475                 480
```

```
Ile Phe His Met Ser Leu Leu Ala Cys Ala Leu Glu Val Val Met Ala
                485                 490                 495
Thr Tyr Ser Arg Ser Thr Ser Gln Asn Leu Asp Ser Gly Thr Asp Leu
                500                 505                 510
Ser Phe Pro Trp Ile Leu Asn Val Leu Asn Leu Lys Ala Phe Asp Phe
                515                 520                 525
Tyr Lys Val Ile Glu Ser Phe Ile Lys Ala Glu Gly Asn Leu Thr Arg
    530                 535                 540
Glu Met Ile Lys His Leu Glu Arg Cys Glu His Arg Ile Met Glu Ser
545                 550                 555                 560
Leu Ala Trp Leu Ser Asp Ser Pro Leu Phe Asp Leu Ile Lys Gln Ser
                565                 570                 575
Lys Asp Arg Glu Gly Pro Thr Asp His Leu Glu Ser Ala Cys Pro Leu
                580                 585                 590
Asn Leu Pro Leu Gln Asn Asn His Thr Ala Ala Asp Met Tyr Leu Ser
                595                 600                 605
Pro Val Arg Ser Pro Lys Lys Lys Gly Ser Thr Thr Arg Val Asn Ser
    610                 615                 620
Thr Ala Asn Ala Glu Thr Gln Ala Thr Ser Ala Phe Gln Thr Gln Lys
625                 630                 635                 640
Pro Leu Lys Ser Thr Ser Leu Ser Leu Phe Tyr Lys Lys Val Tyr Arg
                645                 650                 655
Leu Ala Tyr Leu Arg Leu Asn Thr Leu Cys Glu Arg Leu Leu Ser Glu
                660                 665                 670
His Pro Glu Leu Glu His Ile Ile Trp Thr Leu Phe Gln His Thr Leu
                675                 680                 685
Gln Asn Glu Tyr Glu Leu Met Arg Asp Arg His Leu Asp Gln Ile Met
    690                 695                 700
Met Cys Ser Met Tyr Gly Ile Cys Lys Val Lys Asn Ile Asp Leu Lys
705                 710                 715                 720
Phe Lys Ile Ile Val Thr Ala Tyr Lys Asp Leu Pro His Ala Val Gln
                725                 730                 735
Glu Thr Phe Lys Arg Val Leu Ile Lys Glu Glu Glu Tyr Asp Ser Ile
                740                 745                 750
Ile Val Phe Tyr Asn Ser Val Phe Met Gln Arg Leu Lys Thr Asn Ile
                755                 760                 765
Leu Gln Tyr Ala Ser Thr Arg Pro Pro Thr Leu Ser Pro Ile Pro His
    770                 775                 780
Ile Pro Arg Ser Pro Tyr Lys Phe Pro Ser Ser Pro Leu Arg Ile Pro
785                 790                 795                 800
Gly Gly Asn Ile Tyr Ile Ser Pro Leu Lys Ser Pro Tyr Lys Ile Ser
                805                 810                 815
Glu Gly Leu Pro Thr Pro Thr Lys Met Thr Pro Arg Ser Arg Ile Leu
                820                 825                 830
Val Ser Ile Gly Glu Ser Phe Gly Thr Ser Glu Lys Phe Gln Lys Ile
                835                 840                 845
Asn Gln Met Val Cys Asn Ser Asp Arg Val Leu Lys Arg Ser Ala Glu
    850                 855                 860
Gly Ser Asn Pro Pro Lys Pro Leu Lys Lys Leu Arg Phe Asp Ile Glu
865                 870                 875                 880
Gly Ser Asp Glu Ala Asp Gly Ser Lys His Leu Pro Gly Glu Ser Lys
                885                 890                 895
Phe Gln Gln Lys Leu Ala Glu Met Thr Ser Thr Arg Thr Arg Met Gln
```

```
                900              905              910
Lys Gln Lys Met Asn Asp Ser Met Asp Thr Ser Asn Lys Glu Glu Lys
            915              920              925
```

(2) INFORMATION FOR SEQ ID NO: 5:

(i) SEQUENCE CHARACTERISTICS:
        (A) LENGTH: 3853 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 209..250

(ix) FEATURE:
        (A) NAME/KEY: CDS
        (B) LOCATION: 254..289

(ix) FEATURE:
        (A) NAME/KEY: CDS
        (B) LOCATION: 293..505

(ix) FEATURE:
        (A) NAME/KEY: CDS
        (B) LOCATION: 509..514

(ix) FEATURE:
        (A) NAME/KEY: CDS
        (B) LOCATION: 518..520

(ix) FEATURE:
        (A) NAME/KEY: CDS
        (B) LOCATION: 524..658

(ix) FEATURE:
        (A) NAME/KEY: CDS
        (B) LOCATION: 662..691

(ix) FEATURE:
        (A) NAME/KEY: CDS
        (B) LOCATION: 695..748

(ix) FEATURE:
        (A) NAME/KEY: CDS
        (B) LOCATION: 752..781

(ix) FEATURE:
        (A) NAME/KEY: CDS
        (B) LOCATION: 785..829

(ix) FEATURE:
        (A) NAME/KEY: CDS
        (B) LOCATION: 1132..1134

(ix) FEATURE:
        (A) NAME/KEY: CDS
        (B) LOCATION: 1138..1149

(ix) FEATURE:
        (A) NAME/KEY: CDS
        (B) LOCATION: 833..862

(xi) SEQUENCE DESCRIPTION: SEQ ID NO: 5:

```
GACGGATCGG GAGATCTCCC GATCCCCTAT GGTCGACTCT CAGTACAATC TGCTCTGATG      60

CCGCATAGTT AAGCCAGTAT CTGCTCCCTG CTTGTGTGTT GGAGGTCGCT GAGTAGTGCG     120

CGAGCAAAAT TTAAGCTACA ACAAGGCAAG GCTTGACCGA CAATTGCATG AAGAATCTGC     180

TTAGGGTTAG GCGTTTTGCG CTGCTTCG CGA TGT ACG GGC CAG ATA TAC GCG        232
                                Arg Cys Thr Gly Gln Ile Tyr Ala
                                 1               5
```

```
TTG ACA TTG ATT ATT GAC TAG TTA TTA ATA GTA ATC AAT TAC GGG GTC        280
Leu Thr Leu Ile Ile Asp     Leu Leu Ile Val Ile Asn Tyr Gly Val
     10                       1               5

ATT AGT TCA TAG CCC ATA TAT GGA GTT CCG CGT TAC ATA ACT TAC GGT        328
Ile Ser Ser     Pro Ile Tyr Gly Val Pro Arg Tyr Ile Thr Tyr Gly
 10          1               5                      10

AAA TGG CCC GCC TGG CTG ACC GCC CAA CGA CCC CCG CCC ATT GAC GTC        376
Lys Trp Pro Ala Trp Leu Thr Ala Gln Arg Pro Pro Pro Ile Asp Val
             15                  20                  25

AAT AAT GAC GTA TGT TCC CAT AGT AAC GCC AAT AGG GAC TTT CCA TTG        424
Asn Asn Asp Val Cys Ser His Ser Asn Ala Asn Arg Asp Phe Pro Leu
     30                  35                  40

ACG TCA ATG GGT GGA CTA TTT ACG GTA AAC TGC CCA CTT GGC AGT ACA        472
Thr Ser Met Gly Gly Leu Phe Thr Val Asn Cys Pro Leu Gly Ser Thr
 45                  50                  55                  60

TCA AGT GTA TCA TAT GCC AAG TAC GCC CCC TAT TGA CGT CAA                514
Ser Ser Val Ser Tyr Ala Lys Tyr Ala Pro Tyr     Arg Gln
                 65                      70          1

TGA CGG TAA ATG GCC CGC CTG GCA TTA TGC CCA GTA CAT GAC CTT ATG        562
    Arg     Met Ala Arg Leu Ala Leu Cys Pro Val His Asp Leu Met
     1       1               5                      10

GGA CTT TCC TAC TTG GCA GTA CAT CTA CGT ATT AGT CAT CGC TAT TAC        610
Gly Leu Ser Tyr Leu Ala Val His Leu Arg Ile Ser His Arg Tyr Tyr
         15                  20                  25

CAT GGT GAT GCG GTT TTG GCA GTA CAT CAA TGG GCG TGG ATA GCG GTT        658
His Gly Asp Ala Val Leu Ala Val His Gln Trp Ala Trp Ile Ala Val
 30                  35                  40                  45

TGA CTC ACG GGG ATT TCC AAG TCT CCA CCC CAT TGA CGT CAA TGG GAG        706
    Leu Thr Gly Ile Ser Lys Ser Pro Pro His     Arg Gln Trp Glu
     1               5                  10       1

TTT GTT TTG GCA CCA AAA TCA ACG GGA CTT TCC AAA ATG TCG                748
Phe Val Leu Ala Pro Lys Ser Thr Gly Leu Ser Lys Met Ser
 5              10                  15

TAA CAA CTC CGC CCC ATT GAC GCA AAT GGG CGG TAG CGC TGT ACG GTG        796
    Gln Leu Arg Pro Ile Asp Ala Asn Gly Arg     Arg Cys Thr Val
     1               5                  10       1

GGA GGT CTA TAT AAG CAG AGC TCT CTG GCT AAC TAG AGA ACC CAC TGC        844
Gly Gly Leu Tyr Lys Gln Ser Ser Leu Ala Asn     Arg Thr His Cys
 5                  10                  15       1

TTA CTG GCT TAT CGA AAT TAATACGACT CACTATAGGG AGACCCAAGC               892
Leu Leu Ala Tyr Arg Asn
 5                  10

TTCGCGCGGG TACCACTCTC TTCCGCATCG CTGTCTGCGA GGGCCAGCTG TTGGGCTCGC      952

GGTTGAGGAC AAACTCTTCG CGGTCTTTCC AGTACTCTTG GATCGGAAAC CCGTCGGCCT     1012

CCGAACGGTA CTCCGCCACC GAGGGACCTG AGCGAGTCCG CATCGACCGG ATCGGAAAAC     1072

CTCTCGAGGC GGCCGCTGCA GTCTAGACGA ATTCGCGTAC GATATCGATG GCCCTATT      1131

CTA TAG TGT CAC CTA AAT GCTAGAGCTC GCTGATCAGC CTCGACTGTG             1179
Leu     Cys His Leu Asn
 1       1

CCTTCTAGTT GCCAGCCATC TGTTGTTTGC CCCTCCCCCG TGCCTTCCTT GACCCTGGAA    1239

GGTGCCACTC CCACTGTCCT TTCCTAATAA AATGAGGAAA TTGCATCGCA TTGTCTGAGT     1299

AGGTGTCATT CTATTCTGGG GGGTGGGGTG GGGCAGGACA GCAAGGGGGA GGATTGGGAA     1359

GACAATAGCC GAAATGACCG ACCAAGCGAC GCCCAACCTG CCATCACGAG ATTTCGATTC     1419

CACCGCCGCC TTCTATGAAA GGTTGGGCTT CGGAATCGTT TTCCGGGACG CCGGCTGGAT     1479
```

```
GATCCTCCAG CGCGGGGATC TCATGCTGGA GTTCTTCGCC CACCCCAACT TGTTTATTGC    1539

AGCTTATAAT GGTTACAAAT AAAGCAATAG CATCACAAAT TTCACAAATA AAGCATTTTT    1599

TTCACTGCAT TCTAGTTGTG GTTTGTCCAA ACTCATCAAT GTATCTTATC ATGTCTGTAT    1659

ACCGTCGACC TCTAGCTAGA GCTTGGCGTA ATCATGGTCA TAGCTGTTTC CTGTGTGAAA    1719

TTGTTATCCG CTCACAATTC CACACAACAT ACGAGCCGGA AGCATAAAGT GTAAAGCCTG    1779

GGGTGCCTAA TGAGTGAGCT AACTCACATT AATTGCGTTG CGCTCACTGC CCGCTTTCCA    1839

GTCGGGAAAC CTGTCGTGCC AGCTGCATTA ATGAATCGGC CAACGCGCGG GGAGAGGCGG    1899

TTTGCGTATT GGGCGCTCTT CCGCTTCCTC GCTCACTGAC TCGCTGCGCT CGGTCGTTCG    1959

GCTGCGGCGA GCGGTATCAG CTCACTCAAA GGCGGTAATA CGGTTATCCA CAGAATCAGG    2019

GGATAACGCA GGAAAGAACA TGTGAGCAAA AGGCCAGCAA AAGGCCAGGA ACCGTAAAAA    2079

GGCCGCGTTG CTGGCGTTTT TCCATAGGCT CCGCCCCCCT GACGAGCATC ACAAAAATCG    2139

ACGCTCAAGT CAGAGGTGGC GAAACCCGAC AGGACTATAA AGATACCAGG CGTTTCCCCC    2199

TGGAAGCTCC CTCGTGCGCT CTCCTGTTCC GACCCTGCCG CTTACCGGAT ACCTGTCCGC    2259

CTTTCTCCCT TCGGGAAGCG TGGCGCTTTC TCAATGCTCA CGCTGTAGGT ATCTCAGTTC    2319

GGTGTAGGTC GTTCGCTCCA AGCTGGGCTG TGTGCACGAA CCCCCCGTTC AGCCCGACCG    2379

CTGCGCCTTA TCCGGTAACT ATCGTCTTGA GTCCAACCCG GTAAGACACG ACTTATCGCC    2439

ACTGGCAGCA GCCACTGGTA ACAGGATTAG CAGAGCGAGG TATGTAGGCG GTGCTACAGA    2499

GTTCTTGAAG TGGTGGCCTA ACTACGGCTA CACTAGAAGG ACAGTATTTG GTATCTGCGC    2559

TCTGCTGAAG CCAGTTACCT TCGGAAAAAG AGTTGGTAGC TCTTGATCCG GCAAACAAAC    2619

CACCGCTGGT AGCGGTGGTT TTTTTGTTTG CAAGCAGCAG ATTACGCGCA GAAAAAAAGG    2679

ATCTCAAGAA GATCCTTTGA TCTTTTCTAC GGGGTCTGAC GCTCAGTGGA ACGAAAACTC    2739

ACGTTAAGGG ATTTTGGTCA TGAGATTATC AAAAAGGATC TTCACCTAGA TCCTTTTAAA    2799

TTAAAAATGA AGTTTTAAAT CAATCTAAAG TATATATGAG TAAACTTGGT CTGACAGTTA    2859

CCAATGCTTA ATCAGTGAGG CACCTATCTC AGCGATCTGT CTATTTCGTT CATCCATAGT    2919

TGCCTGACTC CCCGTCGTGT AGATAACTAC GATACGGGAG GGCTTACCAT CTGGCCCCAG    2979

TGCTGCAATG ATACCGCGAG ACCCACGCTC ACCGGCTCCA GATTTATCAG CAATAAACCA    3039

GCCAGCCGGA AGGGCCGAGC GCAGAAGTGG TCCTGCAACT TTATCCGCCT CCATCCAGTC    3099

TATTAATTGT TGCCGGGAAG CTAGAGTAAG TAGTTCGCCA GTTAATAGTT TGCGCAACGT    3159

TGTTGCCATT GCTACAGGCA TCGTGGTGTC ACGCTCGTCG TTTGGTATGG CTTCATTCAG    3219

CTCCGGTTCC CAACGATCAA GGCGAGTTAC ATGATCCCCC ATGTTGTGCA AAAAAGCGGT    3279

TAGCTCCTTC GGTCCTCCGA TCGTTGTCAG AAGTAAGTTG GCCGCAGTGT TATCACTCAT    3339

GGTTATGGCA GCACTGCATA ATTCTCTTAC TGTCATGCCA TCCGTAAGAT GCTTTTCTGT    3399

GACTGGTGAG TACTCAACCA AGTCATTCTG AGAATAGTGT ATGCGGCGAC CGAGTTGCTC    3459

TTGCCCGGCG TCAATACGGG ATAATACCGC GCCACATAGC AGAACTTTAA AAGTGCTCAT    3519

CATTGGAAAA CGTTCTTCGG GGCGAAAACT CTCAAGGATC TTACCGCTGT TGAGATCCAG    3579

TTCGATGTAA CCCACTCGTG CACCCAACTG ATCTTCAGCA TCTTTTACTT TCACCAGCGT    3639

TTCTGGGTGA GCAAAAACAG GAAGGCAAAA TGCCGCAAAA AAGGGAATAA GGGCGACACG    3699

GAAATGTTGA ATACTCATAC TCTTCCTTTT TCAATATTAT TGAAGCATTT ATCAGGGTTA    3759

TTGTCTCATG AGCGGATACA TATTTGAATG TATTTAGAAA AATAAACAAA TAGGGGTTCC    3819

GCGCACATTT CCCCGAAAAG TGCCACCTGA CGTC                                3853
```

(2) INFORMATION FOR SEQ ID NO: 6:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 6:

```
Arg Cys Thr Gly Gln Ile Tyr Ala Leu Thr Leu Ile Ile Asp
 1               5                  10
```

(2) INFORMATION FOR SEQ ID NO: 7:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO: 7:

```
Leu Leu Ile Val Ile Asn Tyr Gly Val Ile Ser Ser
 1               5                  10
```

(2) INFORMATION FOR SEQ ID NO: 8:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO: 8:

```
Pro Ile Tyr Gly Val Pro Arg Tyr Ile Thr Tyr Gly Lys Trp Pro Ala
 1               5                  10                  15
Trp Leu Thr Ala Gln Arg Pro Pro Ile Asp Val Asn Asn Asp Val
                20                  25                  30
Cys Ser His Ser Asn Ala Asn Arg Asp Phe Pro Leu Thr Ser Met Gly
                35                  40                  45
Gly Leu Phe Thr Val Asn Cys Pro Leu Gly Ser Thr Ser Ser Val Ser
            50                  55                  60
Tyr Ala Lys Tyr Ala Pro Tyr
 65                  70
```

(2) INFORMATION FOR SEQ ID NO: 9:

(i) SEQUENCE CHARACTERISTICS:
        (A) LENGTH: 2 amino acids
        (B) TYPE: amino acid
        (D) TOPOLOGY: linear (ii) MOLECULE TYPE: protein (xi) SEQUENCE DESCRIPTION: SEQ ID NO: 9:

```
Arg Gln
 1
```

(2) INFORMATION FOR SEQ ID NO: 10:

(i) SEQUENCE CHARACTERISTICS:
        (A) LENGTH: 1 amino acids
        (B) TYPE: amino acid (D) TOPOLOGY: linear (ii) MOLECULE TYPE: protein (xi) SEQUENCE DESCRIPTION: SEQ ID NO: 10:

Arg
1

(2) INFORMATION FOR SEQ ID NO: 11:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO: 11:

Met Ala Arg Leu Ala Leu Cys Pro Val His Asp Leu Met Gly Leu Ser
1               5                   10                  15

Tyr Leu Ala Val His Leu Arg Ile Ser His Arg Tyr Tyr His Gly Asp
            20                  25                  30

Ala Val Leu Ala Val His Gln Trp Ala Trp Ile Ala Val
        35                  40                  45

(2) INFORMATION FOR SEQ ID NO: 12:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 12:

Leu Thr Gly Ile Ser Lys Ser Pro Pro His
1               5                   10

(2) INFORMATION FOR SEQ ID NO: 13:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO: 13:

Arg Gln Trp Glu Phe Val Leu Ala Pro Lys Ser Thr Gly Leu Ser Lys
1               5                   10                  15

Met Ser (2) INFORMATION FOR SEQ ID NO: 14:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 14:

Gln Leu Arg Pro Ile Asp Ala Asn Gly Arg
1               5                   10

(2) INFORMATION FOR SEQ ID NO: 15:

(i) SEQUENCE CHARACTERISTICS:
            (A) LENGTH: 15 amino acids
            (B) TYPE: amino acid
            (D) TOPOLOGY: linear (ii) MOLECULE TYPE: protein (xi) SEQUENCE DESCRIPTION: SEQ ID NO: 15:

Arg Cys Thr Val Gly Gly Leu Tyr Lys Gln Ser Ser Leu Ala Asn
 1               5                  10                  15

(2) INFORMATION FOR SEQ ID NO: 16:

(i) SEQUENCE CHARACTERISTICS:
            (A) LENGTH: 10 amino acids
            (B) TYPE: amino acid
            (D) TOPOLOGY: linear (ii) MOLECULE TYPE: protein (xi) SEQUENCE DESCRIPTION: SEQ ID NO: 16:

Arg Thr His Cys Leu Leu Ala Tyr Arg Asn
 1               5                  10

(2) INFORMATION FOR SEQ ID NO: 17:

(i) SEQUENCE CHARACTERISTICS:
            (A) LENGTH: 1 amino acids
            (B) TYPE: amino acid
            (D) TOPOLOGY: linear (ii) MOLECULE TYPE: protein (xi) SEQUENCE DESCRIPTION: SEQ ID NO: 17:

Leu
 1

(2) INFORMATION FOR SEQ ID NO: 18:

(i) SEQUENCE CHARACTERISTICS:
            (A) LENGTH: 4 amino acids
            (B) TYPE: amino acid
            (D) TOPOLOGY: linear (ii) MOLECULE TYPE: protein (xi) SEQUENCE DESCRIPTION: SEQ ID NO: 18:

Cys His Leu Asn
 1

(2) INFORMATION FOR SEQ ID NO: 19:

(i) SEQUENCE CHARACTERISTICS:
            (A) LENGTH: 4026 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 209..250

(ix) FEATURE:
            (A) NAME/KEY: CDS
            (B) LOCATION: 254..289

(ix) FEATURE:
            (A) NAME/KEY: CDS

```
        (B) LOCATION: 293..505

(ix) FEATURE:
         (A) NAME/KEY: CDS
         (B) LOCATION: 509..514

(ix) FEATURE:
         (A) NAME/KEY: CDS
         (B) LOCATION: 518..520

(ix) FEATURE:
         (A) NAME/KEY: CDS
         (B) LOCATION: 524..658

(ix) FEATURE:
         (A) NAME/KEY: CDS
         (B) LOCATION: 662..691

(ix) FEATURE:
         (A) NAME/KEY: CDS
         (B) LOCATION: 695..748

(ix) FEATURE:
         (A) NAME/KEY: CDS
         (B) LOCATION: 752..781

(ix) FEATURE:
         (A) NAME/KEY: CDS
         (B) LOCATION: 785..829

(ix) FEATURE:
         (A) NAME/KEY: CDS
         (B) LOCATION: 833..862

(ix) FEATURE:
         (A) NAME/KEY: CDS
         (B) LOCATION: 1305..1307

(ix) FEATURE:
         (A) NAME/KEY: CDS
         (B) LOCATION: 1311..1322

(xi) SEQUENCE DESCRIPTION: SEQ ID NO: 19:

GACGGATCGG GAGATCTCCC GATCCCCTAT GGTCGACTCT CAGTACAATC TGCTCTGATG      60

CCGCATAGTT AAGCCAGTAT CTGCTCCCTG CTTGTGTGTT GGAGGTCGCT GAGTAGTGCG     120

CGAGCAAAAT TTAAGCTACA ACAAGGCAAG GCTTGACCGA CAATTGCATG AAGAATCTGC     180

TTAGGGTTAG GCGTTTTGCG CTGCTTCG CGA TGT ACG GGC CAG ATA TAC GCG        232
                               Arg Cys Thr Gly Gln Ile Tyr Ala
                                 1               5

TTG ACA TTG ATT ATT GAC TAG TTA TTA ATA GTA ATC AAT TAC GGG GTC       280
Leu Thr Leu Ile Ile Asp     Leu Leu Ile Val Ile Asn Tyr Gly Val
       10                    1               5

ATT AGT TCA TAG CCC ATA TAT GGA GTT CCG CGT TAC ATA ACT TAC GGT       328
Ile Ser Ser     Pro Ile Tyr Gly Val Pro Arg Tyr Ile Thr Tyr Gly
 10                  1               5                  10

AAA TGG CCC GCC TGG CTG ACC GCC CAA CGA CCC CCG CCC ATT GAC GTC       376
Lys Trp Pro Ala Trp Leu Thr Ala Gln Arg Pro Pro Pro Ile Asp Val
           15                  20                  25

AAT AAT GAC GTA TGT TCC CAT AGT AAC GCC AAT AGG GAC TTT CCA TTG       424
Asn Asn Asp Val Cys Ser His Ser Asn Ala Asn Arg Asp Phe Pro Leu
       30                  35                  40

ACG TCA ATG GGT GGA CTA TTT ACG GTA AAC TGC CCA CTT GGC AGT ACA       472
Thr Ser Met Gly Gly Leu Phe Thr Val Asn Cys Pro Leu Gly Ser Thr
   45                  50                  55                  60

TCA AGT GTA TCA TAT GCC AAG TAC GCC CCC TAT TGA CGT CAA               514
Ser Ser Val Ser Tyr Ala Lys Tyr Ala Pro Tyr     Arg Gln
               65                  70              1

TGA CGG TAA ATG GCC CGC CTG GCA TTA TGC CCA GTA CAT GAC CTT ATG       562
```

```
        Arg     Met Ala Arg Leu Ala Leu Cys Pro Val His Asp Leu Met
         1       1           5                  10

GGA CTT TCC TAC TTG GCA GTA CAT CTA CGT ATT AGT CAT CGC TAT TAC        610
Gly Leu Ser Tyr Leu Ala Val His Leu Arg Ile Ser His Arg Tyr Tyr
 15              20                  25

CAT GGT GAT GCG GTT TTG GCA GTA CAT CAA TGG GCG TGG ATA GCG GTT        658
His Gly Asp Ala Val Leu Ala Val His Gln Trp Ala Trp Ile Ala Val
 30              35                  40                  45

TGA CTC ACG GGG ATT TCC AAG TCT CCA CCC CAT TGA CGT CAA TGG GAG        706
    Leu Thr Gly Ile Ser Lys Ser Pro Pro His     Arg Gln Trp Glu
     1               5                  10       1

TTT GTT TTG GCA CCA AAA TCA ACG GGA CTT TCC AAA ATG TCG                748
Phe Val Leu Ala Pro Lys Ser Thr Gly Leu Ser Lys Met Ser
 5              10                  15

TAA CAA CTC CGC CCC ATT GAC GCA AAT GGG CGG TAG GCG TGT ACG GTG        796
    Gln Leu Arg Pro Ile Asp Ala Asn Gly Arg     Ala Cys Thr Val
     1               5                  10       1

GGA GGT CTA TAT AAG CAG AGC TCT CTG GCT AAC TAG AGA ACC CAC TGC        844
Gly Gly Leu Tyr Lys Gln Ser Ser Leu Ala Asn     Arg Thr His Cys
 5              10                  15           1

TTA CTG GCT TAT CGA AAT TAATACGACT CACTATAGGG AGACCCAAGC               892
Leu Leu Ala Tyr Arg Asn
 5              10

TTCGCGCGGG TACCACTCTC TTCCGCATCG CTGTCTGCGA GGGCCAGCTG TTGGGCTCGC      952

GGTTGAGGAC AAACTCTTCG CGGTCTTTCC AGTACTCTTG GATCGGAAAC CCGTCGGCCT      1012

CCGAACGGTA CTCCGCCACC GAGGGACCTG AGCGAGTCCG CATCGACCGG ATCGGAAAAC      1072

CTCTCGAGGA ACTGAAAAAC CAGAAAGTTA ACTGGTAAGT TTAGTCTTTT TGTCTTTTTA      1132

TTTCAGGTCC CGGATCCGGT GGTGGTGCAA ATCAAAGAAC TGCTCCTCAG TGGATGTTGC      1192

CTTTACTTCT AGGCCTGTAC GGAAGTGTTA CTTCTGCTCT AAAAGCTGCG GAATTGTACC      1252

CGCGGCCGCT GCAGTCTAGA CGAATTCGCG TACGATATCG ATGGGCCCTA TT CTA         1307
                                                         Leu
                                                          1

TAG TGT CAC CTA AAT GCTAGAGCTC GCTGATCAGC CTCGACTGTG CCTTCTAGTT        1362
    Cys His Leu Asn
     1

GCCAGCCATC TGTTGTTTGC CCCTCCCCCG TGCCTTCCTT GACCCTGGAA GGTGCCACTC      1422

CCACTGTCCT TTCCTAATAA AATGAGGAAA TTGCATCGCA TTGTCTGAGT AGGTGTCATT      1482

CTATTCTGGG GGGTGGGGTG GGGCAGGACA GCAAGGGGGA GGATTGGGAA GACAATAGCC      1542

GAAATGACCG ACCAAGCGAC GCCCAACCTG CCATCACGAG ATTTCGATTC CACCGCCGCC      1602

TTCTATGAAA GGTTGGGCTT CGGAATCGTT TTCCGGGACG CCGGCTGGAT GATCCTCCAG      1662

CGCGGGATC TCATGCTGGA GTTCTTCGCC CACCCCAACT TGTTTATTGC AGCTTATAAT       1722

GGTTACAAAT AAAGCAATAG CATCACAAAT TTCACAAATA AAGCATTTTT TTCACTGCAT      1782

TCTAGTTGTG GTTTGTCCAA ACTCATCAAT GTATCTTATC ATGTCTGTAT ACCGTCGACC      1842

TCTAGCTAGA GCTTGGCGTA ATCATGGTCA TAGCTGTTTC CTGTGTGAAA TTGTTATCCG      1902

CTCACAATTC CACACAACAT ACGAGCCGGA AGCATAAAGT GTAAAGCCTG GGGTGCCTAA      1962

TGAGTGAGCT AACTCACATT AATTGCGTTG CGCTCACTGC CCGCTTTCCA GTCGGGAAAC      2022

CTGTCGTGCC AGCTGCATTA ATGAATCGGC CAACGCGCGG GGAGAGGCGG TTTGCGTATT      2082

GGGCGCTCTT CCGCTTCCTC GCTCACTGAC TCGCTGCGCT CGGTCGTTCG GCTGCGGCGA      2142

GCGGTATCAG CTCACTCAAA GGCGGTAATA CGGTTATCCA CAGAATCAGG GGATAACGCA      2202
```

| | |
|---|---|
| GGAAAGAACA TGTGAGCAAA AGGCCAGCAA AAGGCCAGGA ACCGTAAAAA GGCCGCGTTG | 2262 |
| CTGGCGTTTT TCCATAGGCT CCGCCCCCCT GACGAGCATC ACAAAAATCG ACGCTCAAGT | 2322 |
| CAGAGGTGGC GAAACCCGAC AGGACTATAA AGATACCAGG CGTTTCCCCC TGGAAGCTCC | 2382 |
| CTCGTGCGCT CTCCTGTTCC GACCCTGCCG CTTACCGGAT ACCTGTCCGC CTTTCTCCCT | 2442 |
| TCGGGAAGCG TGGCGCTTTC TCAATGCTCA CGCTGTAGGT ATCTGAGTTC GGTGTAGGTC | 2502 |
| GTTCGCTCCA AGCTGGGCTG TGTGCACGAA CCCCCCGTTC AGCCCGACCG CTGCGCCTTA | 2562 |
| TCCGGTAACT ATCGTCTTGA GTCCAACCCG GTAAGACACG ACTTATCGCC ACTGGCAGCA | 2622 |
| GCCACTGGTA ACAGGATTAG CAGAGCGAGG TATGTAGGCG GTGCTACAGA GTTCTTGAAG | 2682 |
| TGGTGGCCTA ACTACGGCTA CACTAGAAGG ACAGTATTTG GTATCTGCGC TCTGCTGAAG | 2742 |
| CCAGTTACCT TCGGAAAAAG AGTTGGTAGC TCTTGATCCG GCAAACAAAC CACCGCTGGT | 2802 |
| AGCGGTGGTT TTTTTGTTTG CAAGCAGCAG ATTACGCGCA GAAAAAAAGG ATCTCAAGAA | 2862 |
| GATCCTTTGA TCTTTTCTAC GGGGTCTGAC GCTCAGTGGA ACGAAAACTC ACGTTAAGGG | 2922 |
| ATTTTGGTCA TGAGATTATC AAAAAGGATC TTCACCTAGA TCCTTTTAAA TTAAAAATGA | 2982 |
| AGTTTTAAAT CAATCTAAAG TATATATGAG TAAACTTGGT CTGACAGTTA CCAATGCTTA | 3042 |
| ATCAGTGAGG CACCTATCTC AGCGATCTGT CTATTTCGTT CATCCATAGT TGCCTGACTC | 3102 |
| CCCGTCGTGT AGATAACTAC GATACGGGAG GGCTTACCAT CTGGCCCCAG TGCTGCAATG | 3162 |
| ATACCGCGAG ACCCACGCTC ACCGGCTCCA GATTTATCAG CAATAAACCA GCCAGCCGGA | 3222 |
| AGGGCCGAGC GCAGAAGTGG TCCTGCAACT TTATCCGCCT CCATCCAGTC TATTAATTGT | 3282 |
| TGCCGGGAAG CTAGAGTAAG TAGTTCGCCA GTTAATAGTT TGCGCAACGT TGTTGCCATT | 3342 |
| GCTACAGGCA TCGTGGTGTC ACGCTCGTCG TTTGGTATGG CTTCATTCAG CTCCGGTTCC | 3402 |
| CAACGATCAA GGCGAGTTAC ATGATCCCCC ATGTTGTGCA AAAAAGCGGT TAGCTCCTTC | 3462 |
| GGTCCTCCGA TCGTTGTCAG AAGTAAGTTG GCCGCAGTGT TATCACTCAT GGTTATGGCA | 3522 |
| GCACTGCATA ATTCTCTTAC TGTCATGCCA TCCGTAAGAT GCTTTTCTGT GACTGGTGAG | 3582 |
| TACTCAACCA AGTCATTCTG AGAATAGTGT ATGCGGCGAC CGAGTTGCTC TTGCCCGGCG | 3642 |
| TCAATACGGG ATAATACCGC GCCACATAGC AGAACTTTAA AAGTGCTCAT CATTGGAAAA | 3702 |
| CGTTCTTCGG GGCGAAAACT CTCAAGGATC TTACCGCTGT TGAGATCCAG TTCGATGTAA | 3762 |
| CCCACTCGTG CACCCAACTG ATCTTCAGCA TCTTTTACTT TCACCAGCGT TTCTGGGTGA | 3822 |
| GCAAAAACAG GAAGGCAAAA TGCCGCAAAA AAGGGAATAA GGGCGACACG GAAATGTTGA | 3882 |
| ATACTCATAC TCTTCCTTTT TCAATATTAT TGAAGCATTT ATCAGGGTTA TTGTCTCATG | 3942 |
| AGCGGATACA TATTTGAATG TATTTAGAAA AATAAACAAA TAGGGGTTCC GCGCACATTT | 4002 |
| CCCCGAAAAG TGCCACCTGA CGTC | 4026 |

(2) INFORMATION FOR SEQ ID NO: 20:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 20:

Arg Cys Thr Gly Gln Ile Tyr Ala Leu Thr Leu Ile Ile Asp
 1          5              10

(2) INFORMATION FOR SEQ ID NO: 21:

(i) SEQUENCE CHARACTERISTICS:
    (A) LENGTH: 12 amino acids
    (B) TYPE: amino acid
    (D) TOPOLOGY: linear (ii) MOLECULE TYPE: protein (xi) SEQUENCE DESCRIPTION: SEQ ID NO: 21:

Leu Leu Ile Val Ile Asn Tyr Gly Val Ile Ser Ser
 1               5                  10

(2) INFORMATION FOR SEQ ID NO: 22:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO: 22:

Pro Ile Tyr Gly Val Pro Arg Tyr Ile Thr Tyr Gly Lys Trp Pro Ala
 1               5                  10                  15

Trp Leu Thr Ala Gln Arg Pro Pro Ile Asp Val Asn Asn Asp Val
             20                  25                  30

Cys Ser His Ser Asn Ala Asn Arg Asp Phe Pro Leu Thr Ser Met Gly
             35                  40                  45

Gly Leu Phe Thr Val Asn Cys Pro Leu Gly Ser Thr Ser Ser Val Ser
         50                  55                  60

Tyr Ala Lys Tyr Ala Pro Tyr
65                  70

(2) INFORMATION FOR SEQ ID NO: 23:

(i) SEQUENCE CHARACTERISTICS:
        (A) LENGTH: 2 amino acids
        (B) TYPE: amino acid
        (D) TOPOLOGY: linear (ii) MOLECULE TYPE: protein (xi) SEQUENCE DESCRIPTION: SEQ ID NO: 23:

Arg Gln
 1

(2) INFORMATION FOR SEQ ID NO: 24:

(i) SEQUENCE CHARACTERISTICS:
        (A) LENGTH: 1 amino acids
        (B) TYPE: amino acid
        (D) TOPOLOGY: linear (ii) MOLECULE TYPE: protein (xi) SEQUENCE DESCRIPTION: SEQ ID NO: 24:

Arg
 1

(2) INFORMATION FOR SEQ ID NO: 25:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO: 25:

Met Ala Arg Leu Ala Leu Cys Pro Val His Asp Leu Met Gly Leu Ser
1               5                   10                  15

Tyr Leu Ala Val His Leu Arg Ile Ser His Arg Tyr His Gly Asp
            20                  25                  30

Ala Val Leu Ala Val His Gln Trp Ala Trp Ile Ala Val
        35                  40                  45

(2) INFORMATION FOR SEQ ID NO: 26:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 26:

Leu Thr Gly Ile Ser Lys Ser Pro Pro His
1               5                   10

(2) INFORMATION FOR SEQ ID NO: 27:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO: 27:

Arg Gln Trp Glu Phe Val Leu Ala Pro Lys Ser Thr Gly Leu Ser Lys
1               5                   10                  15

Met Ser (2) INFORMATION FOR SEQ ID NO: 28:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 28:

Gln Leu Arg Pro Ile Asp Ala Asn Gly Arg
1               5                   10

(2) INFORMATION FOR SEQ ID NO: 29:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO: 29:

Ala Cys Thr Val Gly Gly Leu Tyr Lys Gln Ser Ser Leu Ala Asn
1               5                   10                  15

(2) INFORMATION FOR SEQ ID NO: 30:

(i) SEQUENCE CHARACTERISTICS:
        (A) LENGTH: 10 amino acids

```
            (B) TYPE: amino acid
            (D) TOPOLOGY: linear (ii) MOLECULE TYPE: protein (xi) SEQUENCE DESCRIPTION: SEQ ID NO: 30:

Arg Thr His Cys Leu Leu Ala Tyr Arg Asn
  1               5                  10

(2) INFORMATION FOR SEQ ID NO: 31:

(i) SEQUENCE CHARACTERISTICS:
            (A) LENGTH: 1 amino acids
            (B) TYPE: amino acid
            (D) TOPOLOGY: linear (ii) MOLECULE TYPE: protein (xi) SEQUENCE DESCRIPTION: SEQ ID NO: 31:

Leu
  1

(2) INFORMATION FOR SEQ ID NO: 32:

(i) SEQUENCE CHARACTERISTICS:
            (A) LENGTH: 4 amino acids
            (B) TYPE: amino acid
            (D) TOPOLOGY: linear (ii) MOLECULE TYPE: protein (xi) SEQUENCE DESCRIPTION: SEQ ID NO: 32:

Cys His Leu Asn
  1

(2) INFORMATION FOR SEQ ID NO: 33:

(i) SEQUENCE CHARACTERISTICS:
            (A) LENGTH: 4249 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 209..250

(ix) FEATURE:
            (A) NAME/KEY: CDS
            (B) LOCATION: 254..289

(ix) FEATURE:
            (A) NAME/KEY: CDS
            (B) LOCATION: 293..505

(ix) FEATURE:
            (A) NAME/KEY: CDS
            (B) LOCATION: 509..514

(ix) FEATURE:
            (A) NAME/KEY: CDS
            (B) LOCATION: 518..520

(ix) FEATURE:
            (A) NAME/KEY: CDS
            (B) LOCATION: 524..658

(ix) FEATURE:
            (A) NAME/KEY: CDS
            (B) LOCATION: 662..691
```

```
    (ix) FEATURE:
         (A) NAME/KEY: CDS
         (B) LOCATION: 695..748

(ix) FEATURE:
         (A) NAME/KEY: CDS
         (B) LOCATION: 752..781

(ix) FEATURE:
         (A) NAME/KEY: CDS
         (B) LOCATION: 785..829

(ix) FEATURE:
         (A) NAME/KEY: CDS
         (B) LOCATION: 833..862

(ix) FEATURE:
         (A) NAME/KEY: CDS
         (B) LOCATION: 1528..1530

(ix) FEATURE:
         (A) NAME/KEY: CDS
         (B) LOCATION: 1534..1545

(xi) SEQUENCE DESCRIPTION: SEQ ID NO: 33:

GACGGATCGG GAGATCTCCC GATCCCCTAT GGTCGACTCT CAGTACAATC TGCTCTGATG      60

CCGCATAGTT AAGCCAGTAT CTGCTCCCTG CTTGTGTGTT GGAGGTCGCT GAGTAGTGCG     120

CGAGCAAAAT TTAAGCTACA ACAAGGCAAG GCTTGACCGA CAATTGCATG AAGAATCTGC     180

TTAGGGTTAG GCGTTTTGCG CTGCTTCG CGA TGT ACG GGC CAG ATA TAC GCG        232
                               Arg Cys Thr Gly Gln Ile Tyr Ala
                                 1               5

TTG ACA TTG ATT ATT GAC TAG TTA TTA ATA GTA ATC AAT TAC GGG GTC       280
Leu Thr Leu Ile Ile Asp     Leu Leu Ile Val Ile Asn Tyr Gly Val
         10                   1               5

ATT AGT TCA TAG CCC ATA TAT GGA GTT CCG CGT TAC ATA ACT TAC GGT       328
Ile Ser Ser     Pro Ile Tyr Gly Val Pro Arg Tyr Ile Thr Tyr Gly
     10           1               5                      10

AAA TGG CCC GCC TGG CTG ACC GCC CAA CGA CCC CCG CCC ATT GAC GTC       376
Lys Trp Pro Ala Trp Leu Thr Ala Gln Arg Pro Pro Pro Ile Asp Val
             15              20              25

AAT AAT GAC GTA TGT TCC CAT AGT AAC GCC AAT AGG GAC TTT CCA TTG       424
Asn Asn Asp Val Cys Ser His Ser Asn Ala Asn Arg Asp Phe Pro Leu
         30              35              40

ACG TCA ATG GGT GGA CTA TTT ACG GTA AAC TGC CCA CTT GGC AGT ACA       472
Thr Ser Met Gly Gly Leu Phe Thr Val Asn Cys Pro Leu Gly Ser Thr
     45              50              55                      60

TCA AGT GTA TCA TAT GCC AAG TAC GCC CCC TAT TGA CGT CAA               514
Ser Ser Val Ser Tyr Ala Lys Tyr Ala Pro Tyr     Arg Gln
             65              70                   1

TGA CGG TAA ATG GCC CGC CTG GCA TTA TGC CCA GTA CAT GAC CTT ATG       562
    Arg     Met Ala Arg Leu Ala Leu Cys Pro Val His Asp Leu Met
     1       1           5                      10

GGA CTT TCC TAC TTG GCA GTA CAT CTA CGT ATT AGT CAT CGC TAT TAC       610
Gly Leu Ser Tyr Leu Ala Val His Leu Arg Ile Ser His Arg Tyr Tyr
         15              20              25

CAT GGT GAT GCG GTT TTG GCA GTA CAT CAA TGG GCG TGG ATA GCG GTT       658
His Gly Asp Ala Val Leu Ala Val His Gln Trp Ala Trp Ile Ala Val
     30              35              40                      45

TGA CTC ACG GGG ATT TCC AAG TCT CCA CCC CAT TGA CGT CAA TGG GAG       706
    Leu Thr Gly Ile Ser Lys Ser Pro Pro His     Arg Gln Trp Glu
     1           5              10               1

TTT GTT TTG GCA CCA AAA TCA ACG GGA CTT TCC AAA ATG TCG               748
Phe Val Leu Ala Pro Lys Ser Thr Gly Leu Ser Lys Met Ser
 5              10              15
```

-continued

```
TAA CAA CTC CGC CCC ATT GAC GCA AAT GGG CGG TAG GCG TGT ACG GTG      796
    Gln Leu Arg Pro Ile Asp Ala Asn Gly Arg     Ala Cys Thr Val
     1               5                  10       1
GGA GGT CTA TAT AAG CAG AGC TCT CTG GCT AAC TAG AGA ACC CAC TGC      844
Gly Gly Leu Tyr Lys Gln Ser Ser Leu Ala Asn     Arg Thr His Cys
 5               10                  15          1
TTA CTG GCT TAT CGA AAT TAATACGACT CACTATAGGG AGACCCAAGC             892
Leu Leu Ala Tyr Arg Asn
 5               10
TTCGCGCGGG TACCACTCTC TTCCGCATCG CTGTCTGCGA GGGCCAGCTG TTGGGCTCGC    952
GGTTGAGGAC AAACTCTTCG CGGTCTTTCC AGTACTCTTG GATCGGAAAC CCGTCGGCCT   1012
CCGAACGGTA CTCCGCCACC GAGGGACCTG AGCGAGTCCG CATCGACCGG ATCGGAAAAC   1072
CTCTCGAGGA ACTGAAAAAC CAGAAAGTTA ACTGGTAAGT TTAGTCTTTT TGTCTTTTTA   1132
TTTCAGGTCC CGGATCTGAG TTAGGGCGGG ACATGGGCGG AGTTAGGGGC GGGACTATGG   1192
TTGCTGACTA ATTGAGATGC ATGCTTTGCA TACTTCTGCC TGCTGGGGAG CCTGGGGACT   1252
TTCCACACCT GGTTGCTGAC TAATTGAGAT GCATGCTTTG CATACTTCTG CCTGCTGGGG   1312
AGCCTGGGGA CTTTCCACAC CCTAACTGAC ACACATTCCA CAGCTGGTTC TTTCAGATCC   1372
GGTGGTGGTG CAAATCAAAG AACTGCTCCT CAGTGGATGT TGCCTTTACT TCTAGGCCTG   1432
TACGGAAGTG TTACTTCTGC TCTAAAAGCT GCGGAATTGT ACCCGCGGCC GCTGCAGTCT   1492
AGACGAATTC GCGTACGATA TCGATGGGCC CTATT CTA TAG TGT CAC CTA AAT     1545
                                        Leu     Cys His Leu Asn
                                         1       1
GCTAGAGCTC GCTGATCAGC CTCGACTGTG CCTTCTAGTT GCCAGCCATC TGTTGTTTGC   1605
CCCTCCCCCG TGCCTTCCTT GACCCTGGAA GGTGCCACTC CCACTGTCCT TCCTAATAA   1665
AATGAGGAAA TTGCATCGCA TTGTCTGAGT AGGTGTCATT CTATTCTGGG GGGTGGGGTG   1725
GGGCAGGACA GCAAGGGGGA GGATTGGGAA GACAATAGCC GAAATGACCG ACCAAGCGAC   1785
GCCCAACCTG CCATCACGAG ATTTCGATTC CACCGCCGCC TTCTATGAAA GGTTGGGCTT   1845
CGGAATCGTT TTCCGGGACG CCGGCTGGAT GATCCTCCAG CGCGGGATC TCATGCTGGA   1905
GTTCTTCGCC CACCCCAACT TGTTTATTGC AGCTTATAAT GGTTACAAAT AAAGCAATAG   1965
CATCACAAAT TTCACAAATA AAGCATTTTT TTCACTGCAT TCTAGTTGTG GTTTGTCCAA   2025
ACTCATCAAT GTATCTTATC ATGTCTGTAT ACCGTCGACC TCTAGCTAGA GCTTGGCGTA   2085
ATCATGGTCA TAGCTGTTTC CTGTGTGAAA TTGTTATCCG CTCACAATTC CACACAACAT   2145
ACGAGCCGGA AGCATAAAGT GTAAAGCCTG GGGTGCCTAA TGAGTGAGCT AACTCACATT   2205
AATTGCGTTG CGCTCACTGC CCGCTTTCCA GTCGGGAAAC CTGTCGTGCC AGCTGCATTA   2265
ATGAATCGGC CAACGCGCGG GGAGAGGCGG TTTGCGTATT GGGCGCTCTT CCGCTTCCTC   2325
GCTCACTGAC TCGCTGCGCT CGGTCGTTCG GCTGCGGCGA GCGGTATCAG CTCACTCAAA   2385
GGCGGTAATA CGGTTATCCA CAGAATCAGG GGATAACGCA GGAAAGAACA TGTGAGCAAA   2445
AGGCCAGCAA AAGGCCAGGA ACCGTAAAAA GGCCGCGTTG CTGGCGTTTT TCCATAGGCT   2505
CCGCCCCCCT GACGAGCATC ACAAAATCG ACGCTCAAGT CAGAGGTGGC GAAACCCGAC   2565
AGGACTATAA AGATACCAGG CGTTTCCCCC TGGAAGCTCC CTCGTGCGCT CTCCTGTTCC   2625
GACCCTGCCG CTTACCGGAT ACCTGTCCGC CTTTCTCCCT TCGGGAAGCG TGGCGCTTTC   2685
TCAATGCTCA CGCTGTAGGT ATCTCAGTTC GGTGTAGGTC GTTCGCTCCA AGCTGGGCTG   2745
TGTGCACGAA CCCCCCGTTC AGCCCGACCG CTGCGCCTTA TCCGGTAACT ATCGTCTTGA   2805
```

```
GTCCAACCCG GTAAGACACG ACTTATCGCC ACTGGCAGCA GCCACTGGTA ACAGGATTAG      2865

CAGAGCGAGG TATGTAGGCG GTGCTACAGA GTTCTTGAAG TGGTGGCCTA ACTACGGCTA      2925

CACTAGAAGG ACAGTATTTG GTATCTGCGC TCTGCTGAAG CCAGTTACCT TCGGAAAAAG      2985

AGTTGGTAGC TCTTGATCCG GCAAACAAAC CACCGCTGGT AGCGGTGGTT TTTTTGTTTG      3045

CAAGCAGCAG ATTACGCGCA GAAAAAAAGG ATCTCAAGAA GATCCTTTGA TCTTTTCTAC      3105

GGGGTCTGAC GCTCAGTGGA ACGAAAACTC ACGTTAAGGG ATTTTGGTCA TGAGATTATC      3165

AAAAAGGATC TTCACCTAGA TCCTTTTAAA TTAAAAATGA AGTTTTAAAT CAATCTAAAG      3225

TATATATGAG TAAACTTGGT CTGACAGTTA CCAATGCTTA ATCAGTGAGG CACCTATCTC      3285

AGCGATCTGT CTATTTCGTT CATCCATAGT TGCCTGACTC CCCGTCGTGT AGATAACTAC      3345

GATACGGGAG GGCTTACCAT CTGGCCCCAG TGCTGCAATG ATACCGCGAG ACCCACGCTC      3405

ACCGGCTCCA GATTTATCAG CAATAAACCA GCCAGCCGGA AGGGCCGAGC GCAGAAGTGG      3465

TCCTGCAACT TTATCCGCCT CCATCCAGTC TATTAATTGT TGCCGGGAAG CTAGAGTAAG      3525

TAGTTCGCCA GTTAATAGTT TGCGCAACGT TGTTGCCATT GCTACAGGCA TCGTGGTGTC      3585

ACGCTCGTCG TTTGGTATGG CTTCATTCAG CTCCGGTTCC CAACGATCAA GGCGAGTTAC      3645

ATGATCCCCC ATGTTGTGCA AAAAAGCGGT TAGCTCCTTC GGTCCTCCGA TCGTTGTCAG      3705

AAGTAAGTTG GCCGCAGTGT TATCACTCAT GGTTATGGCA GCACTGCATA ATTCTCTTAC      3765

TGTCATGCCA TCCGTAAGAT GCTTTTCTGT GACTGGTGAG TACTCAACCA AGTCATTCTG      3825

AGAATAGTGT ATGCGGCGAC CGAGTTGCTC TTGCCCGGCG TCAATACGGG ATAATACCGC      3885

GCCACATAGC AGAACTTTAA AAGTGCTCAT CATTGGAAAA CGTTCTTCGG GGCGAAAACT      3945

CTCAAGGATC TTACCGCTGT TGAGATCCAG TTCGATGTAA CCCACTCGTG CACCCAACTG      4005

ATCTTCAGCA TCTTTTACTT TCACCAGCGT TTCTGGGTGA GCAAAAACAG GAAGGCAAAA      4065

TGCCGCAAAA AAGGGAATAA GGGCGACACG GAAATGTTGA ATACTCATAC TCTTCCTTTT      4125

TCAATATTAT TGAAGCATTT ATCAGGGTTA TTGTCTCATG AGCGGATACA TATTTGAATG      4185

TATTTAGAAA AATAAACAAA TAGGGGTTCC GCGCACATTT CCCCGAAAAG TGCCACCTGA      4245

CGTC                                                                  4249
```

(2) INFORMATION FOR SEQ ID NO: 34:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 34:

Arg Cys Thr Gly Gln Ile Tyr Ala Leu Thr Leu Ile Ile Asp
 1               5                  10

(2) INFORMATION FOR SEQ ID NO: 35:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO: 35:

Leu Leu Ile Val Ile Asn Tyr Gly Val Ile Ser Ser
 1               5                  10

(2) INFORMATION FOR SEQ ID NO: 36:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO: 36:

```
Pro Ile Tyr Gly Val Pro Arg Tyr Ile Thr Tyr Gly Lys Trp Pro Ala
 1               5                  10                  15

Trp Leu Thr Ala Gln Arg Pro Pro Ile Asp Val Asn Asn Asp Val
             20                  25                  30

Cys Ser His Ser Asn Ala Asn Arg Asp Phe Pro Leu Thr Ser Met Gly
             35                  40                  45

Gly Leu Phe Thr Val Asn Cys Pro Leu Gly Ser Thr Ser Ser Val Ser
         50                  55                  60

Tyr Ala Lys Tyr Ala Pro Tyr
 65                  70
```

(2) INFORMATION FOR SEQ ID NO: 37:

(i) SEQUENCE CHARACTERISTICS:
        (A) LENGTH: 2 amino acids
        (B) TYPE: amino acid
        (D) TOPOLOGY: linear (ii) MOLECULE TYPE: protein (xi) SEQUENCE DESCRIPTION: SEQ ID NO: 37:

```
Arg Gln
 1
```

(2) INFORMATION FOR SEQ ID NO: 38:

(i) SEQUENCE CHARACTERISTICS:
        (A) LENGTH: 1 amino acids
        (B) TYPE: amino acid
        (D) TOPOLOGY: linear (ii) MOLECULE TYPE: protein (xi) SEQUENCE DESCRIPTION: SEQ ID NO: 38:

```
Arg
 1
```

(2) INFORMATION FOR SEQ ID NO: 39:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO: 39:

```
Met Ala Arg Leu Ala Leu Cys Pro Val His Asp Leu Met Gly Leu Ser
 1               5                  10                  15

Tyr Leu Ala Val His Leu Arg Ile Ser His Arg Tyr Tyr His Gly Asp
             20                  25                  30

Ala Val Leu Ala Val His Gln Trp Ala Trp Ile Ala Val
             35                  40                  45
```

(2) INFORMATION FOR SEQ ID NO: 40:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 40:

Leu Thr Gly Ile Ser Lys Ser Pro Pro His
 1             5                10

(2) INFORMATION FOR SEQ ID NO: 41:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO: 41:

Arg Gln Trp Glu Phe Val Leu Ala Pro Lys Ser Thr Gly Leu Ser Lys
 1             5               10              15

Met Ser (2) INFORMATION FOR SEQ ID NO: 42:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 42:

Gln Leu Arg Pro Ile Asp Ala Asn Gly Arg
 1             5                10

(2) INFORMATION FOR SEQ ID NO: 43:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO: 43:

Ala Cys Thr Val Gly Gly Leu Tyr Lys Gln Ser Ser Leu Ala Asn
 1             5               10              15

(2) INFORMATION FOR SEQ ID NO: 44:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 44:

Arg Thr His Cys Leu Leu Ala Tyr Arg Asn
 1             5                10

(2) INFORMATION FOR SEQ ID NO: 45:

(i) SEQUENCE CHARACTERISTICS:
        (A) LENGTH: 1 amino acids
        (B) TYPE: amino acid
        (D) TOPOLOGY: linear (ii) MOLECULE TYPE: protein (xi) SEQUENCE DESCRIPTION: SEQ ID NO: 45:

Leu
  1

(2) INFORMATION FOR SEQ ID NO: 46:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 46:

Cys His Leu Asn
```